United States Patent
Li et al.

(10) Patent No.: US 10,280,229 B2
(45) Date of Patent: May 7, 2019

(54) LINKERS AND THEIR APPLICATION TOWARDS ADC

(71) Applicant: MEDSHINE DISCOVERY INC., Nanjing, Jiangsu (CN)

(72) Inventors: Chun Sing Li, Shanghai (CN); Jian Li, Shanghai (CN); Yong Cang, Shanghai (CN); Shuhui Chen, Shanghai (CN); Gang Li, Shanghai (CN); Xiongbin Xu, Shanghai (CN); Lun Lu, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 31 days.

(21) Appl. No.: 15/326,386

(22) PCT Filed: Jul. 13, 2015

(86) PCT No.: PCT/CN2015/083840
§ 371 (c)(1),
(2) Date: Jan. 13, 2017

(87) PCT Pub. No.: WO2016/008392
PCT Pub. Date: Jan. 21, 2016

(65) Prior Publication Data
US 2017/0202974 A1    Jul. 20, 2017

(30) Foreign Application Priority Data

Jul. 16, 2014 (WO) ................ PCT/CN2014/082292

(51) Int. Cl.
| | | |
|---|---|---|
| *A61K 47/68* | (2017.01) | |
| *C07K 16/30* | (2006.01) | |
| *C07K 16/28* | (2006.01) | |
| *C07K 19/00* | (2006.01) | |

(52) U.S. Cl.
CPC ...... *C07K 16/3015* (2013.01); *A61K 47/6803* (2017.08); *A61K 47/6817* (2017.08); *A61K 47/6851* (2017.08); *A61K 47/6855* (2017.08); *A61K 47/6889* (2017.08); *C07K 16/2863* (2013.01); *C07K 2317/24* (2013.01)

(58) Field of Classification Search
CPC ............ C07K 16/3015; C07K 16/2863; C07K 2317/24; A61K 47/6889; A61K 47/6851; A61K 47/6803; A61K 47/6855; A61K 47/6817
USPC ....................................................... 548/545
See application file for complete search history.

(56) References Cited

U.S. PATENT DOCUMENTS

| | | |
|---|---|---|
| 5,885,793 A | 3/1999 | Griffiths et al. |
| 6,130,237 A | 10/2000 | Denny et al. |
| 8,163,888 B2 | 4/2012 | Steeves et al. |
| 2003/0083263 A1 | 5/2003 | Doronina et al. |
| 2005/0009751 A1 | 1/2005 | Senter et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2007/0082365 A1 | 4/2007 | Lipovsek et al. |
| 2008/0226657 A1 | 9/2008 | Doronina et al. |
| 2008/0311134 A1 | 12/2008 | Junutula et al. |
| 2009/0018086 A1 | 1/2009 | Doronina et al. |
| 2009/0111756 A1 | 4/2009 | Doronina et al. |
| 2011/0020343 A1 | 1/2011 | Senter et al. |

FOREIGN PATENT DOCUMENTS

| | | |
|---|---|---|
| JP | 2010519310 A | 6/2010 |
| WO | WO-199201047 A1 | 1/1992 |
| WO | WO-9906587 A2 | 2/1999 |
| WO | WO-2002088172 A2 | 2/2003 |
| WO | WO-2004010957 A2 | 2/2004 |
| WO | WO-2004032828 A2 | 4/2004 |
| WO | WO-2007085930 A1 | 8/2007 |
| WO | 2008103693 A2 | 8/2008 |
| WO | WO-2008141044 A2 | 11/2008 |
| WO | WO-2009099741 A1 | 8/2009 |
| WO | WO-2009141240 A1 | 11/2009 |
| WO | WO-2010091150 A1 | 8/2010 |
| WO | WO-2011023883 A1 | 3/2011 |
| WO | WO-2012112708 A1 | 8/2012 |
| WO | WO-2013163229 A1 | 10/2013 |
| WO | WO-2015095227 A2 | 6/2015 |
| WO | WO-2016008112 A1 | 1/2016 |

OTHER PUBLICATIONS

Denis C. Roy et al., "Anti-MY9-Blocked-Ricin: An Immunotoxin for Selective Targeting of Acute Myeloid Leukemia Cells", Blood, vol. 77(11), pp. 2404-2412, 1991.
Ravi V. J. et al., "Immunoconjugates Containing Novel Maytansinoids: Promising Anticancer Drugs", Cancer Reseach, vol. 52, pp. 127-131, 1992.
Lee M. Nadler et al., "B4, A Human B Lymphocyte-Associated Antigen Expressed on Normal, Mitogen-Activated, and Malignant B Lymphocytes", The Journal of Immunology, vol. 131(1), pp. 244-250, 1983.
Denis C. Roy et al., "Elimination of Neuroblastoma and Small-Cell Lung Cancer Cells With an Anti-Neural Cell Adhesion Molecule Immunotoxin", Journal of the National Cancer Institute, vol. 88(16), pp. 1136-1145, 1996.
Jul. 12, 2017, EESR issued in European Patent Application No. 15822852.8.
The First Office Action of Japanese patent application 2017-522709 dated Dec. 4, 2018.

*Primary Examiner* — Kristin A Vajda
(74) *Attorney, Agent, or Firm* — Harness, Dickey & Pierce P.L.C.

(57) ABSTRACT

The present invention relates to linkers, containing amide surrogates with a regular or a novel lysosomal enzymatic cleavable dipeptidic unit, to connect cytotoxic drugs to antibodies. The present invention also relates to ADCs (antibody-drug conjugates) derived from these amide surrogate linkers for the treatment of cancers.

29 Claims, 7 Drawing Sheets

LINKERS AND THEIR APPLICATION TOWARDS ADC

CROSS-REFERENCE TO RELATED APPLICATIONS

This application is a National Stage of International Application No. PCT/CN2015/083840, filed on Jul. 13, 2015 and published in English as WO 2016/008392 on Jan. 21, 2016. This application claims the priority to International Application No. PCT/CN2014/082292, filed on Jul. 16, 2014. The entire disclosures of the above applications are incorporated herein by reference.

FIELD OF THE INVENTION

The present invention relates to linkers, containing amide surrogates with a regular or a novel lysosomal enzymatic cleavable dipeptidic unit, to connect cytotoxic drugs to antibodies. The present invention also relates to ADCs (antibody-drug conjugates) derived from these amide surrogate linkers for the treatment of cancers.

BACKGROUND OF THE INVENTION

Antibody drug conjugates (ADCs) hold the promise as a target specific and effective treatment for a number of diseases e.g. bacterial infection and cancers, but at the same time with an improved systemic side effect profile.

The concept to combine a target specific antibody with a cytotoxic compound is very simple and elegant. An antibody is well known for its ability to recognize an antigen in specific manner and the often insufficient cell killing activity following an immune response, limited its therapeutic potential. On the other hand, cyctotoxic compounds are widely used in the treatment of cancers and their effectiveness are hindered by non-specific systemic adverse events associated with higher dose usage. The combination of an antibody with a cyctoxic compound can therefore lead to a therapeutic agent with enhancing efficacy to the antibody and reduced systemic side effects to the cytotoxic drug, attributing to the target specific delivery by the antibody and minimize of normal tissues from drug exposures.

One of the keys to the success of ADCs relies on the identification of suitable linkers that are stable during circulation in the blood stream, but rapidly cleave to release the cytotoxic compound at the target for cell killing activity. A demonstrated successful example is the linker, such as the one in Adcertris, which incorporates a lysosomal enzymatic cleavable peptide component. The C-terminal amide bond in this part of the linker that can be easily cleaved at target cells by lysosomal enzymes is essential to the drug releasing mechanism. Other amide bonds on the linker if undergo prematurely cleavage may lead to undesirable side effects (Formular B-1).

(B-1)

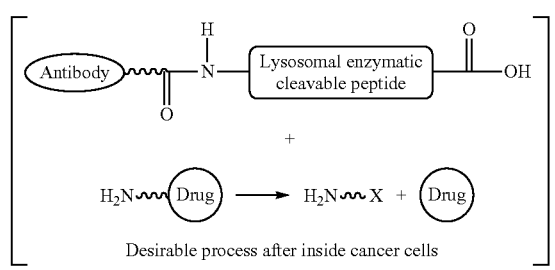

Desirable process after inside cancer cells

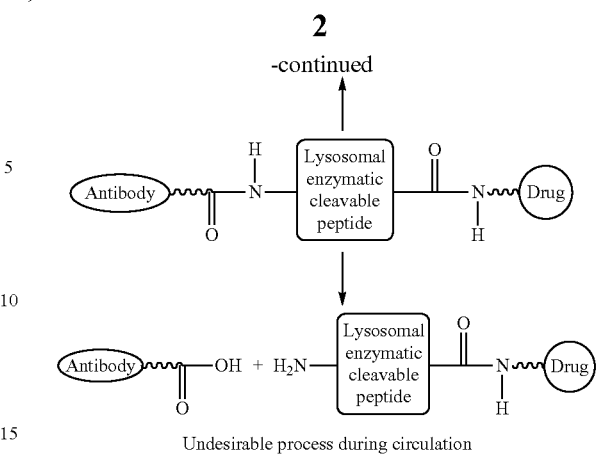

Undesirable process during circulation

This application describes the replacement of the N-terminal amide bond of the lysosomal enzymatic cleavable peptide with an amide surrogate (Formullar B-2). This modification can further improved stability of the resulting ADCs in circulation.

(B-2)

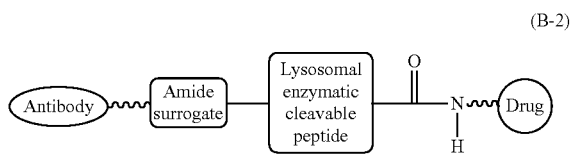

DESCRIPTION OF THE INVENTION

The present invention provides a linker of formula (I) to connect drugs to antibodies,

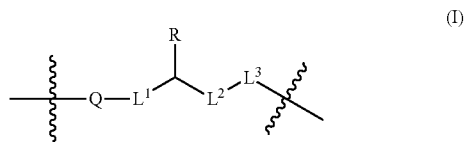

(I)

wherein,
R is selected from the group consisting of $CF_2H$, $CF_3$, $CF_2CF_3$, and $PhSO_2Me$;
Q is selected from the group consisting of

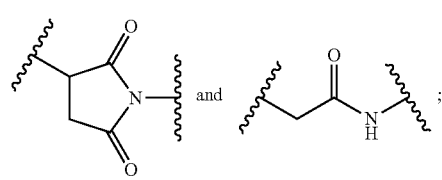 [SMILES: *C1CC(=O)N(*)C1=O ; *CC(=O)N*]

$L^1$ is selected from the group consisting of —$(CR^1R^2)_m$—$(CR^3R^4)$—$(CR^1R^2)_n$—, —$(CR^1R^2)_m$—$(CR^3R^4)$—O—$(CR^1R^2)_n$—, and —$[(CR^1R^2)(CR^1R^2)X]_p$—$(CR^1R^2)_q$—;
m is 1, 2, 3, or 4;
n is 1, 2, 3, or 4;
p is 1, 2, 3, 4, 5, or 6;
q is 1 or 2;
$R^1$ is selected from the group consisting of H and $C_{1-3}$ alkyl optionally substituted with 1, 2 or 3 of substituents independently selected from the group consisting of halogen, OH, NH$_2$, NHMe, and NMe$_2$.

R$^2$ is selected from the group consisting of H and C$_{1-3}$ alkyl optionally substituted with 1, 2 or 3 of substituents independently selected from the group consisting of halogen, OH, NH$_2$, NHMe, and NMe$_2$;

R$^3$ is selected from the group consisting of H and C$_{1-3}$ alkyl optionally substituted with 1, 2 or 3 of substituents independently selected from the group consisting of halogen, OH, NH$_2$, NHMe, and NMe$_2$;

R$^4$ is selected from the group consisting of H, C$_{1-3}$ alkyl, OH, NR$^5$R$^6$, CO$_2$H, P(O)(OH)$_2$, and SO$_3$H, said C$_{1-3}$ alkyl is optionally substituted with 1, 2 or 3 of substituents independently selected from the group consisting of halogen, OH, NH$_2$, NHMe, and NMe$_2$;

R$^5$ is selected from the group consisting of H and C$_{1-3}$ alkyl optionally substituted with 1, 2 or 3 of substituents independently selected from the group consisting of halogen, OH, NH$_2$, NHMe, and NMe$_2$;

R$^6$ is selected from the group consisting of H and C$_{1-3}$ alkyl optionally substituted with 1, 2 or 3 of substituents independently selected from the group consisting of halogen, OH, NH$_2$, NHMe, and NMe$_2$;

X is selected from the group consisting of NR$^7$, O, S(O)$_r$;

r is 0, 1, or 2;

R$^7$ is selected from the group consisting of H and C$_{1-3}$ alkyl optionally substituted with 1, 2 or 3 of substituents independently selected from the group consisting of halogen, OH, NH$_2$, NHMe, and NMe$_2$;

L$^2$ is a di-peptide unit selected from

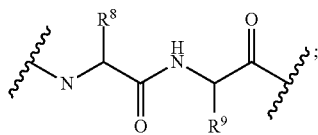

R$^8$ is selected from the group consisting of methyl, propyl, isopropyl, sec-butyl, benzyl, and

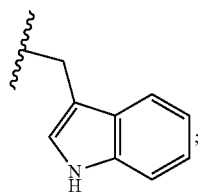 [SMILES: *Cc1c[nH]c2ccccc12]

R$^9$ is selected from the group consisting of (CH$_2$)$_4$NH$_2$, (CH$_2$)$_3$NHCONH$_2$, (CH$_2$)$_3$NHC(=NH)NH$_2$,

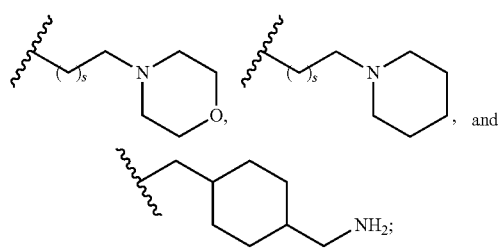

s is 0, 1, 2, 3, or 4;

L$^3$ is a self-immolative unit selected from the group consisting of

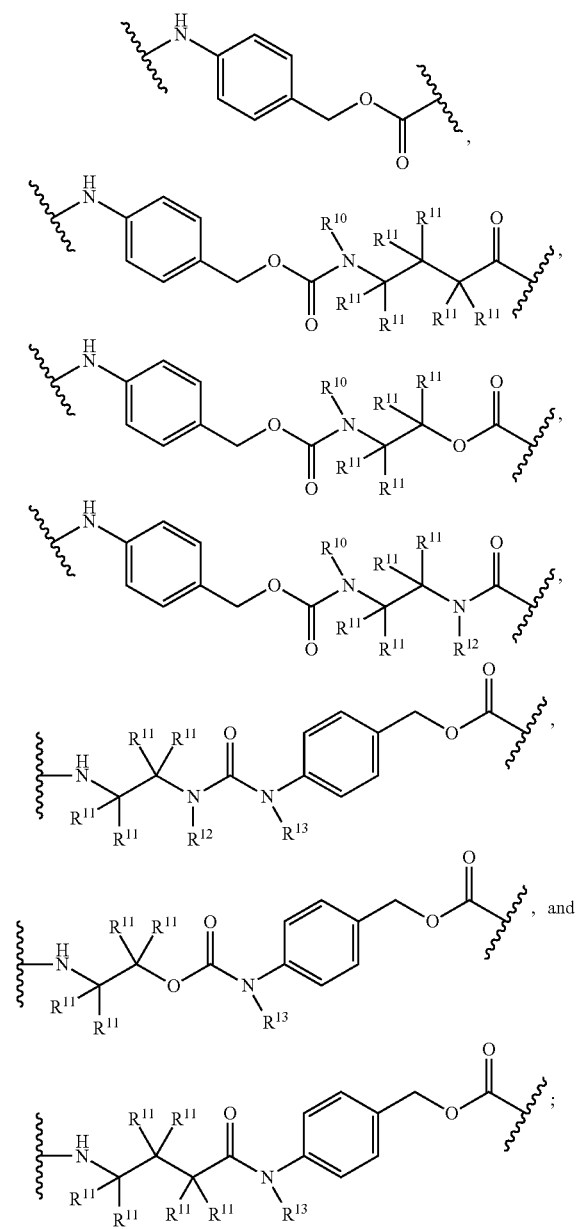

R$^{10}$ is selected from the group consisting of H and C$_{1-3}$ alkyl optionally substituted with 1, 2 or 3 of substituents independently selected from the group consisting of halogen, OH, NH$_2$, NHMe, and NMe$_2$;

each R$^{11}$ is independently selected from the group consisting of H and C$_{1-3}$ alkyl optionally substituted with 1, 2 or 3 of substituents independently selected from the group consisting of halogen, OH, NH$_2$, NHMe, and NMe$_2$;

two geminal R$^{11}$ may be optionally joined together to form a 3-6 membered ring with a carbon atom to which they are attached;

two adjacent R$^{11}$ may be optionally joined together to form a 5-7 membered ring with a carbon atom to which they are attached;

R$^{12}$ is selected from the group consisting of H and C$_{1-3}$ alkyl optionally substituted with 1, 2 or 3 of substituents independently selected from the group consisting of halogen, OH, $NH_2$, NHMe, and $NMe_2$; and $R^{13}$ is selected from the group consisting of H and $C_{1-3}$ alkyl optionally substituted with 1, 2 or 3 of substituents independently selected from the group consisting of halogen, OH, $NH_2$, NHMe, and $NMe_2$.

The present invention also provides a drug-linker conjugate of formula (II),

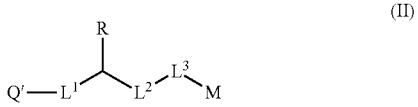

(II)

wherein,
Q' is selected from the group consisting of

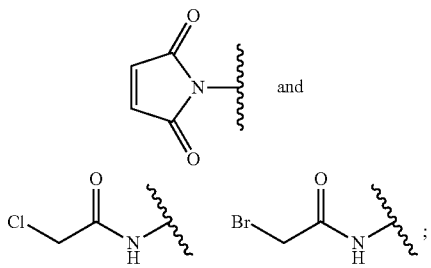

M is a drug; and
other variables are as defined above.

The present invention also provides an ADC of formula (III),

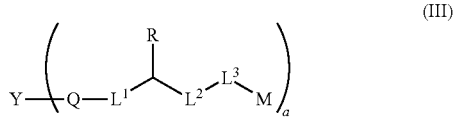

(III)

wherein,
Y is an antibody;
a is an integer or decimal selected from 1-8;
M is a drug; and
other variables are as defined in above.

In certain embodiment of this invention, a is 1, 2, 3, 3.4, 3.5, 4, 4.2, 5, 6, 7, or 8.

In certain embodiment of this invention, the aforesaid antibody is selected from the group consisting of a resurfaced monoclonal antibody, a resurfaced single chain monoclonal antibody, or a resurfaced monoclonal antibody fragment that preferentially binds to a target cell.

In certain embodiment of this invention, the aforesaid antibody is selected from the group consisting of a humanized monoclonal antibody, a humanized single chain monoclonal antibody, or a humanized monoclonal antibody fragment.

In certain embodiment of this invention, the aforesaid antibody is selected from the group consisting of a chimeric antibody, a chimeric antibody fragment, a domain antibody, or a domain antibody fragment thereof.

In certain embodiment of this invention, the aforesaid antibody is selected from the group consisting of MY9, anti-B4, EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptors, EphB receptors, EGFR, EGFRvIII, HER2, HER3, mesothelin, cripto, $alpha_vbeta_3$, $alpha_vbeta_5$, $alpha_vbeta_6$ integrin or C242.

In certain embodiment of this invention, the aforesaid antibody is selected from the group consisting of My9-6, B4, C242, N901, DS6, EphA2 receptor, CD38, IGF-IR, CNTO 95, B-B4, Trastuzumab, Tertuzumab, Bevatuzumab, Sibrotuzumab, Rituximab, and Adalimumab.

In certain embodiment of this invention, the aforesaid antibody is selected from the group consisting of Herceptin and Erbitux.

In certain embodiment of this invention, the aforesaid antibody binds to target cells selected from tumor cells; virus infected cells, microorganism infected cells, parasite infected cells, autoimmune cells, activated cells, myeloid cells, activated T-cells, B cells, or melanocytes; cells expressing one or more of IGF-IR, CanAg, EGFR, MUCI, MUCI 6, VEGF, TF, MY9, anti-B4, EpCAM, CD2, CD3, CD4, CD5, CD6, CD11, CD11a, CD18, CD19, CD20, CD22, CD26, CD30, CD33, CD37, CD38, CD40, CD44, CD56, CD70, CD79, CD105, CD138, EphA receptors, EphB receptors, EGFRvIII, HER2/neu, HER3, mesothelin, cripto, $alpha_vbeta_3$ integrin, $alpha_vbeta_5$ integrin, $alpha_vbeta_6$ integrin, Apo2, and C242 antigens; or cells expressing insulin growth factor receptor, epidermal growth factor receptor, and folate receptor.

In certain embodiment of this invention, the aforesaid tumor cells are selected from breast cancer cells, prostate cancer cells, ovarian cancer cells, colorectal cancer cells, gastric cancer cells, squamous cancer cells, small-cell lung cancer cells, and testicular cancer cells.

In certain embodiment of this invention, the aforesaid drug is a cytotoxic drug.

In certain embodiment of this invention, the aforesaid drug is selected from the group consisting of maytansinoid, DNA-binding drug and its analog, calicheamicin, doxorubicin and its analog, vinca alkaloid, cryptophycin, dolastatin, auristatin and analog thereof, tubulysin, epothilone, taxoid and siRNA.

In certain embodiment of this invention, the aforesaid DNA-binding drug is CC-1065.

In certain embodiment of this invention, the aforesaid M is selected from the group consisting of:

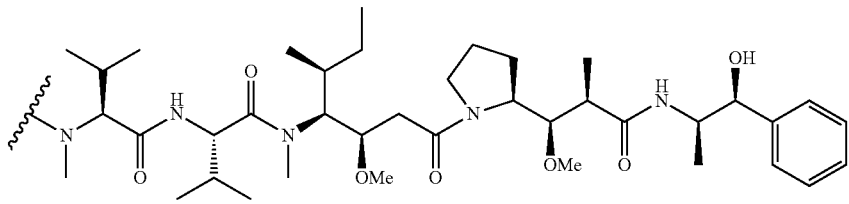

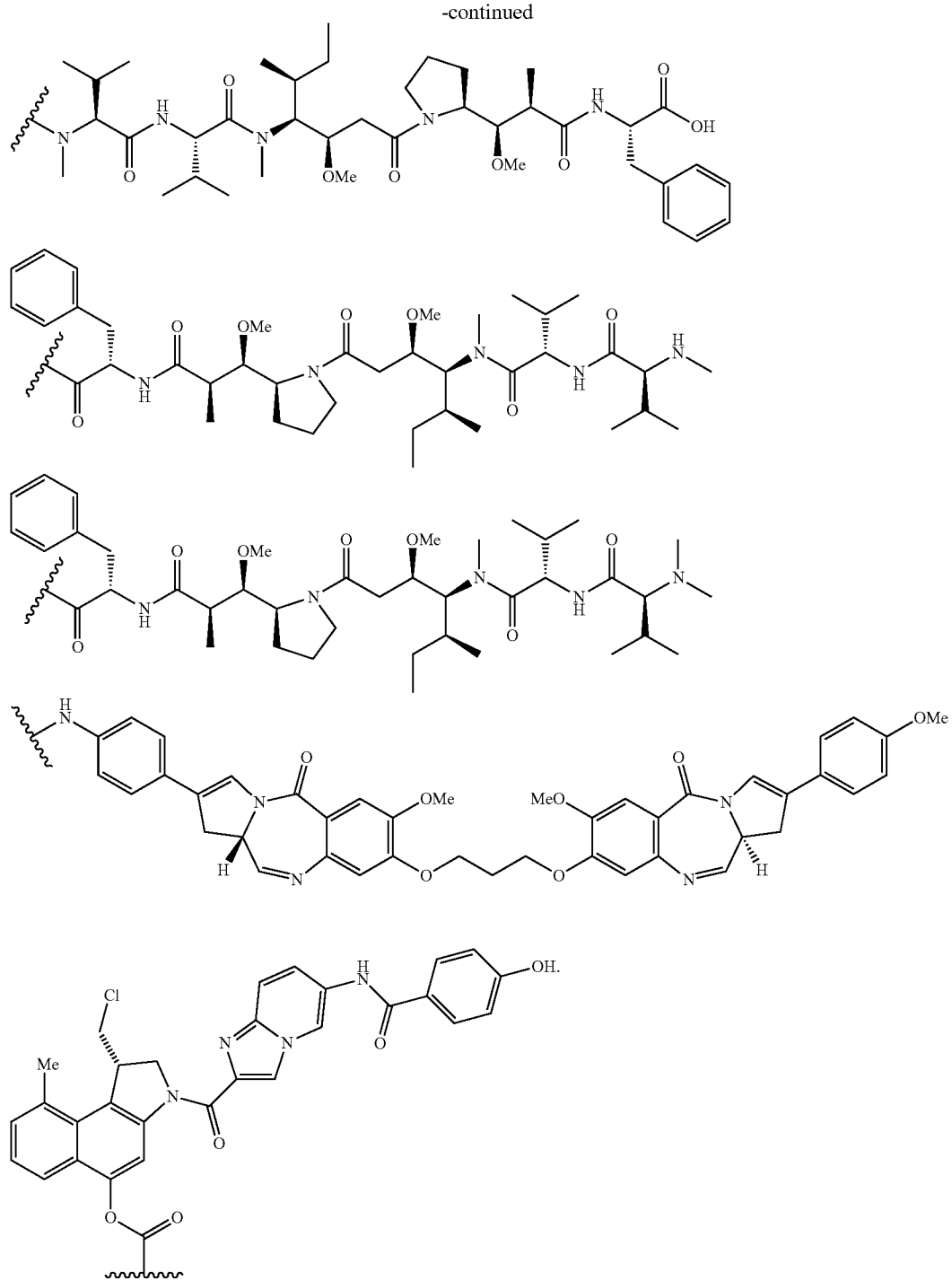

In certain embodment of this invention, the aforesaid drug is a diagnostic or detection reagen.

In certain embodment of this invention, the aforesaid drug is a radio-labeled compound.

In certain embodment of this invention, the aforesaid drug is labeled with $^{3}$H, $^{18}$F, $^{11}$C, $^{13}$N, $^{15}$O, $^{201}$Tl, $^{32}$P, $^{51}$Cr, $^{67}$Ga, $^{123}$I, $^{125}$I, $^{131}$I, $^{132}$I, $^{131}$Cs, $^{113}$Xe, $^{133}$Xe, $^{169}$Yb, $^{198}$Au, $^{203}$Hg, $^{99m}$Tc, $^{113m}$In, $^{133m}$In, $^{75}$Se, $^{186}$Re, $^{153}$Sm, and $^{89}$Sr.

In certain embodment of this invention, the aforesaid $L^{1}$ is selected from the group consisting of:

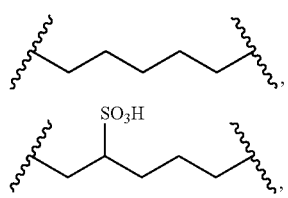

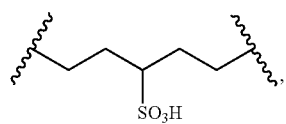
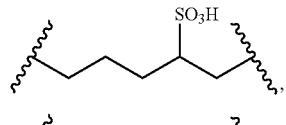
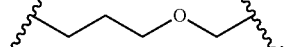
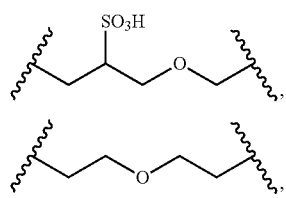
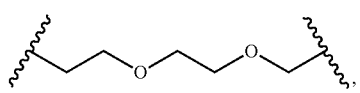
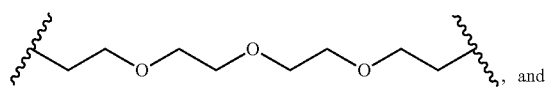
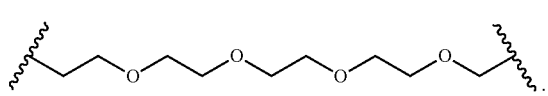
In certain embodment of this invention, the aforesaid $L^2$ is selected from the group consisting of:
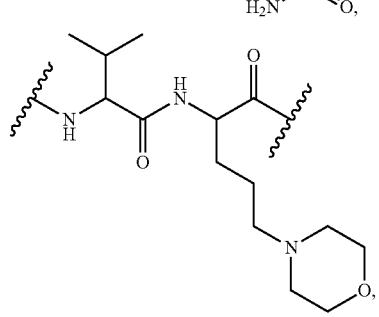
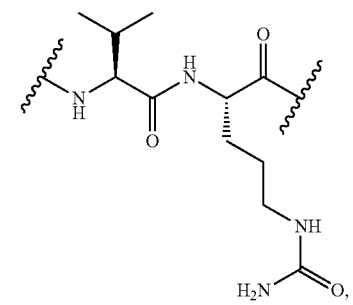
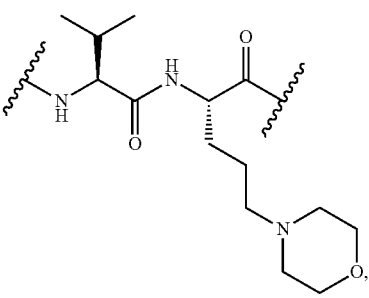
, and
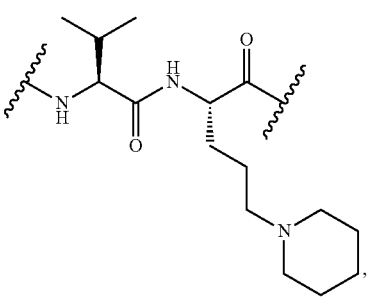
In certain embodment of this invention, the aforesaid $L^2$ is selected from the group consisting of:
Val-Cit
DP1
DP2

-continued

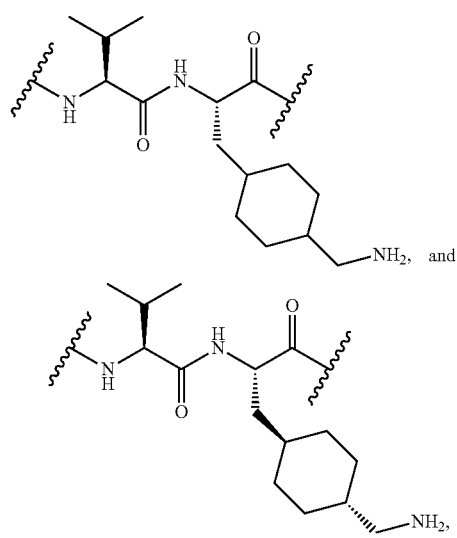

DP3

In certain embodiment of this invention, the aforesaid ring formed by two geminal $R^{11}$ or two adjacent $R^{11}$ is cyclohexyl.

In certain embodiment of this invention, the aforesaid $L^3$ is selected from the group consisting of:

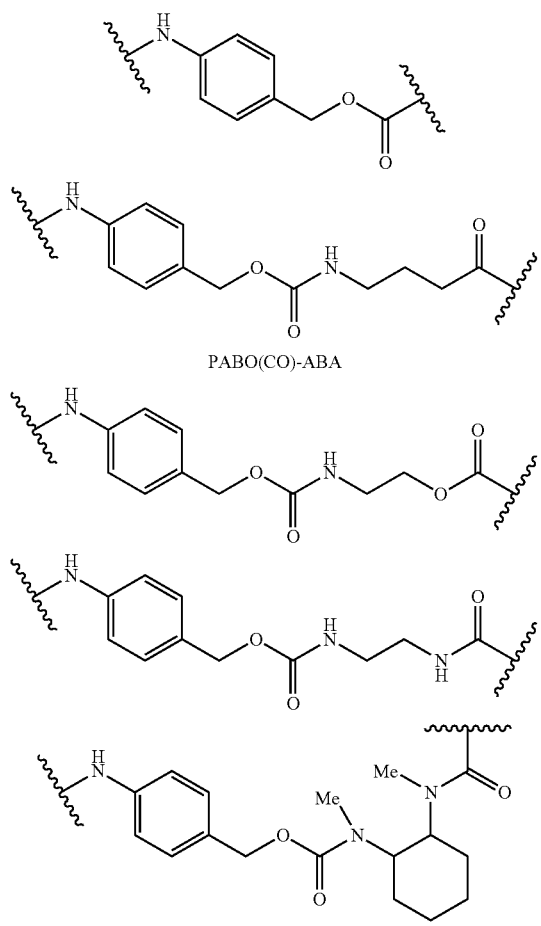

-continued

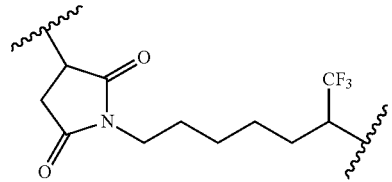

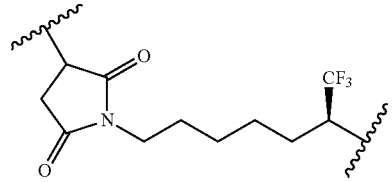

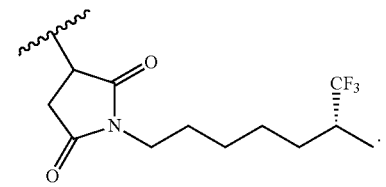

ABA-PABO(CO)

In certain embodiment of this invention, the aforesaid moiety of

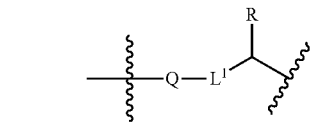

is selected from the group consisting of:

In certain embodiment of this invention, the aforesaid moiety of

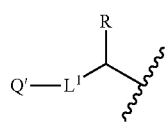
is selected from the group consisting of:
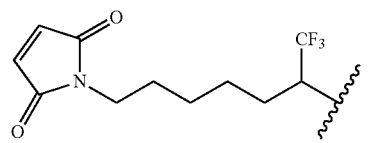
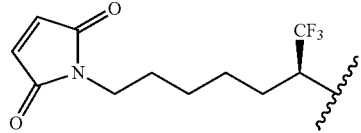
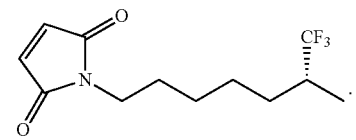
In certain embodiment of this invention, the aforesaid linker is selected from the group consisting of:
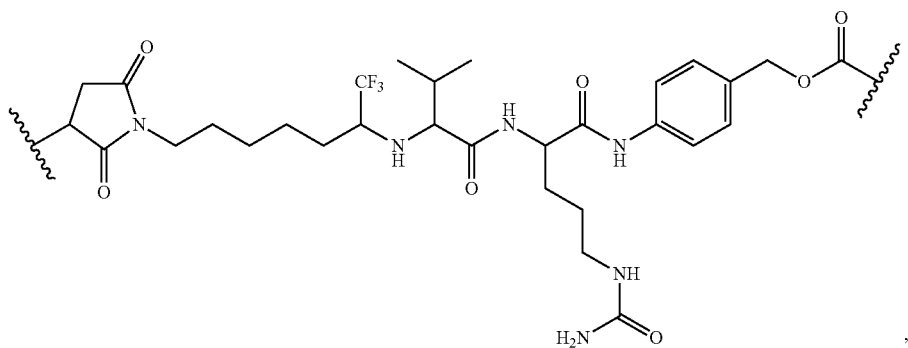
,
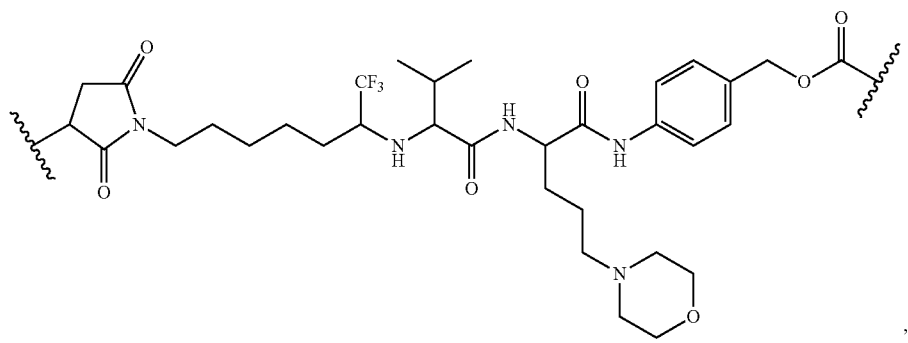
,
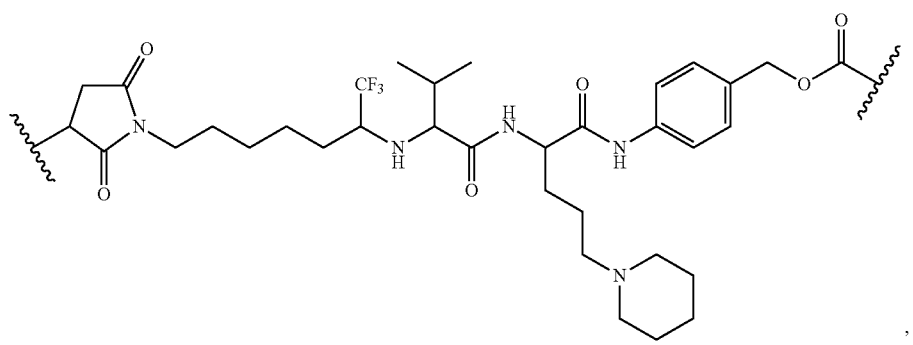
,

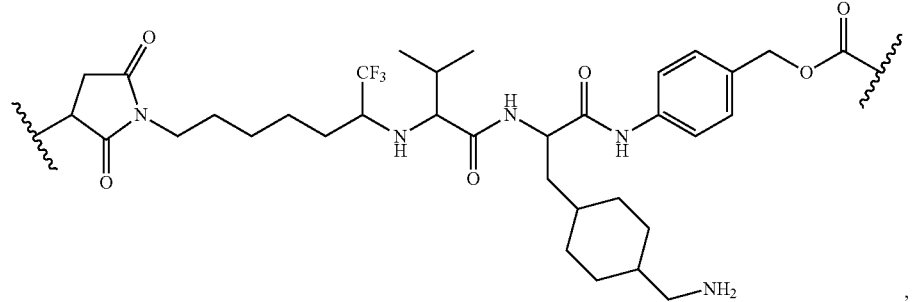
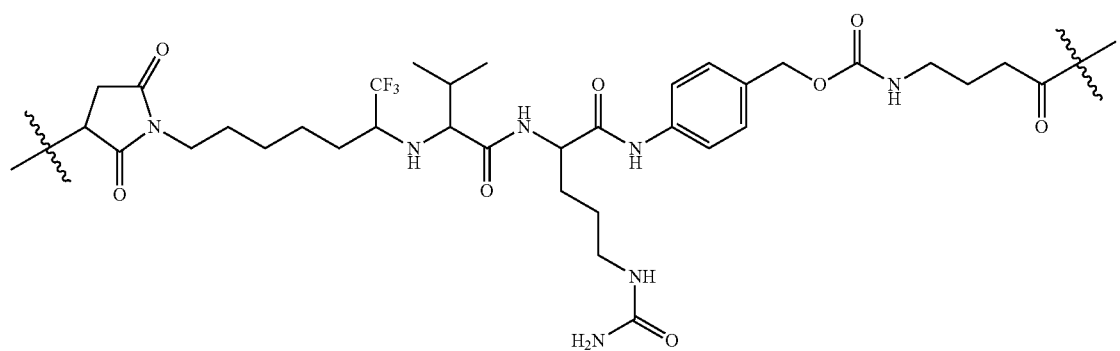
, and
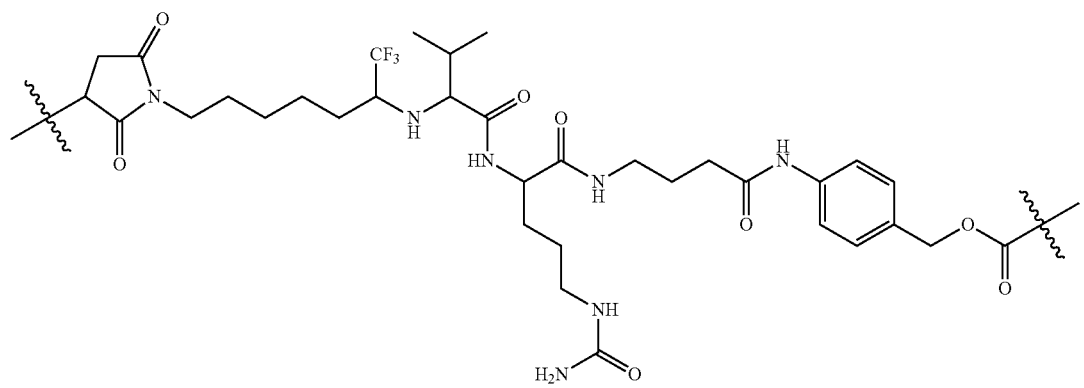
In certain embodment of this invention, the aforesaid linker is selected from the group consisting of:
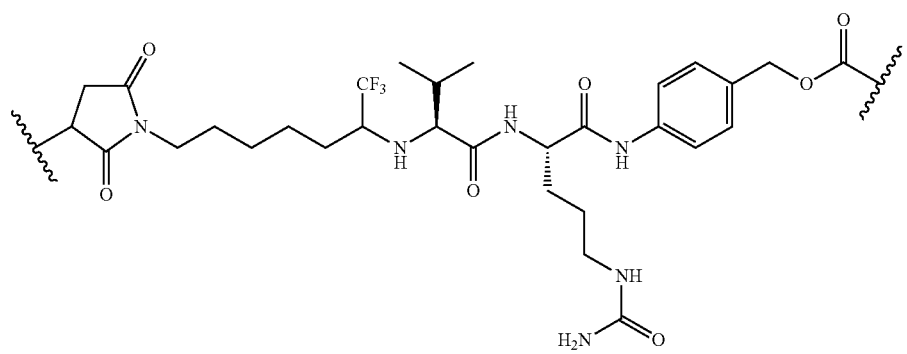
,

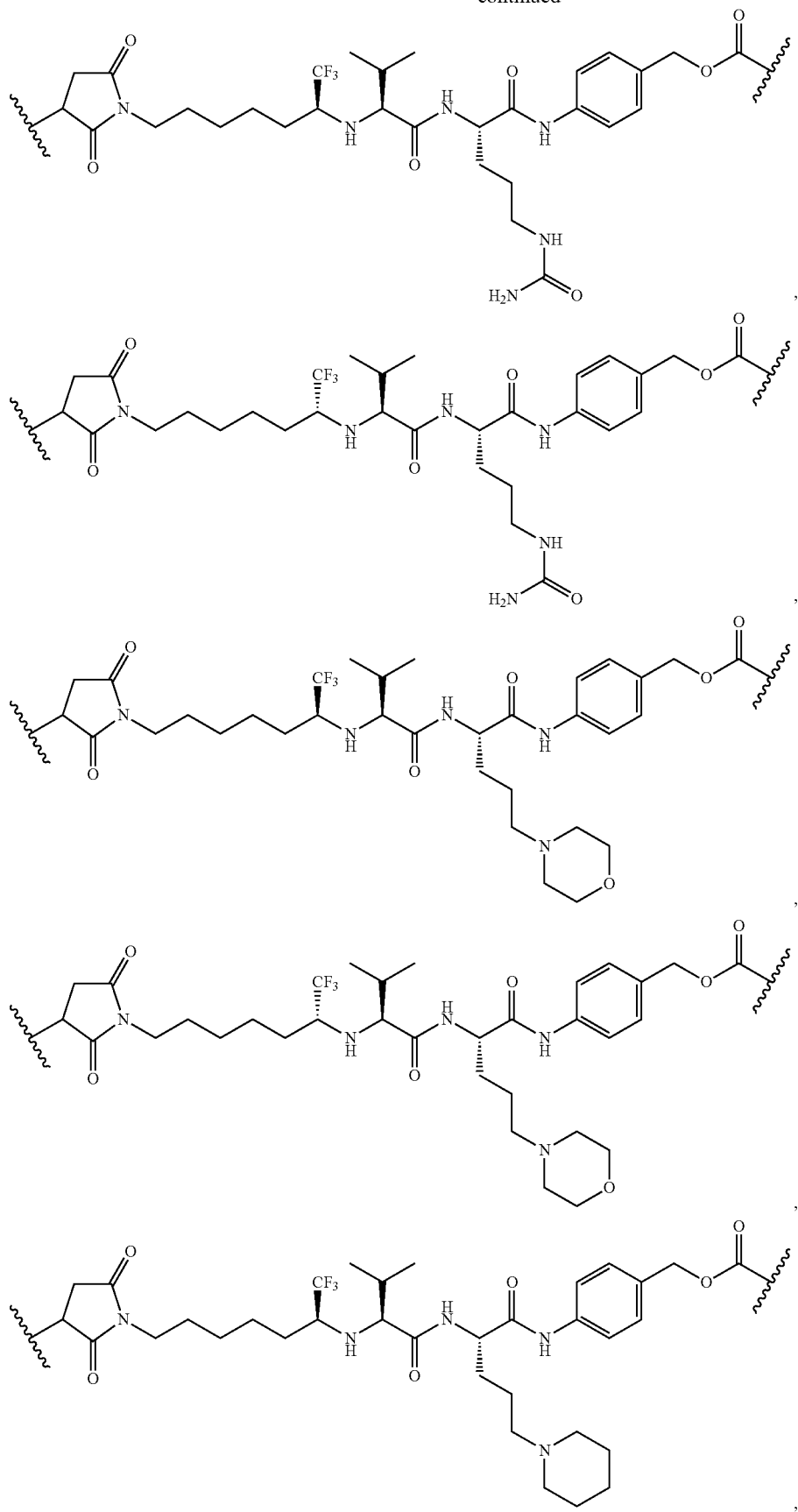

-continued
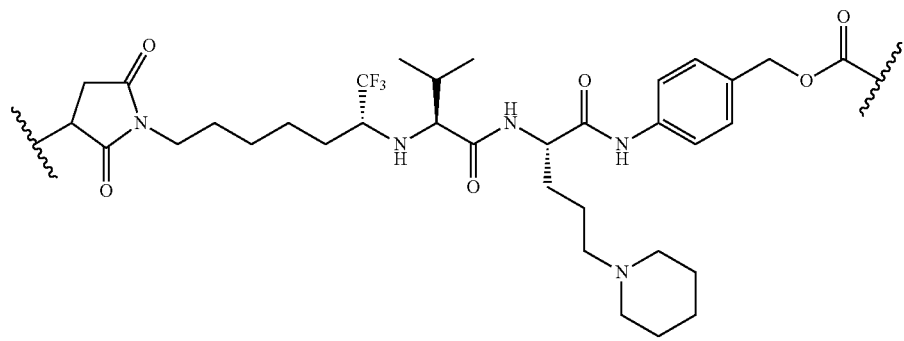
,
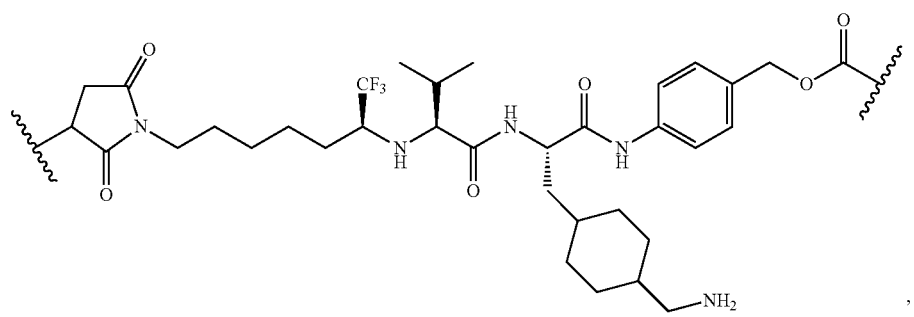
,
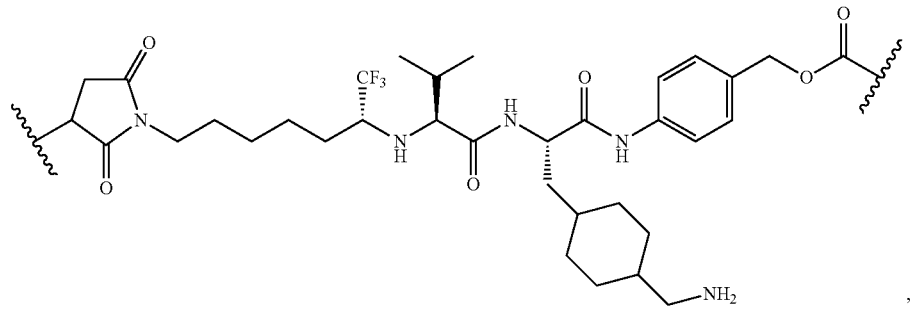
,
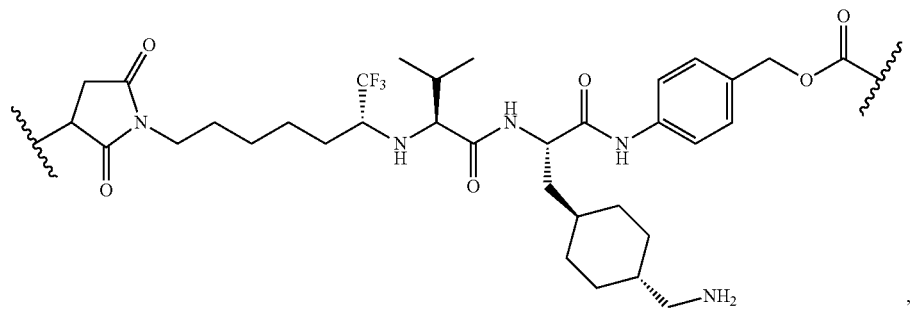
,
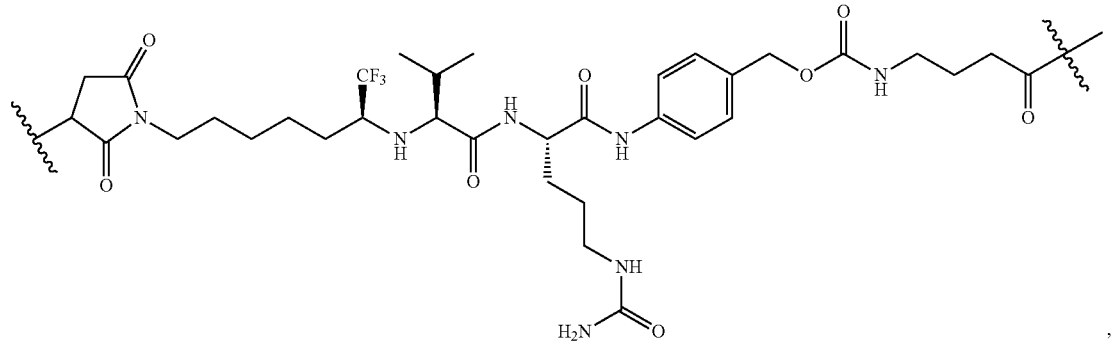
, and

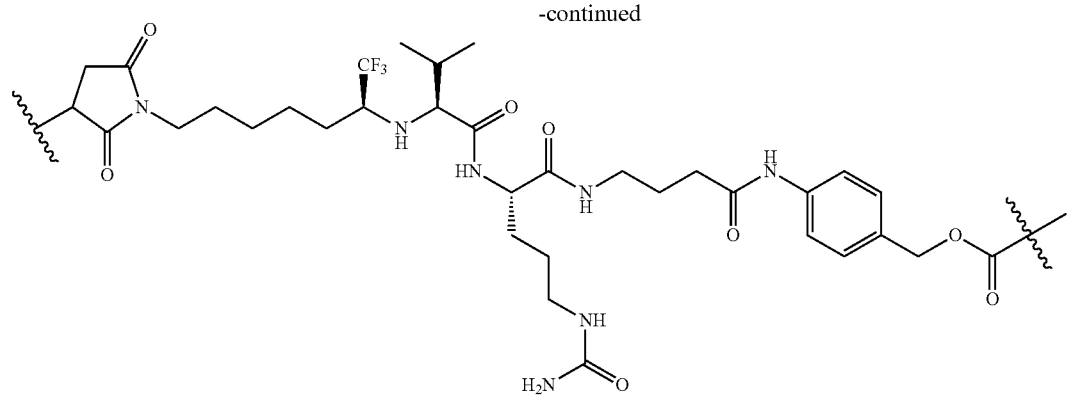
In certain embodment of this invention, the aforesaid conjugate is selected from the group consisting of:
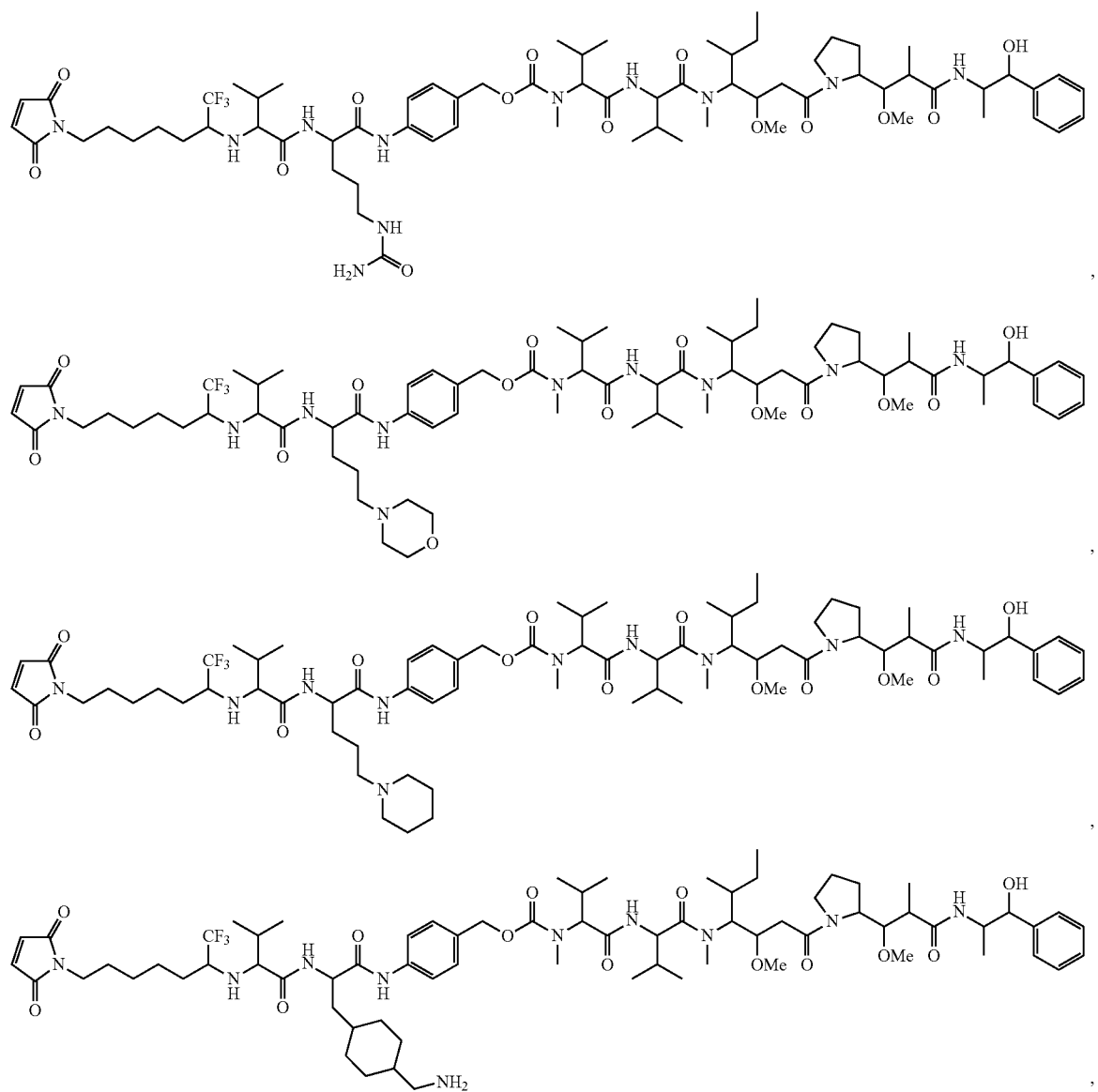

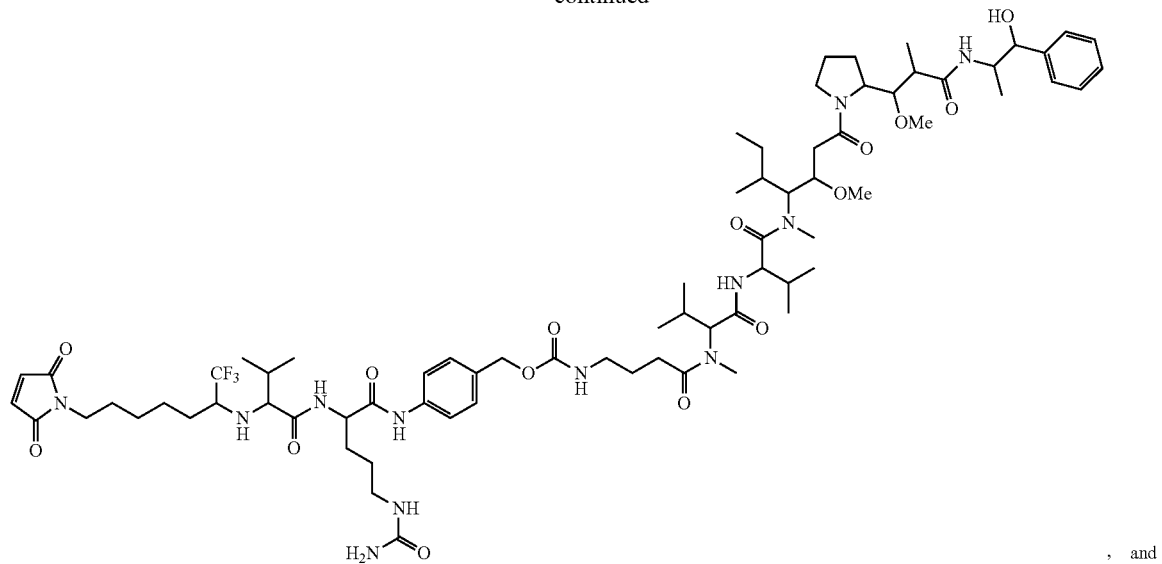
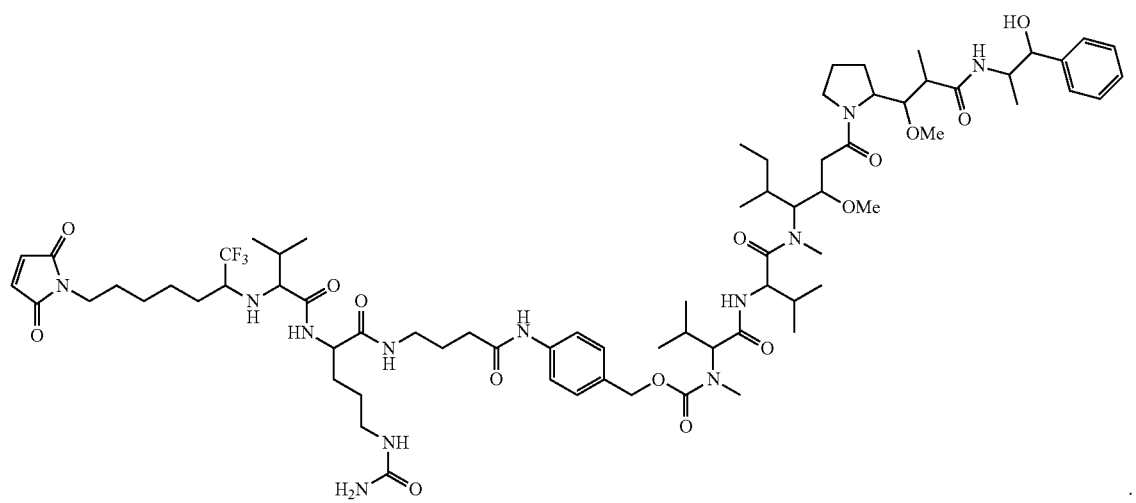
In certain embodment of this invention, the aforesaid conjugate is selected from the group consisting of:
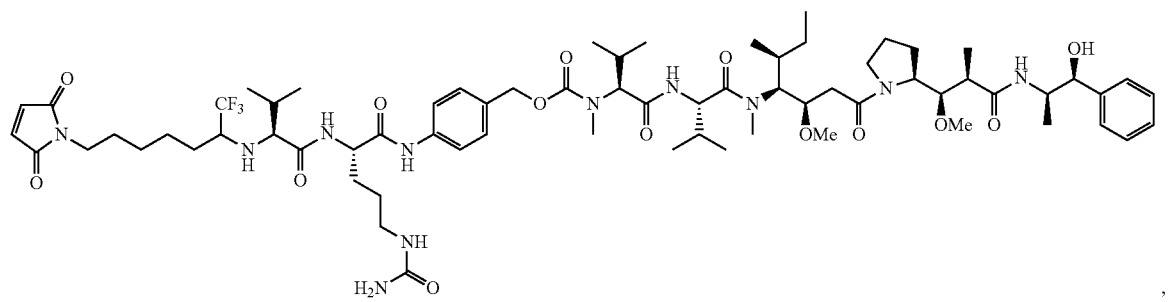

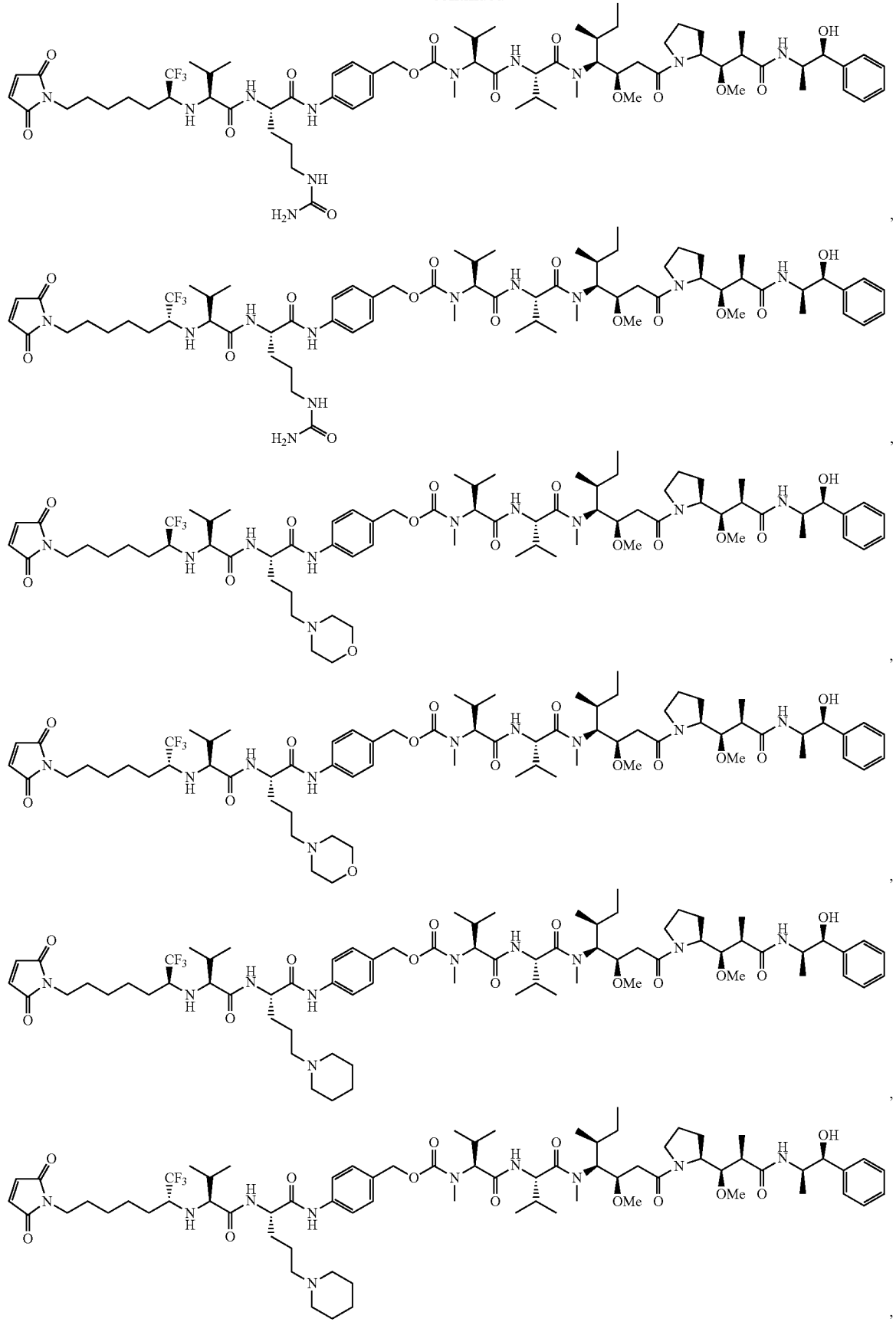

-continued
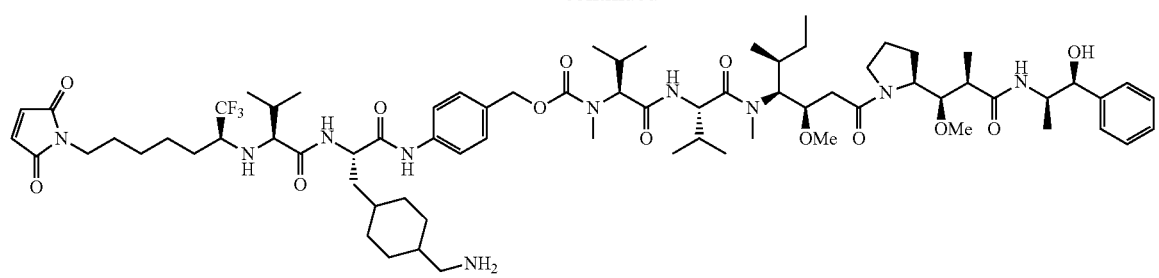
,
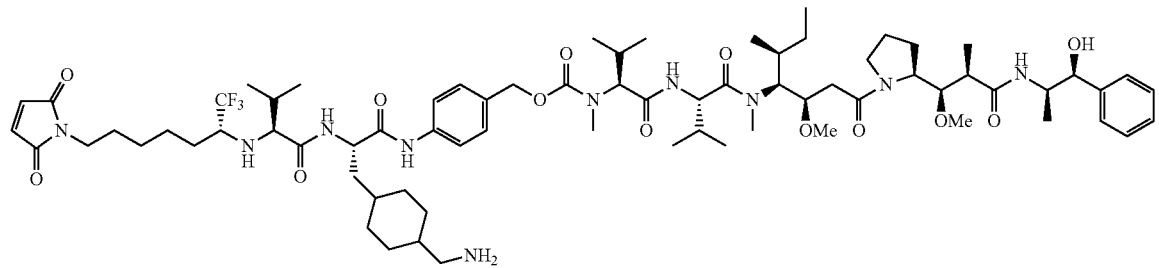
,
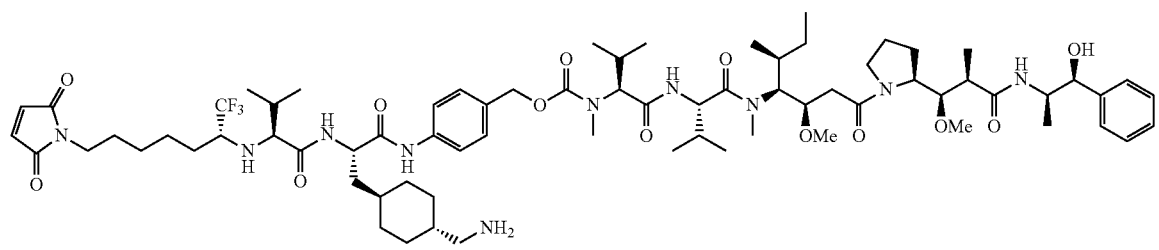
,
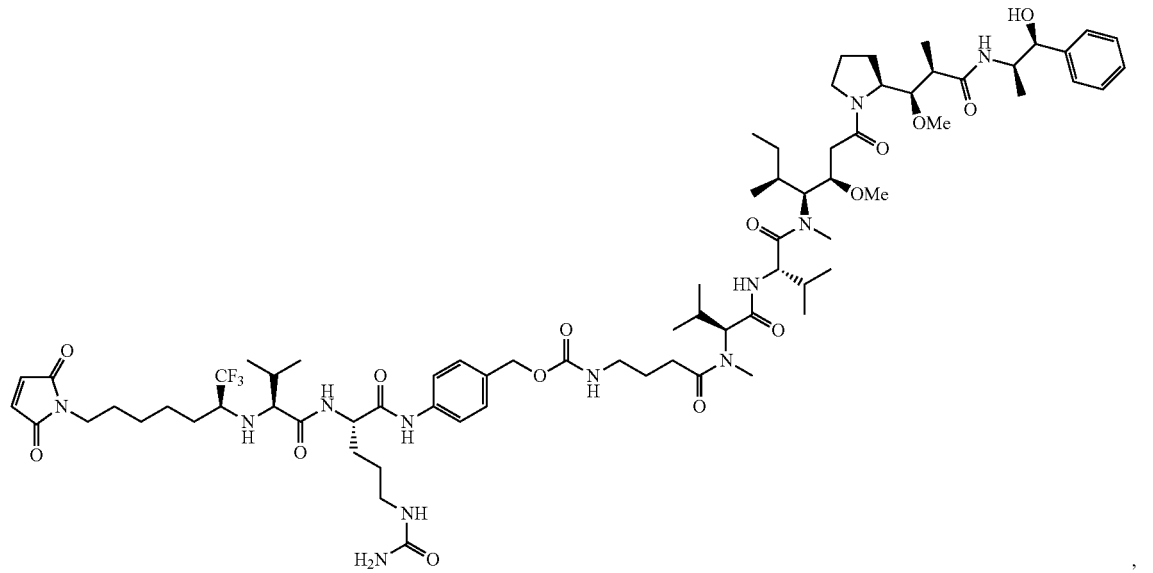
, and

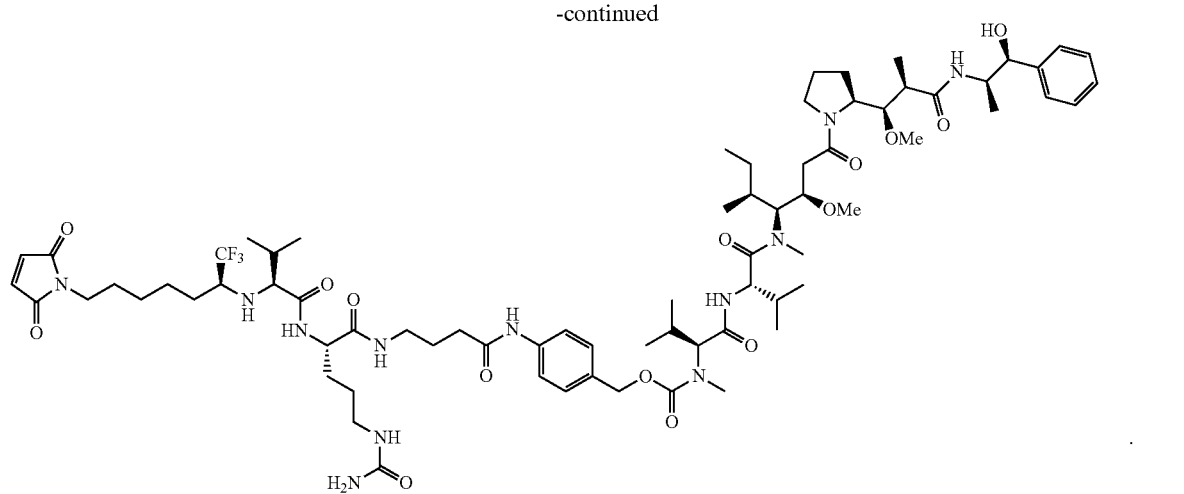
In certain embodment of this invention, the aforesaid ADC is selected from the group consisting of:
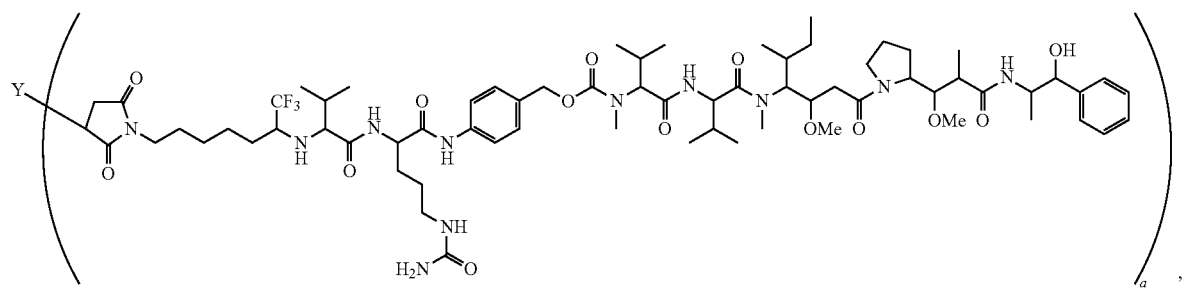
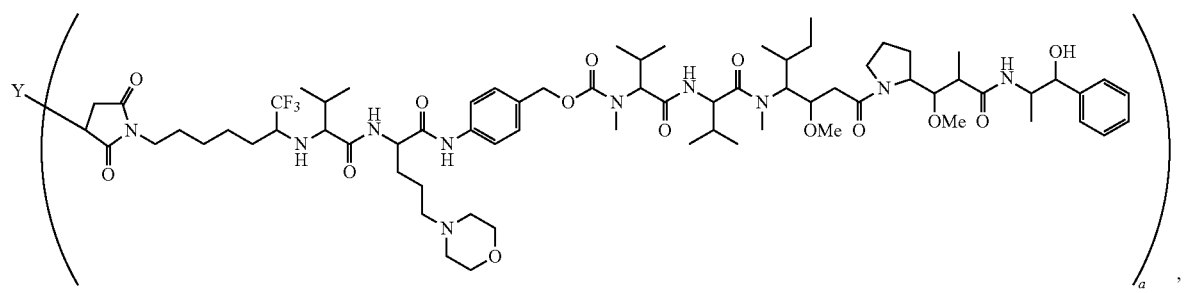
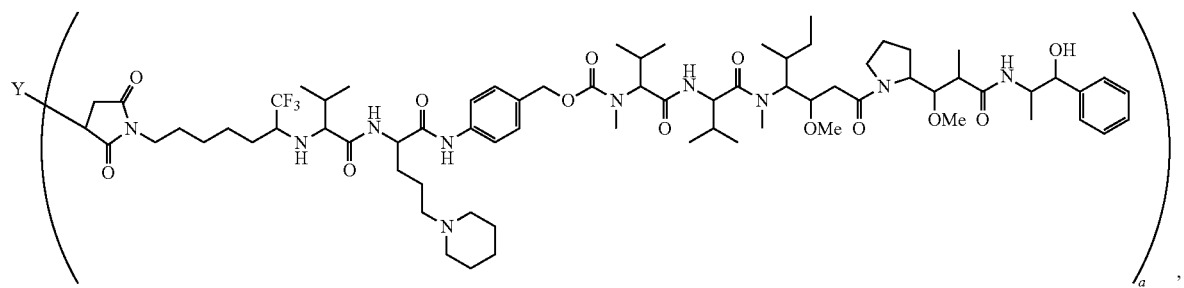

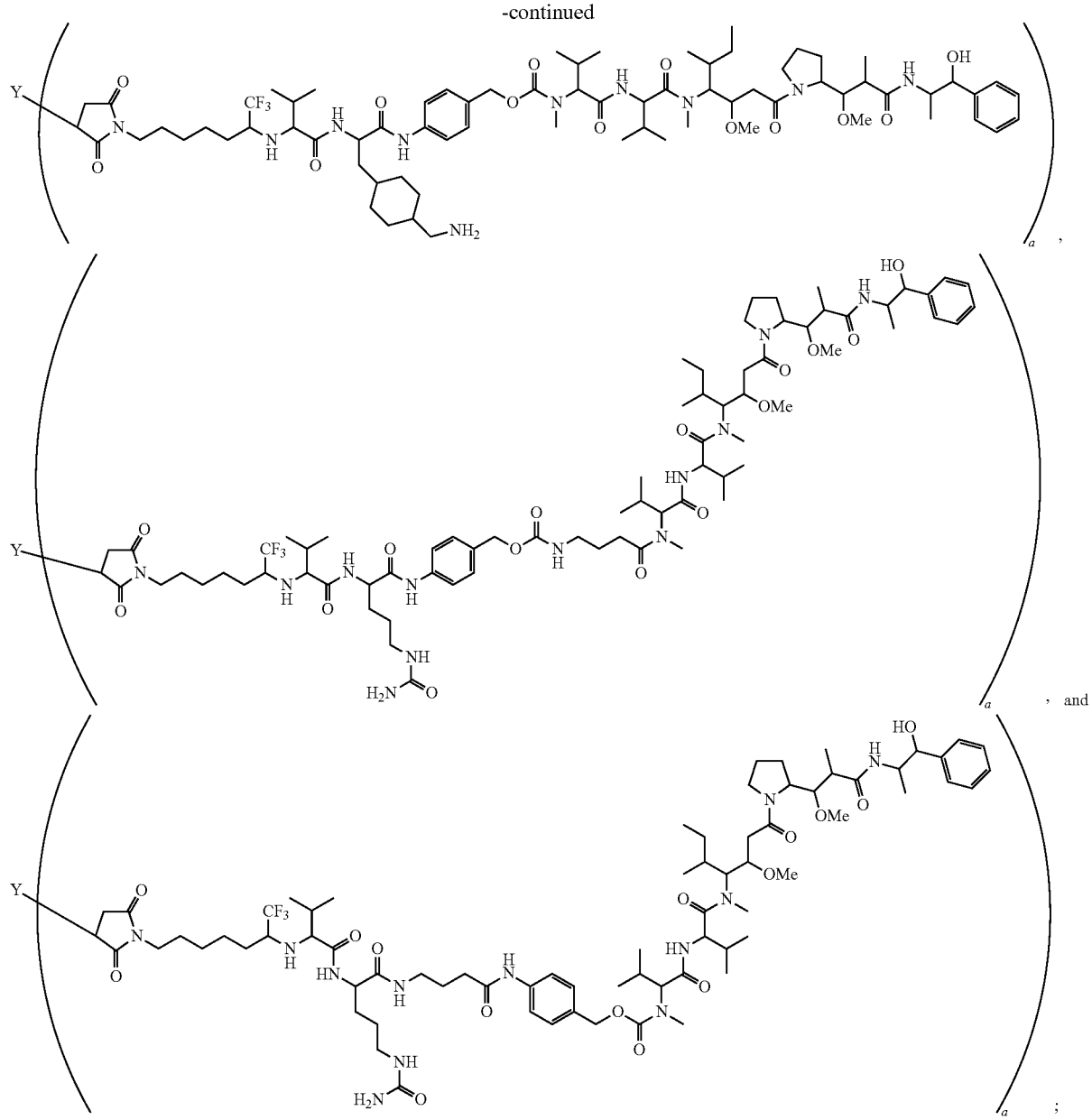
Y is an antibody, a is an integer or decimal selected from 1-8, concretely a is 1, 2, 3, 3.4, 3.5, 4, 4.2, 5, 6, 7, or 8.
In certain embodment of this invention, the aforesaid ADC is selected from the group consisting of:
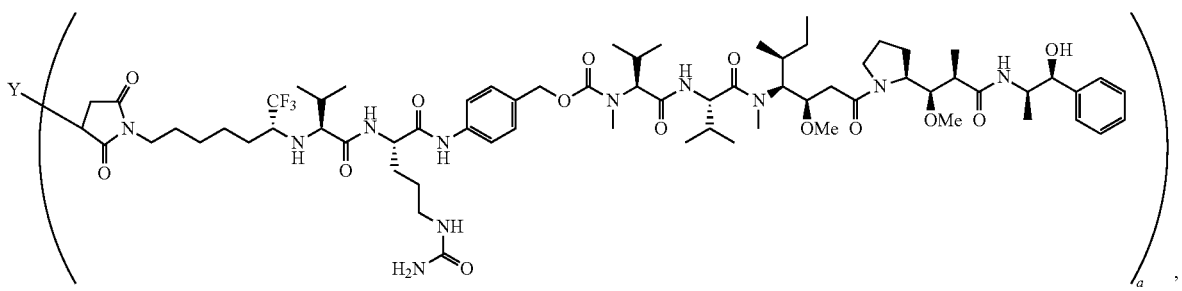

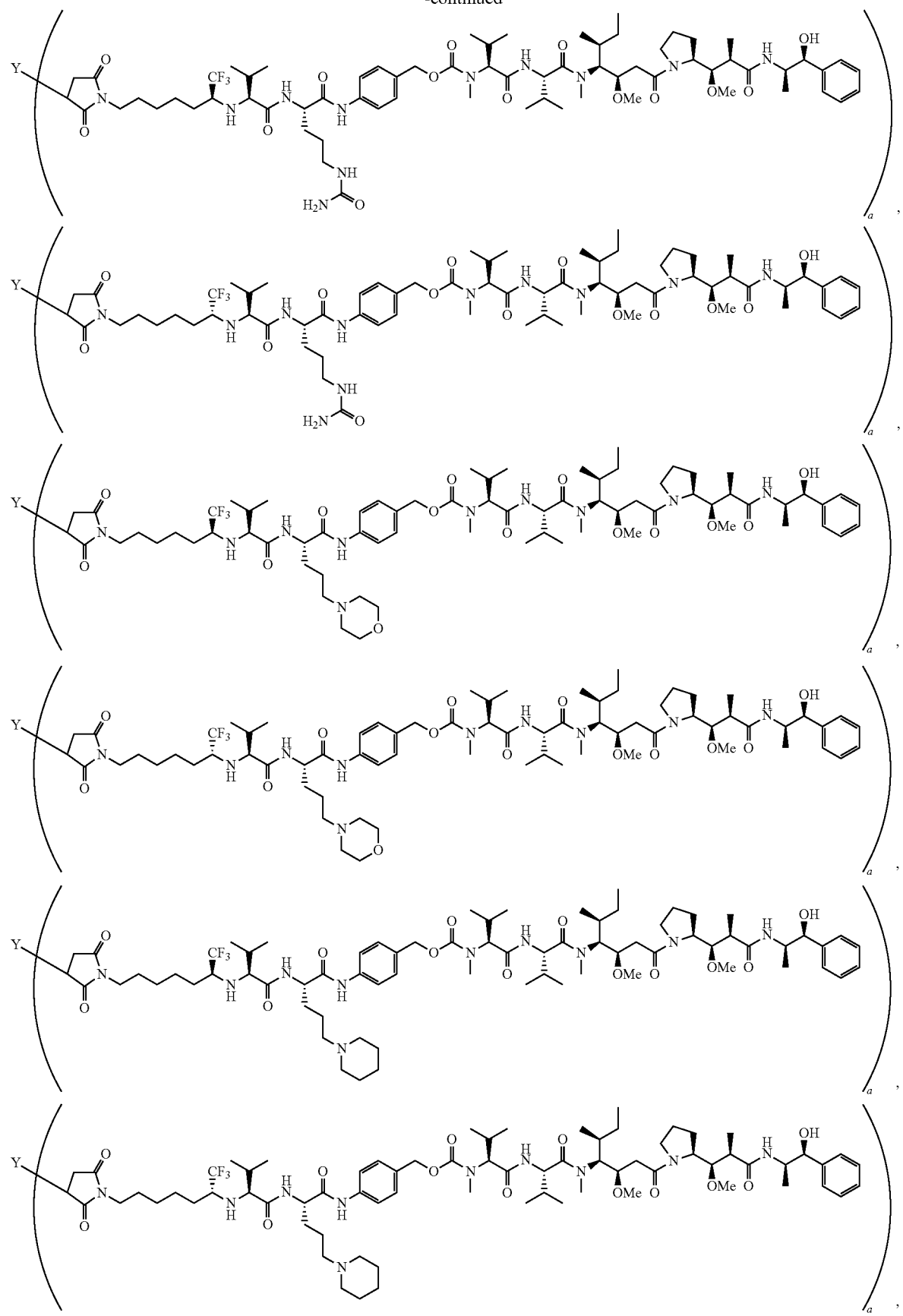

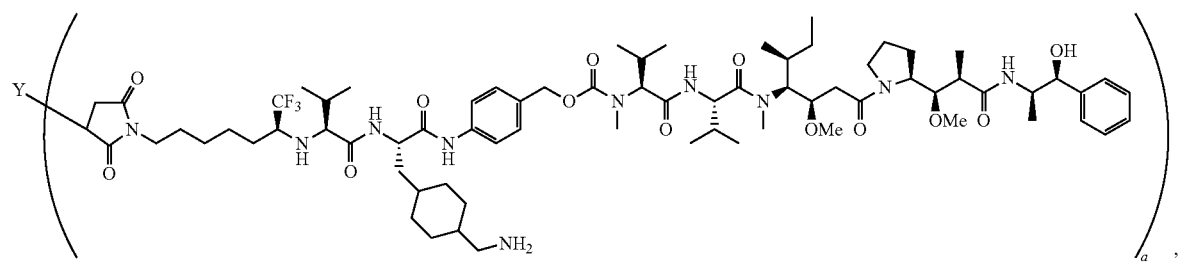
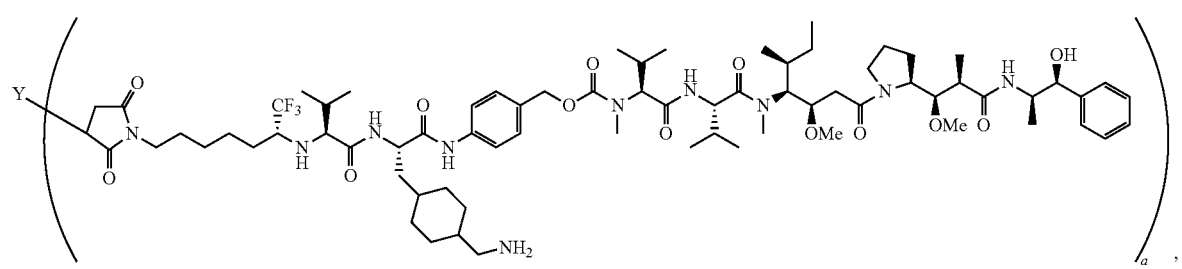
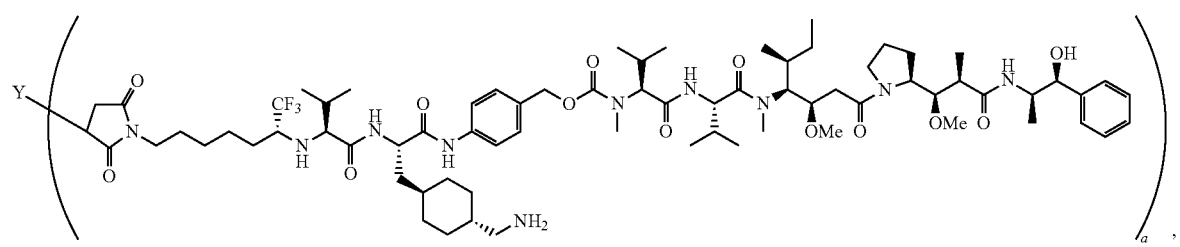
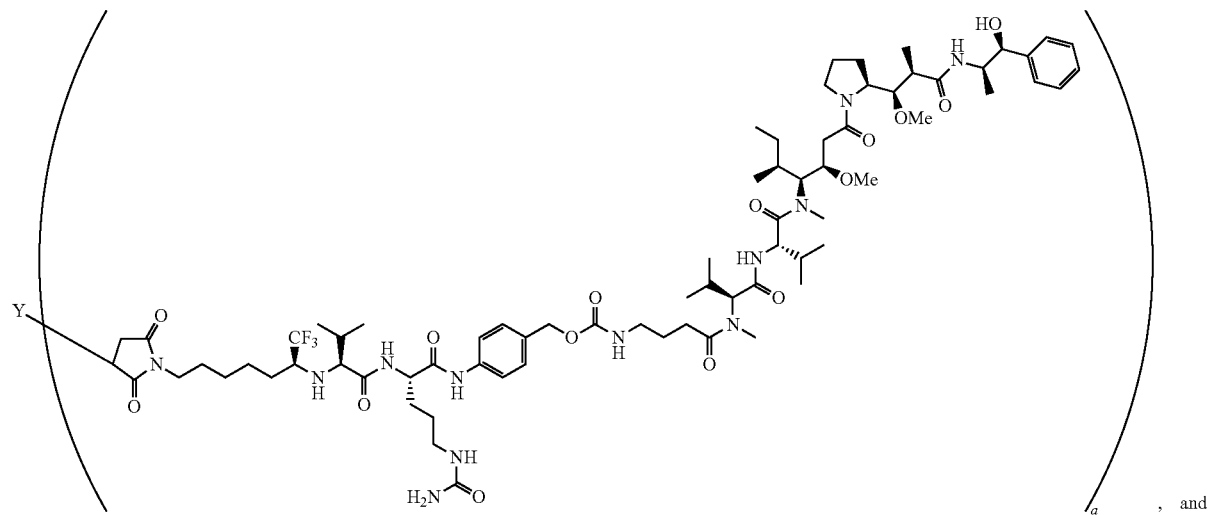
, and

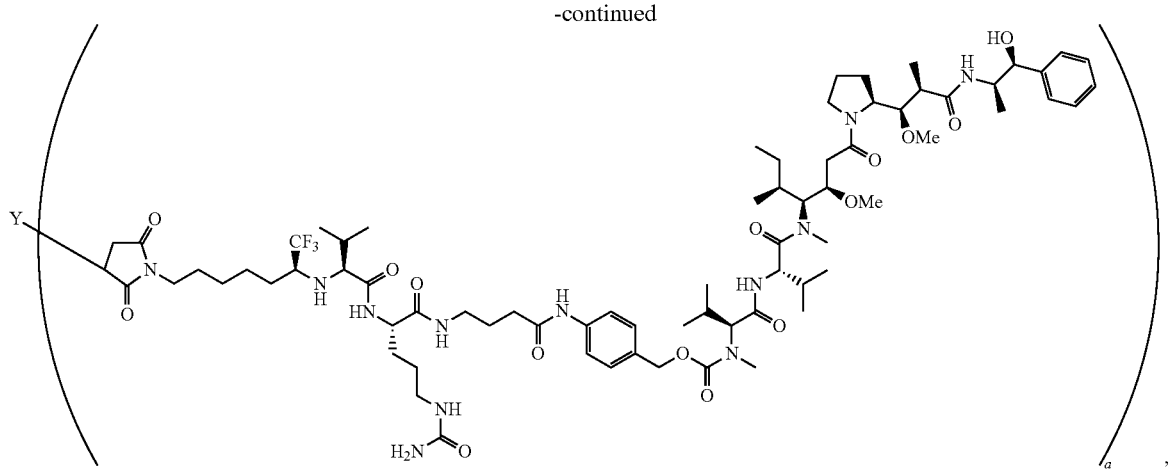
20
Y is an antibody, a is an integer or decimal selected from 1-8, concretely a is 1, 2, 3, 3.4, 3.5, 4, 4.2, 5, 6, 7, or 8.
In certain embodment of this invention, the aforesaid ADC is selected from the group consisting of:
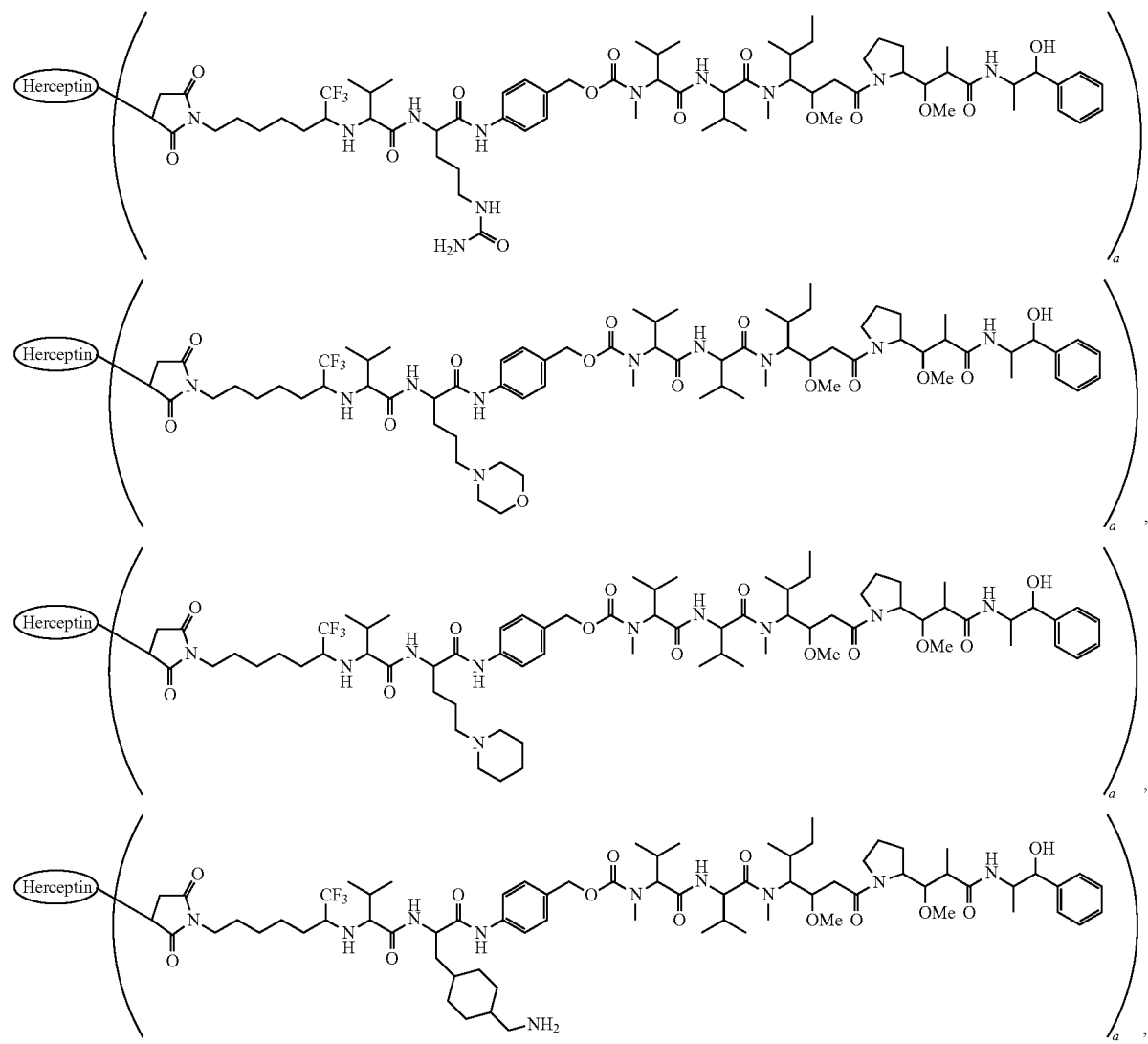

-continued
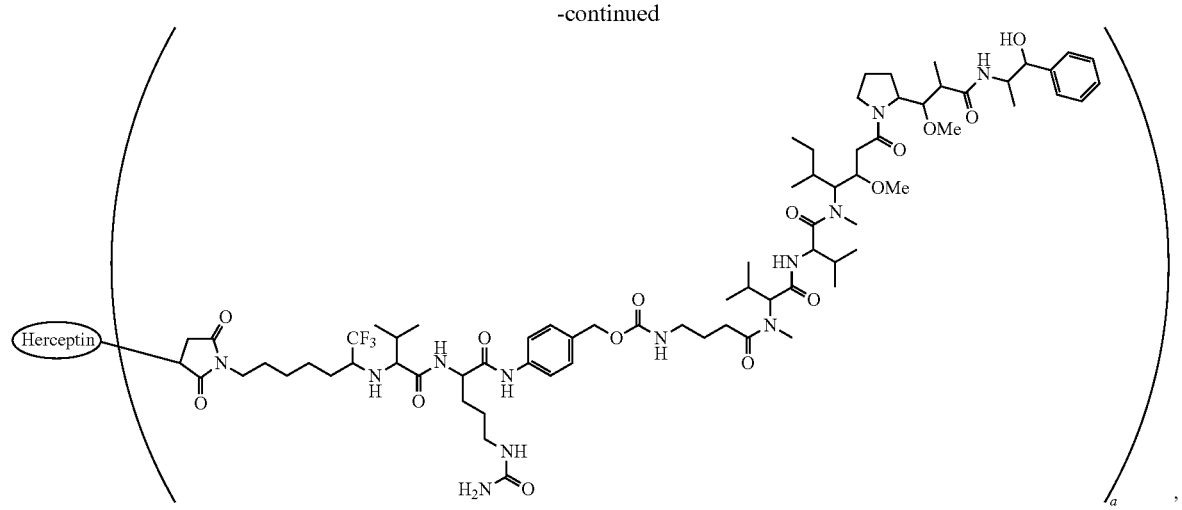
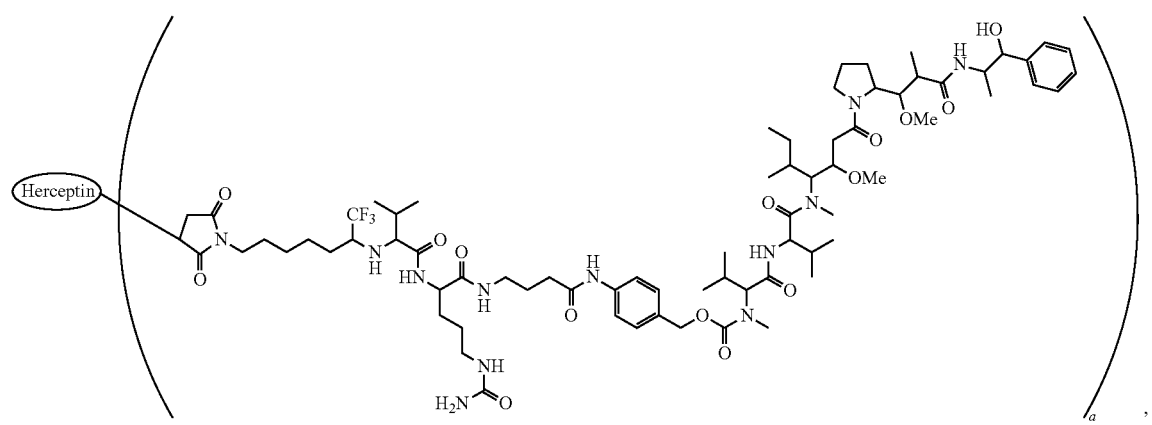
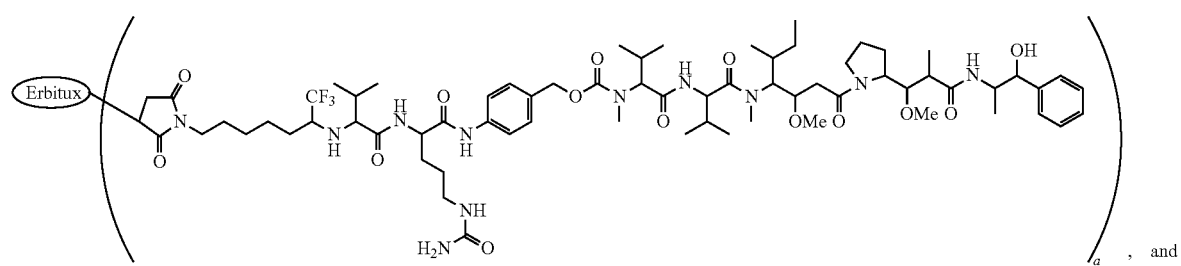
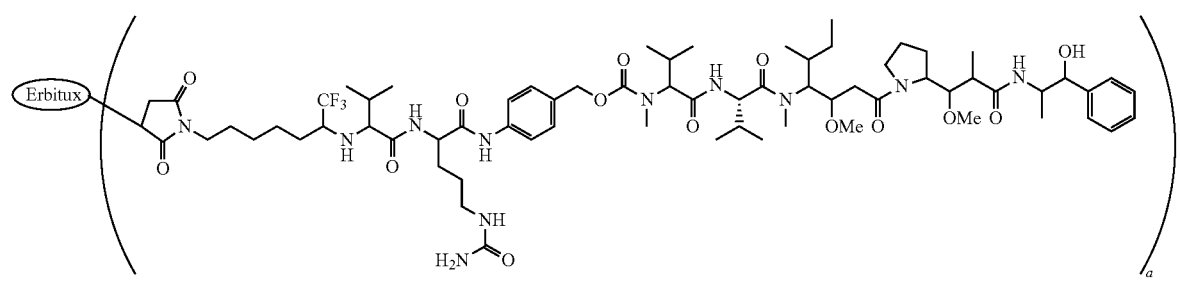
a is an integer or decimal selected from 2-6, concretely a is 2, 3, 3.4, 3.5, 4, 4.2, 5, or 6.
In certain embodment of this invention, the aforesaid ADC is selected from the group consisting of:

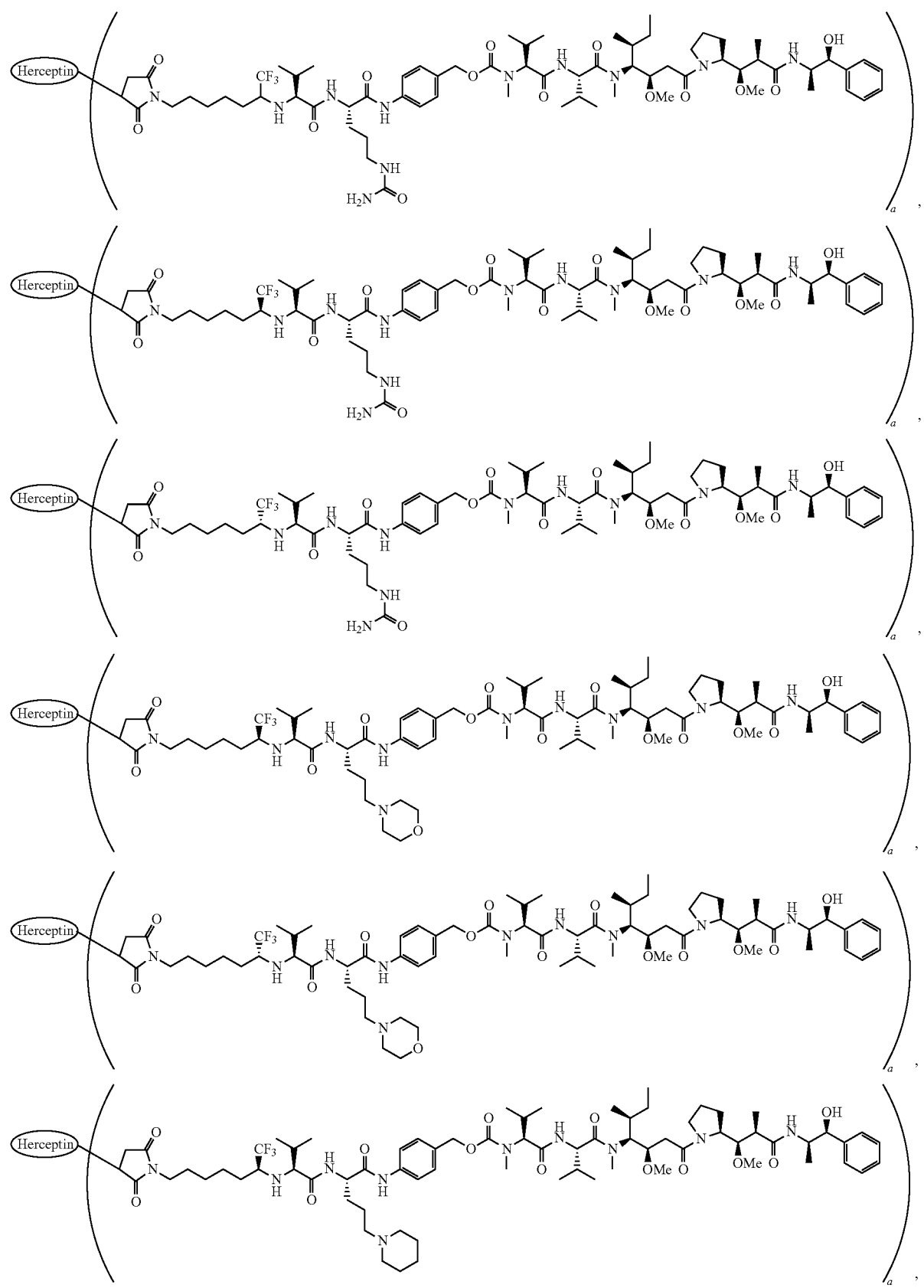

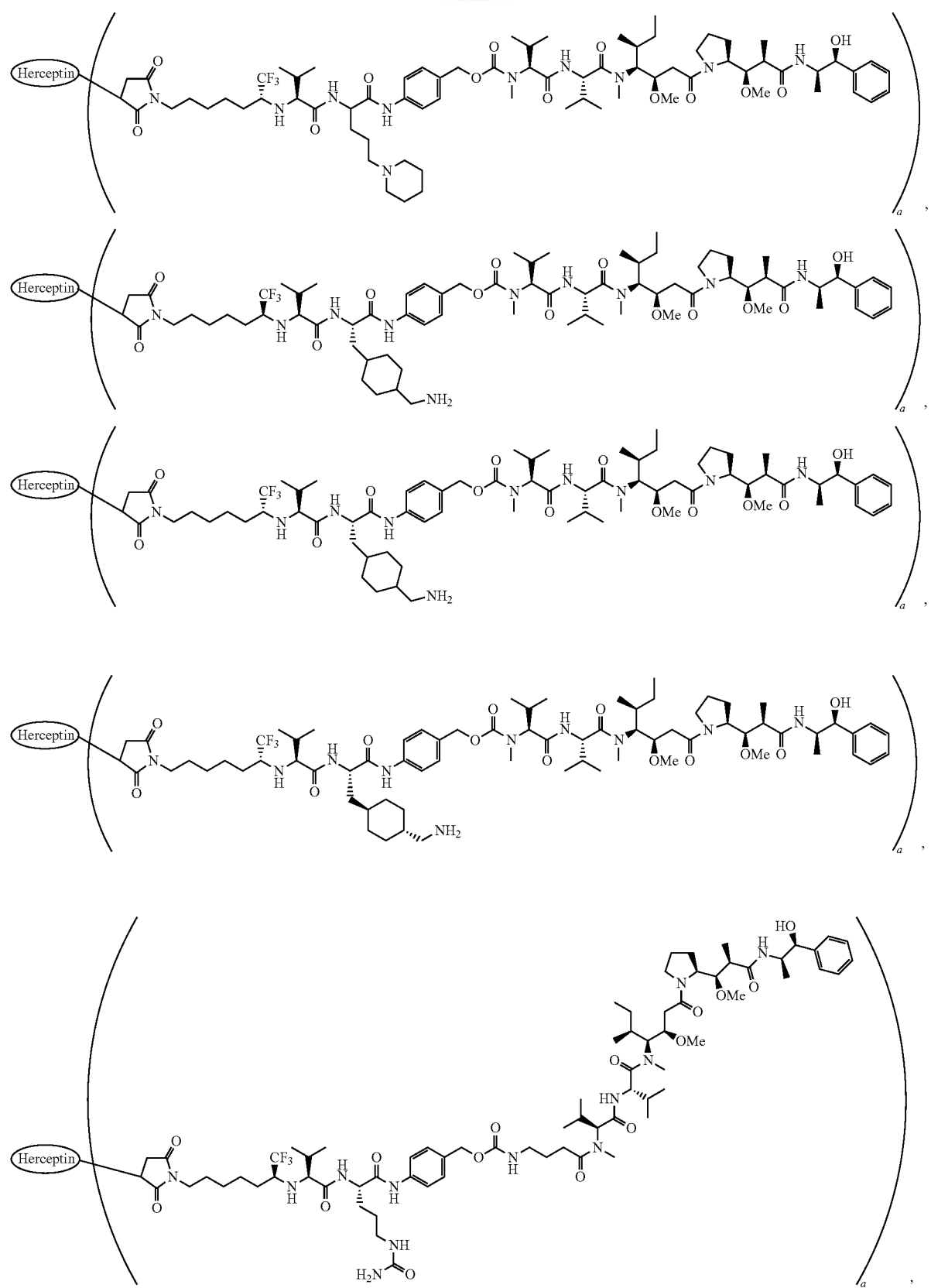

-continued
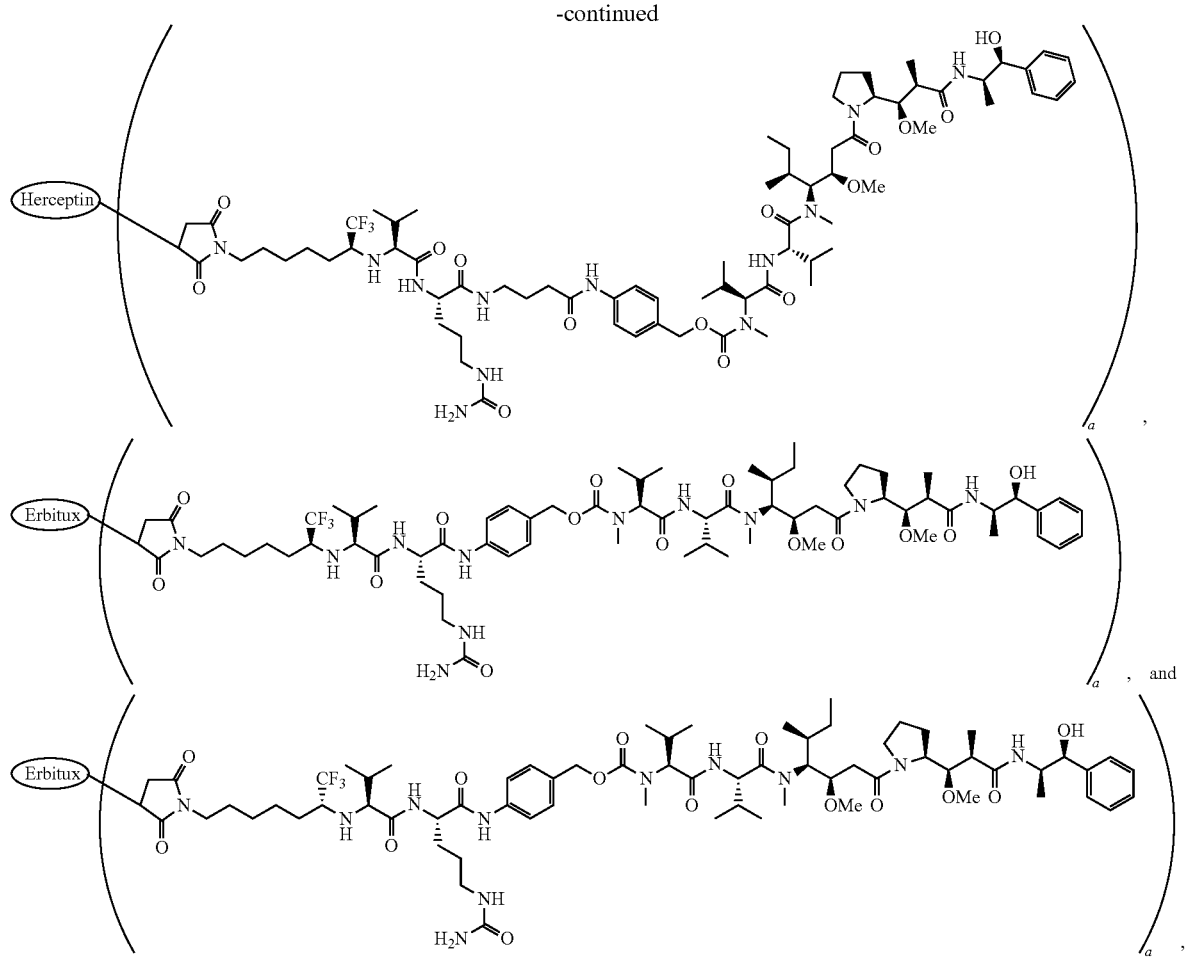
a is an integer or decimal selected from 2-6, concretely a is 2, 3, 3.4, 3.5, 4, 4.2, 5, or 6.
The present invention also provides intermediate compound for the synthesis of the drug-linker conjugate of formula (II) or the ADC of formula (III), comprising:
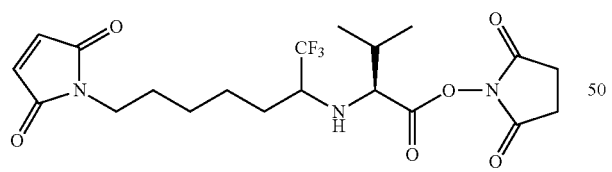
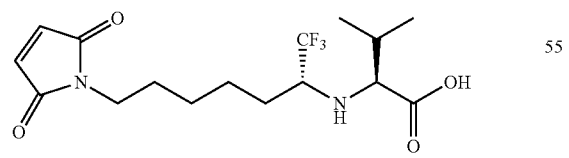
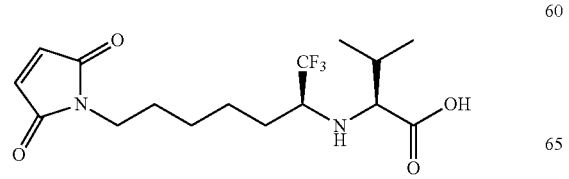
-continued
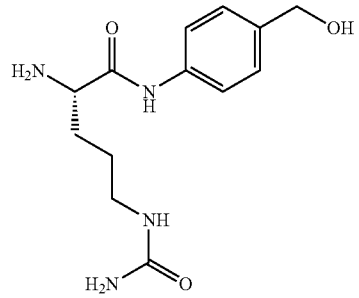
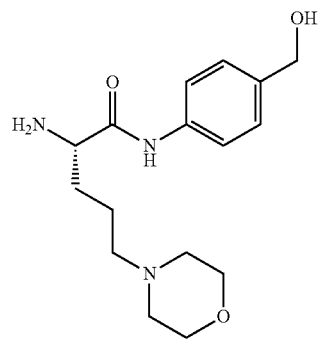

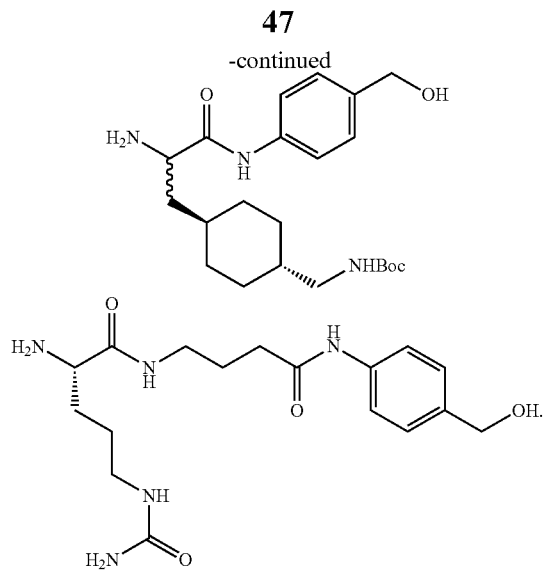

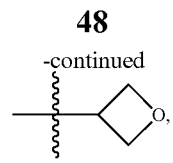

—CH$_2$CH(OH)(CH$_3$)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$, , , ,

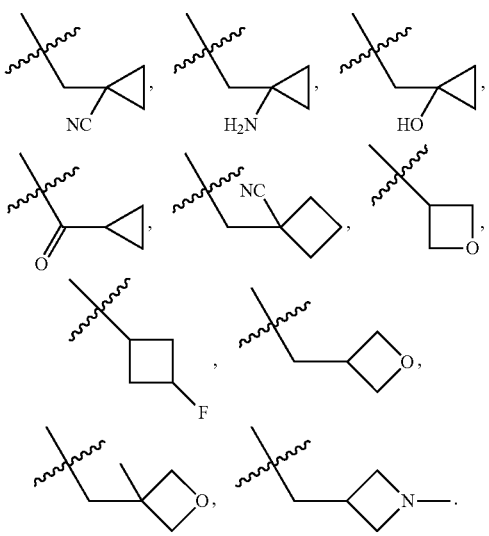

The present invention also provides a pharmaceutical composition comprising an effective amount of the aforesaid ADC and a pharmaceutically acceptable carrier, diluent or excipient.

The present invention also provides a use of the aforesaid linker, conjugate, or ADC or the aforesaid composition in the preparation of a medicament for the treatment of cancers.

The present invention also provides a method for treating or diagnosising cancers, comprising administrating the subject in need thereof an effective amount of the aforesaid ADC or the aforesaid pharmaceutical composition.

Definitions and Explanations

C$_{1-6}$ is selected from the group consisting of C$_1$, C$_2$, C$_3$, C$_4$, C$_5$, and C$_6$, the number denotes numbers of carbon atoms; C$_{3-6}$ is selected from the group consisting of C$_3$, C$_4$, C$_5$, and C$_6$.

C$_{1-6}$ alkyl, C$_{1-6}$ heteroalkyl, C$_{3-6}$ cyclohydrocarbyl, C$_{3-6}$ heterocyclohydrocarbyl, C$_{1-6}$ alkyl substituted by C$_{3-6}$ cyclohydrocarbyl or C$_{3-6}$ heterocyclohydrocarbyl, and C$_{1-6}$ heteroalkyl substituted by C$_{3-6}$ cyclohydrocarbyl or C$_{3-6}$ heterocyclohydrocarbyl include, but are not limited to: methyl, ethyl, n-propyl, isopropyl, —CH$_2$C(CH$_3$)(CH$_3$)(OH), cyclopropyl, cyclobutyl, propylmethylene, cycropropylacyl, benzyloxyl, cyclopropylalkylene, trifluoromethyl, aminomethyl, hydroxylmethyl, methyloxyl, methylacyl, methyloxylcarbonyl, methylsulfonyl, methylsulfinyl, ethyloxyl, ethylacyl, ethylsulfonyl, ethyloxylcarbonyl, dimethylamino, diethylamino, dimethylaminocarbonyl, and diethylaminocarbonyl;

N(CH$_3$)$_2$, NH(CH$_3$), —CH$_2$CF$_3$, —CH2CH$_2$CF$_3$, —CH$_2$CH$_2$F, —CH$_2$CH$_2$S(=O)$_2$CH$_3$, —CH$_2$CH$_2$CN,

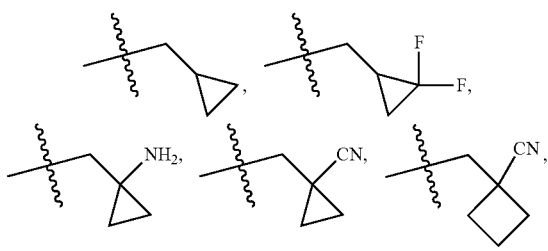

The term "substituted", as used herein, means that any one or more hydrogens on the designated atom is replaced with a selection from the indicated group, including deuterium "D" atom, a variant of hydrogen, provided that the designated atom's normal valency is not exceeded, and that the substitution results in a stable compound. When a substituent is keto (i.e., =O), then 2 hydrogens on the atom are replaced. Keto substituents are not present on aromatic moieties. The term "optionally substituted", as used herein, means that the designated atom can be substituted or unsubstituted by the substituents, and unless otherwise stated, the species and number the substituents are not defined provided that they can be achieved in Chemistry.

When any variable (e.g., R) occurs more than one time in any constituent or formula for a compound, its definition at each occurrence is independent of its definition at every other occurrence. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R",
—SR', -halogen, —SiR'R"R"', OC(O)R', —C(O)R', —CO$_2$R', —CONR'R",
—OC(O)NR'R", —NR"C(O)R', NR'C(O)NR"R"', —NR"C(O)$_2$R',
—NR""—C(NR'R"R"')=NR"", NR"" C(NR'R")=NR"', —S(O)R', —S(O)$_2$R',
—S(O)$_2$NR'R", NR"SO$_2$R', —CN, —NO$_2$, —N$_3$, —CH(Ph)$_2$, fluoro(C1-C4)alkoxy, and fluoro(C1-C4)alkyl, in a number ranging from zero to (2m'+1), where m' is the total number of carbon atoms in such radical. R', R", R"', R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', —NR'R", —SR', -halogen, —SiR'R"R"', OC(O)R', —C(O)R', —CO2R', —CONR'R", —OC(O)NR'R", —NR"C(O)R', NR' C(O)NR"R"', —NR"C(O)$_2$R', —NR""—C(NR'R"R"')=NR"", NR"" C(NR'R")=NR"', —S(O)R', —S(O)$_2$R', —S(O)$_2$NR'R", NR"SO$_2$R', —CN, —NO$_2$, —N$_3$, —CH(Ph)$_2$, fluoro(C1-C4)alkoxy, and fluoro(C1-C4)alkyl, in a number ranging from zero to the total number of open valences on the aromatic ring system; and where R', R", R"', R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""' groups when more than one of these groups is present.

Two of the substituents on adjacent atoms of the aryl or heteroaryl ring may optionally be replaced with a substituent of the formula -T-C(O)—(CRR')q-U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A(CH$_2$)r B—, wherein A and B are independently —CRR'—, —O—, —NR—, —S—, —S(O)—, S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R"')d-, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C1-C6)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C1-6 alkoxy, is intended to include C1, C2, C3, C4, C5, and C6 alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include C3, C4, C5, C6, and C7 cycloalkyl groups. Alkenyl" is intended to include hydrocarbon chains of either straight or branched configuration and one or more unsaturated carbon-carbon bonds that may occur in any stable point along the chain, such as ethenyl and propenyl.

"Halo" or "halogen" as used herein refers to fluoro, chloro, bromo, and iodo.

As used herein, the term "hetero", mean, unless otherwise stated, "heteroatom" or "heteroradical"(namely radical containing heteroatom), includeing atoms other than carbon (C) and hydrogen (H), also including the radicals containing these aforesaid heteroatoms. Examples include oxygen (O), nitrogen (N) sulfur (S), silicon (Si), germanium (Ge), aluminum (Al) and boron (B), also include optionally substituted —C(=O)N(H)—, —N(H)—, —C(=NH)—, —S(=O)$_2$ N(H)—, or —S(=O) N(H)—.

"Ring" as used herein, means a substituted or unsubstituted cycloalkyl, heterocycloalkyl, cycloalkenyl, heterocycloalkenyl, cycloalkynyl, heterocycloalkynyl, aryl, or heteroaryl. A ring includes mono, bi, sprio, fused, and bridged ring moieties. The number of atoms in a ring is typically defined by the number of members in the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heterocycle" or "heterocyclic group" is intended to mean a stable monocyclic, bicyclic, or tricyclic ring containing heteroatom or heteroradical, which is saturated, partially unsaturated or unsaturated (aromatic), and which consists of carbon atoms and 1,2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., NO and S (O) p). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group"or"heteroaryl"is intended to mean a stable 5,6, or 7-membered monocyclic or bicyclic or 7,8, 9, or 10-membered bicyclic heterocyclic aromatic ring which consists of carbon atoms and 1,2, 3, or 4 heterotams independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., NO and S (O) p). It is to be noted that total number of S and 0 atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1, 5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2, 5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2, 4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Also included are fused ring and spiro compounds containing, for example, the above heterocycles.

The term "hydrocarbyl" or its lower concept(such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). "Hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl include, but are not limited to, 6-12 membered aromatichydrocarbyl, for example, benzene, and naphthalene. In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its lower concept (such as heteroalkyl, heteroalkenyl, teteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heterohydrocarbyl group(including the position at which the hydrocarbyl group is attached to the remainder of the molecule). Examples include, but are not limited to, —CH2-CH2-O—CH3, —CH2-CH2-NH—CH3, —CH2-CH2-N(CH3)-CH3, —CH2-S—CH2-CH3, —CH2-CH2,—S(O)—CH3, —CH2-CH2-S(O)2-CH3, —CH=CH—O—CH3, —CH2-CH=N—OCH3, and —CH=CH—N(CH3)-CH3. Up to two heteroatoms may be consecutive, such as, for example, —$CH_2$—NH—$OCH_3$.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyclohydrocarbyl", "heterocyclohydrocarbyl", or their lower concepts(such as aryl, heteroaryl, cycloalkyl, heterocycloalkyl, cycloalkenyl, heterocycloalkenyl, cycloalkynyl, and heterocycloalkynyl etc.) by themselves or in combination with other terms, represent, unless otherwise stated, cyclic versions of "hydrocarbyl" or "heterohydrocarbyl", respectively. Additionally, for heterohydrocarbyl or heterocyclohydrocarbyl(such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "protecting group" includes bu not limited to "amino-protecting group", "hydroxy-protecting group" and "thiol-protecting group". The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Where the "antibody" is a cell-binding agent, it binds to an antigen that is a polypeptide and may be a transmembrane molecule (e.g. receptor) or a ligand such as a growth factor.

Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β, TGF-β2, TGF-beta]3, TGF-β4, or TGF-beta5; insulin-like growth factor-I and -II (IGF-I and IGF-II); des(I-3)-IGF-I (brain IGF-I), insulin-like growth factor binding proteins, EpCAM, GD3, FLT3, PSMA, PSCA, MUCI , MUC16, STEAP, CEA, TENB2, EphA receptors, EphB receptors, folate receptor, FOLRI, mesothelin, cripto, alphavbetae, integrins, VEGF, VEGFR, tarnsferrin receptor, IRTAI, IRTA2, IRTA3, IRTA4, IRTA5; CD proteins such as CD2, CD3, CD4, CD5, CD6, CD8, CDI 1 , CD14, CDI 9, CD20, CD21, CD22, CD23, CD25, CD26, CD28, CD30, CD33, CD36, CD37, CD38, CD40, CD44, CD52, CD55, CD56, CD59, CD70, CD79, CD80, CD81 , CDI 03, CDI 05, CDI 34, CDI 37, CDI 38, CDI 52; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-I to IL-IO; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CDI Ia, CDI Ib, CDI Ic, CDI 8, an ICAM, VLA-4 and VCAM; a tumor associated antigen such as HER2, HER3 or HER4 receptor; and fragments of any of the above-listed polypeptides, antibody mimics Adnectins (US appl 20070082365), or an antibody which binds to one or more tumor-associated antigens or cell-surface receptors disclosed in US Publication No. 20080171040 or US Publication No. 20080305044 and are incorporated in their entirety by reference.

Concrete antigens for antibodies encompassed by the present invention include CD proteins such as CD2, CD3, CD4, CD5, CD6, CD8, CD11, CD14, CD18, CD19, CD20, CD21, CD22, CD 25, CD26, CD27, CD28, CD30, CD33, CD36, CD37, CD38, CD40, CD44, CD52, CD55, CD56, CD70, CD79, CD80, CD81, CD103, CD105, CD134, CD137, CD138, and CD152; members of the ErbB receptor family such as the EGF receptor, HER2, HER3 or HER4 receptor; cell adhesion molecules such as LFA-I, MacI, pI50.95, VLA-4, ICAM-I, VCAM, EpCAM, alpha4/beta7 integrin, and alpha5/beta3 integrin including either alpha or beta subunits thereof (e.g. anti-CD11a, anti-CD18 or anti-CD11b antibodies); growth factors such as VEGF; tissue factor (TF); TGF-beta; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc.

The most concrete targets herein are IGF-IR, CanAg, EphA2, MUC1, MUC16, VEGF, TF, CD19, CD20, CD22, CD27, CD33, CD37, CD38, CD40, CD44, CD56, CD138, CA6, Her2/neu, EpCAM, CRIPTO (a protein produced at elevated levels in a majority of human breast cancer cells), darpins, alpha$_v$/beta$_3$ integrin, alpha$_v$/beta$_5$ integrin, alpha$_v$/beta$_6$ integrin, TGF-beta, CD11a, CD18, Apo2 and C242 or an antibody which binds to one or more tumor-associated antigens or cell-surface receptors disclosed in US Publication No. 20080171040 or US Publication No. 20080305044 and are incorporated in their entirety by reference.

Concrete antigens for antibodies encompassed by the present invention also include CD proteins such as CD3, CD4, CD8, CD19, CD20, CD27, CD34, CD37, CD38, CD46, CD56, CD70 and CD138; members of the ErbB receptor family such as the EGF receptor, HER2, HER3 or HER4 receptor; cell adhesion molecules such as LFA-I, MacI, pI50.95, VLA-4, ICAM-I, VCAM, EpCAM, alpha4/beta7 integrin, and alpha v/beta3 integrin including either alpha or beta subunits thereof (e.g. anti-CD11a, anti-CD 18 or anti-CD11b antibodies); growth factors such as VEGF; tissue factor (TF); TGE-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C, etc. The most concrete targets herein are IGF-IR, CanAg, EGF-R, EGF-RvIII, EphA2, MUCI, MUC16, VEGF, TF, CD19, CD20, CD22, CD27, CD33, CD37, CD38, CD40, CD44, CD56, CD70, CD 138, CA6, Her2/neu, CRIPTO (a protein produced at elevated levels in a majority of human breast cancer cells), alpha v/beta3 integrin, alpha v/beta5 integrin, TGE-β, CDI Ia, CD18, Apo2, EpCAM and C242.

Monoclonal antibody techniques allow for the production of specific cell-binding agents in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the antibody is a matter of choice that depends upon the particular cell population that is to be targeted, but in general monoclonal antibodies and epitope binding fragments thereof are preferred, if an appropriate one is available.

For example, the monoclonal antibody My9 is a murine IgG2a antibody that is specific for the CD33 antigen found on Acute Myeloid Leukemia (AML) cells (Roy et al. Blood 77:2404-2412 (1991)) and can be used to treat AML patients. Similarly, the monoclonal antibody anti-B4 is a murine IgGi that binds to the CD 19 antigen on B cells (Nadler et al, J Immunol. 131:244-250 (1983)) and can be used if the target cells are B cells or diseased cells that express this antigen such as in non-Hodgkin's lymphoma or chronic lymphoblastic leukemia. The antibody N901 is a murine monoclonal IgGi antibody that binds to CD56 found on small cell lung carcinoma cells and on cells of other tumors of neuroendocrine origin (Roy et al. J Nat. Cancer Inst. 88:1136-1145 (1996)); huC242 is an antibody that binds to the CanAg antigen; Trastuzumab is an antibody that binds to HER2/neu; and anti-EGF receptor antibody binds to EGF receptor.

The drug unit used in this invention can be any cytotoxic, cytostatic or immunosuppressive drug also referred to herein as a cytotoxic, cytostatic or immunosuppressive agent. Examples of drugs include radioactive isotopes, chemotherapeutic agents, and toxins such as small molecule toxins or enzymatically active toxins of bacterial, fungal, plant or animal origin, including synthetic analogues and derivatives thereof. The Drug unit has an atom that can form a bond with the Linker Unit, in some embodiments, the Drug unit has a nitrogen atom that can form a bond with the Linker unit. In other embodiments, the Drug unit has a carboxylic acid that can form a bond with the Linker unit. In other embodiments, the Drug unit has a sulfhydryl group that can form a bond with the Linker unit . In other embodiments, the Drug unit has a hydroxy! group or ketone that can form a bond with the Linker unit.

Useful classes of cytotoxic or immunosuppressive agents include, for example, antitubulin agents, auristatins, DNA minor groove binders, DNA replication inhibitors, alkylating agents (e.g. , platinum complexes such as cis-platin, mono(platinum), bis(platinum) and tri-nuelear platinum complexes and carbopiatin), anthracyclin.es, antibiotics, antifolates-, antimetabolites, chemotherapy sensitizers, duocarmycins, etoposides, fluorinated pyrimidines, ionophores, lexitropsins, nitrosoureas, platinois, pre-formirsg compounds, purine antimetabolites, puromycins, radiation sensitizers, steroids, taxanes, topoisornerase inhibitors, vinca alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM! and DM4), taxanes, benzodiazepines (e.g., pyrrolo [1,4] benzodiazepines (PBDs). indolinobenzodiazepines, and oxazolidinobenzodiazepines) and vinca alkaloids. Select benzodiazepine containing drugs are described in WO 2010/091 150, WO 2012/1 12708, WO 2007/085930, and WO 201 1/023883.

Individual cytotoxic or immunosuppressive agents include, for example, an androgen, antbramycin (AMC), asparaginase, 5-azacytidine, azathioprine, bleomycin, busuJfan, buthionine sulfoximine, calicheamicin, camptothecin, carbopiatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin). daunorubicin, decarbazine, docetaxel, doxorubicin, etoposide, an estrogen, 5-fluordeoxyuridine, 5-fluorouracil, gemcitabine, gramicidin D, hydroxyurea, idarubicin, ifosfamide, irinoteean, iomustine (CCNU), mayiansine, mechlorethainine, melphalan, 6-mercaptopurine, methotrexate, mithramycin, mitomycin C, mitoxantrone, nitroimidazole, paclitaxei, paly toxin, plicamycin, procarbizine, rhizoxin, streptozotocin, tenoposide, 6-thioguanine, thioTEPA, topotecan, vinblastine, vincristine, vinorelbine, VP-16 and VM-26.

In certain typical embodiments, suitable cytotoxic agents include, for example, DNA minor groove binders (e.g., enediynes and exitropsins, a CBI compound; see also U.S. Pat. No. 6,130,237), duocarmycras (see U.S. Publication No. 20060024317), taxanes (e.g., paclitaxei and docetaxel), puromycins, vinca alkaloids, CC-1065, SN-38, topotecan, morpholino-doxorubicin, rhizoxin, cyanomorpholino-doxorubicin, echinomvcin, combretastatin, netropsin, epothilone A and B, estramustine, cryptophysins, cemadotin, maytansinoids, discodermoiide, eleutherobin, and mitoxantrone.

In certain embodiments, the Drug unit is an anti-tubulin agent. Examples of anti-tubulin agents include, but are not limited to, taxanes (e.g., Taxol® (paclitaxei), Taxotere© (docetaxel)), T67 (Tularik) and vinca alkyloids (e.g., vincristine, vinblastine, vindesme, and vinorelbine). Other anti-tubulin agents include, for example, baccatin derivatives, taxane analogs (e.g., epothilone A and B), nocodazole, colchicine and colcimid, estramustine, cryptophysins, cemadotin, maytansinoids, combretastatins, discodermoiide, and eleutherobin.

In certain embodiments, the cytotoxic agent is maytansine or a maytansinoid, another group of anti-tubulin agents. (ImmunoGen, Inc.: see also Chari et ah, 1992, Cancer Res. 52:127-131 and U.S. Pat. No. 8,163,888).

In certain embodiments, the Drug unit is an auristatin. Auristatins include, but are not limited to, AE, AFP, AEB, AEVB, MMAF, and MMAE. The synthesis and structure of auristatins are described in U.S. Patent Application Publication Nos. 2003-0083263, 2005-0238649 2005-0009751, 2009-01 1 1756, and 201 1-0020343: International Patent Publication No. WO 04/010957, international Patent Publication No. WO 02/088172, and U.S. Pat. Nos. 7,659,241 and 8,343,928; each of which is incorporated by reference in its entirety and for all purposes. Exemplary auristatins of the present invention bind tubulin and exert a cytotoxic or cytostatic effect on the desired cell line.

Exemplary auristatin Drug units have the following formula or a pharmaceutically acceptable salt thereof wherein the wavy line indicates site of attachment to the linker unit:

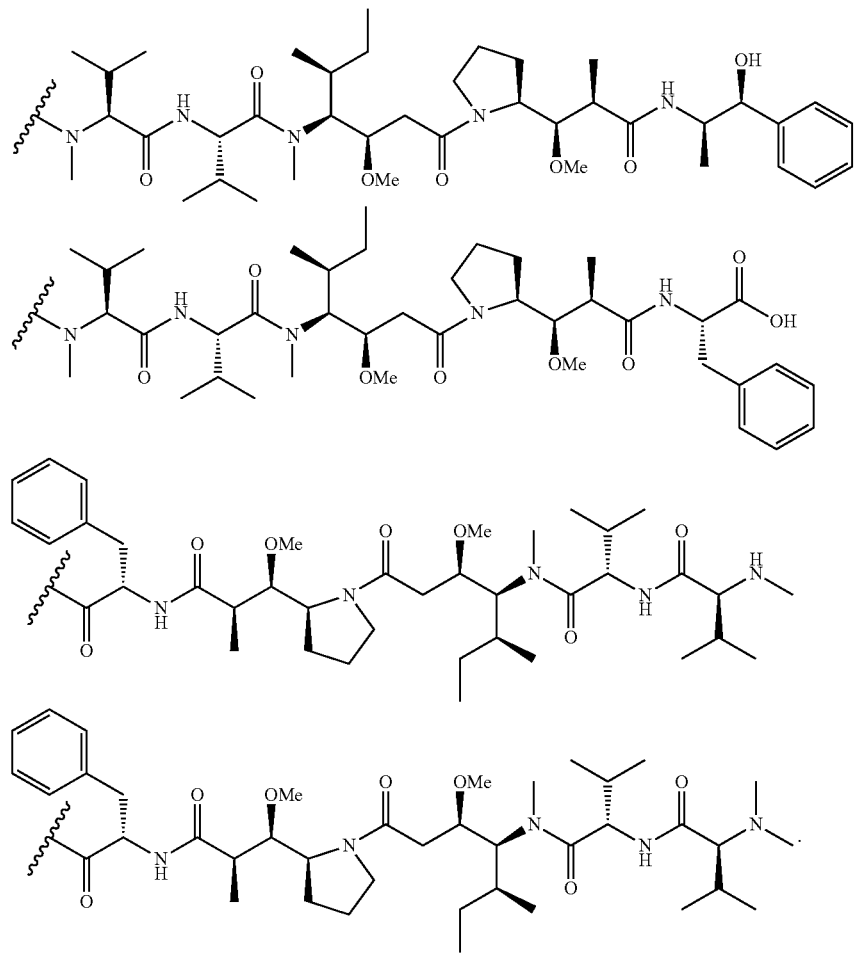

In certain embodiments, the Drug is a benzodiazepine (including benzodiazepine containing drugs e.g., pyrrolo[1, 4]benzodiazepiries (PBDs), indolinobenzodiazepines, and oxazo!idino benzodiazepines). PBDs are of the general structure:

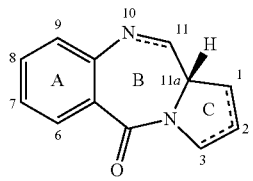

but can differ in the number, type and position of substituents, in both their aromatic A rings and pyrrolo C rings, and in the degree of saturation of the C ring. In the B-ring there is either an imine (N=), a carbinolamine(NH—CH(OH)), or a carbinolamine methyl ether (NH—CH(OMe)) at the N10-C11 position, which is the electrophilic center responsible for alkylating DNA. All of the known natural products have a (S)-configuration at the chiral CI 1a position which provides them vvitli a right-handed twist when viewed from the C ring towards the A ring. This gives them the appropriate three-dimensional shape for isohelicity with the minor groove of B-form DNA, leading to a. snug fit at the binding site. The ability of PBDs to form an adduct in the minor groove enables them to interfere with DNA processing, hence their use as antitumour agents. The biological activity of these molecules can be potentiated by, for example, joining two PBD units together through their C8/C -hydroxyl functionalities via a flexible alkylene linker. The PBD dimers are thought to form sequence-selective DNA lesions such as the palindromic 5'-Pu-GATC-Py-3' interstrand crosslink which is thought to be mainly responsible for their biological activity.

General Method to Prepare Linkers, Drug-Linker Conjugates and ADCs:
Method 1

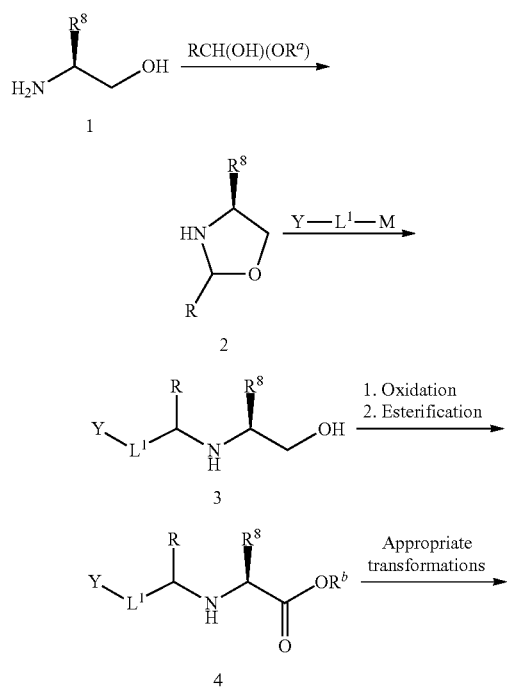

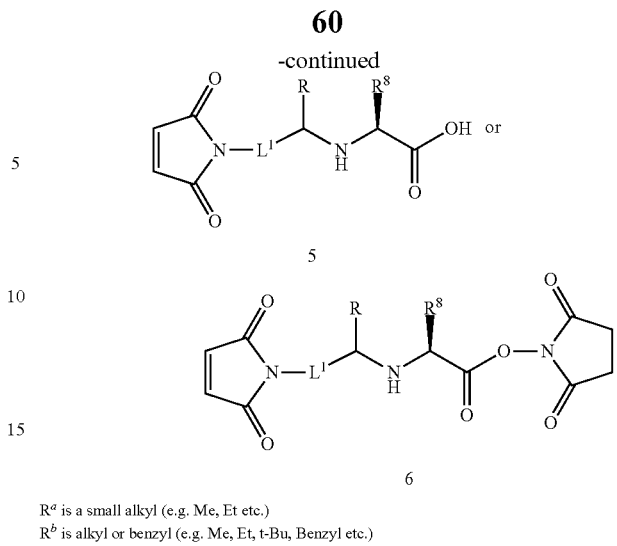

$R^a$ is a small alkyl (e.g. Me, Et etc.)
$R^b$ is alkyl or benzyl (e.g. Me, Et, t-Bu, Benzyl etc.)

An amino alcohol 1 is reacted with a hemiacetal such as trifluoroacetaldehyde methyl hemiacetal in a solvent such as toluene at refluxing temperature with concomitant removal of water to give an oxazolidine intermediate 2. Oxazolidine 2 is then reacted with a Grignard or alkali reagent derived from an appropriate precursor to afford an amino alcohol intermediate 3. Oxidation under an appropriate condition such as Jones reagent or periodic acid with catalytic amount of chromium trioxide and followed by esterifaction furnishes the ester intermediate 4. Appropriate manipulation of functional groups on intermediate 4 affords intermediate 5 with suitable handles for further transformations.

Method 2

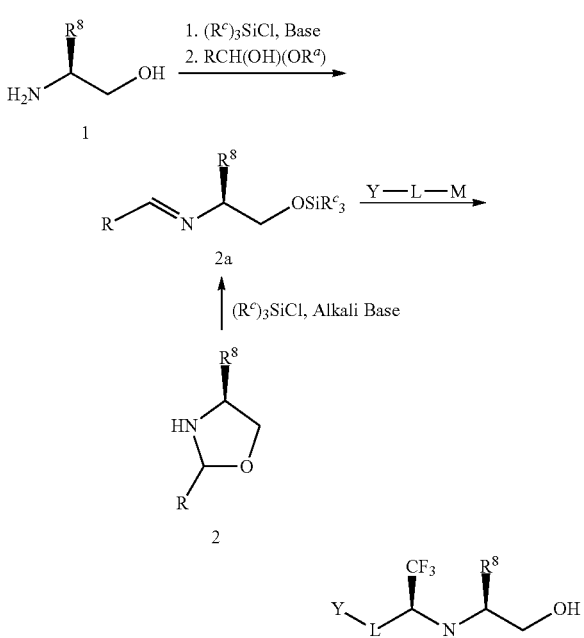

$(R^c)_3SiCl$ is standard silyl protecting group, e.g. $Me_3SiCl$, $Et_3SiCl$, $t-BuMe_2SiCl$ etc The amino alcohol 3 in Method 1 can also be prepared in a diastereo-selective manner as described in Gosselin, F., et. al., *Org. Lett.* 2004, 6, 641 and Roy, A., et. al., *J. Org. Chem.* 2006, 71, 4320 to give 3a with high distereoselectivity.

Method 3

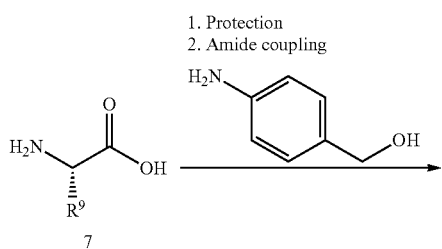

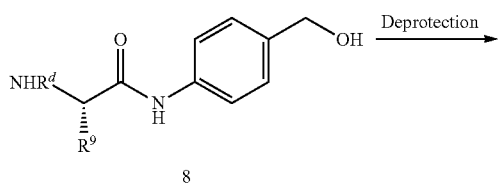

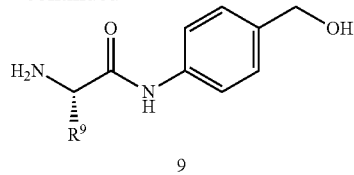

$R^d$ is a standard amine protecting group, e.g. Fmoc, cbz, Boc, etc

Amino acid 7 is protected with an appropriate protecting group on the amino moiety and then coupling with 4-amino benzyl alcohol to give intermediate 8 in a standard manner. The protecting group on the amine is then removed to give intermediate 9.

Method 4

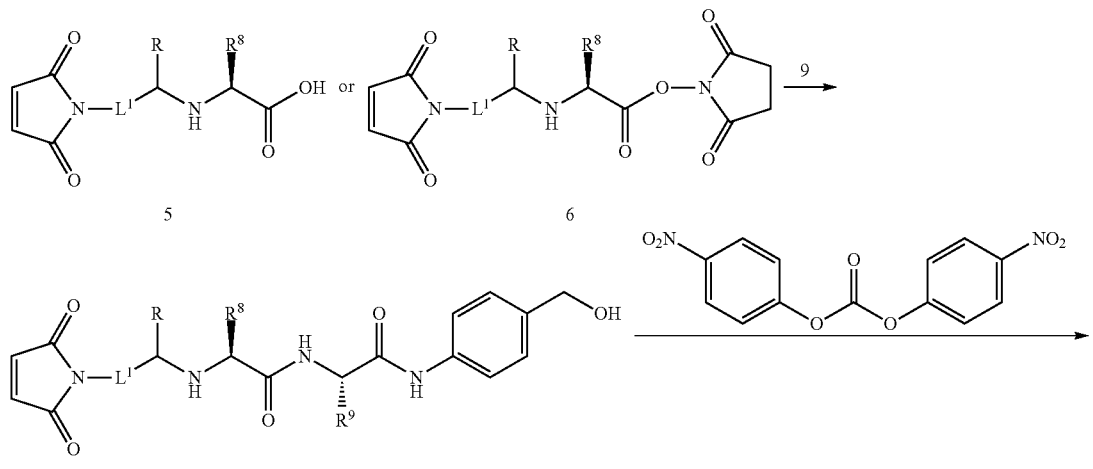

Intermediate 5 or 6 from Method 1 and intermediate 8 from Method 3 is reacted under an appropriate condition to give intermediate 10. Intermediate 10 is then converted to the 4-nitrophenyl carbonate intermediate 11.

Method 5

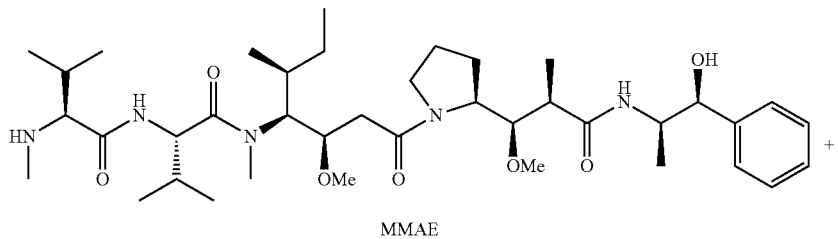

MMAE

-continued

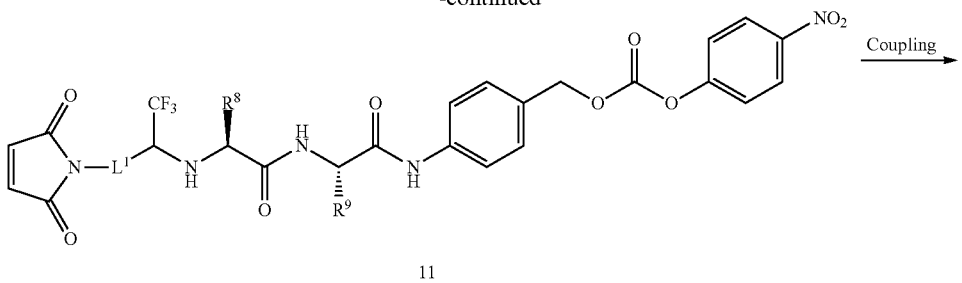

11

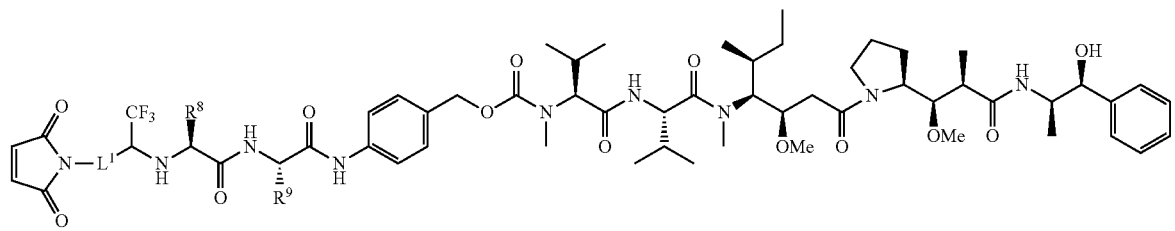

12

Intermediate 11 from Method 4 is reacted with MMAE under an appropriate condition to give linker-drug intermediate 12.

Method 6

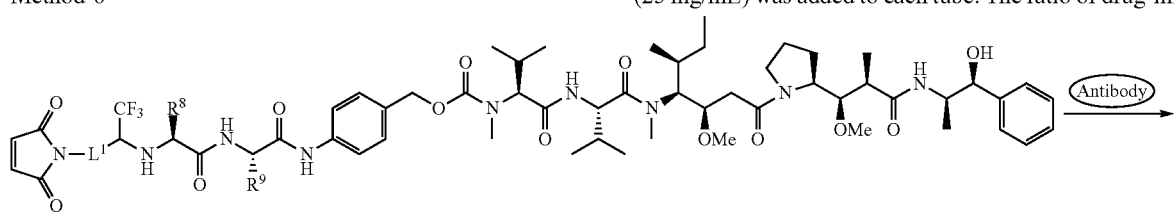

12

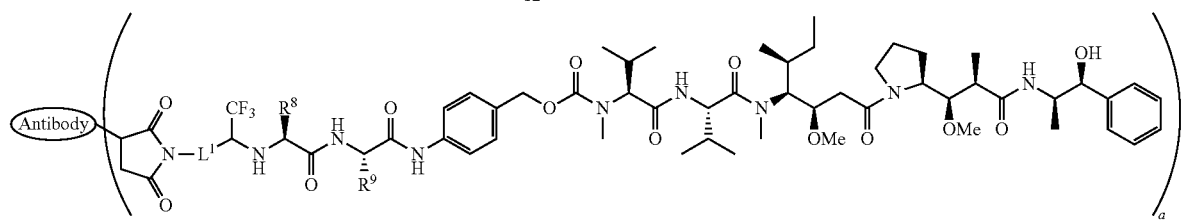

13

Intermediate 12 is coupled with the desired antibody under an appropriate condition as described in the corresponding experimental section.

General Procedure for Conjugation of Drug-Linker Intermediate to Herceptin:

Step 1: Reduction of Disulfide Bond of Antibody and Purification

To produce 240 mg ADC, 8.955 mL Hereceptin (26.8 mg/mL, around 30 mg·mL) was mixed with 8.95 μL 0.5 M TCEP (final concentration of TCEP in reaction mixture was 0.5 mM), and the reaction was performed at room temperature for 2 hour. Then the reaction solution was loaded on an 1 mL Protein A affinity column to get rid of the remained TCEP and other non-mAb impurities. After the purification, pH of the eluent was adjusted to around 6.0 with 1 M Tris, and the concentration of mAb was measured by nanodrop. The final volume of the solution was about 20 mL, and mAb concentration was 11.6 mg/mL.

Step 2: Conjugation of Drug-Linker and Antibody

The solution was divided equally into to two tubes (10 mL each), and 1 mL DMSO solution of drug-linker intermediate (25 mg/mL) was added to each tube. The ratio of drug-linker intermediate to mAb is 6:1. The reaction was carried out at room temperature for ca 12 hour. When finished, solutions from the two tubes were pooled, centrifuged at 5000 rpm for 5 min and loaded onto a Protein A affinity column to remove the un-reacted drug-llinker intermediate. The pH of the eluent from the column was adjusted to 6.0 with 1 M Tris buffer. The drug antibody ratio (DAR) was determined by hydrophobic interaction chromatography (HIC) HPLC.

The invention is now is further described by examples. The examples given below are for illustration purpose and not meant to limit this invention. The compounds of the present invention can be prepared in a number of ways known to one skilled in the art of organic synthesis. The examples of the present invention can be synthesized using the methods described below, together with synthetic methods known in the art of synthetic organic chemistry, or by variations thereon as appreciated by those skilled in the art. Concrete methods include, but are not limited to, those described below.

All solvents used are commercially available and are used without further purification. Reactions are typically run using anhydrous solvents under an inert atmosphere of nitrogen. Proton NMR are recorded on Bruker Avance III 400 (400 MHz) spectrometer and chemical shifts are reported as (ppm) down field from tetramethylsilane. Mass spectra are determined on Agilent 1200 series plus 6110 (& 1956A). LC/MS, or Shimadzu MS consisting of a DAD: SPD-M20A (LC) and Shimadzu Micromass 2020 detector. The mass spectrometer is equipped with an electrospray ion source (ESI) operated in a positive or negative mode.

The following abbreviations are used: ADC is antibody-drug conjugate;aq is aqueous; mAb is monoclonal antibody; MTMH is 1-Maleinimidyl-6-trifluoromethylhex-6-yl with the structure of

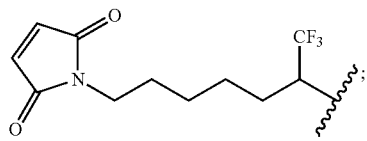 [SMILES: *C(CCCCCN1C(=O)C=CC1=O)C(F)(F)F]

(S)-MTMH is

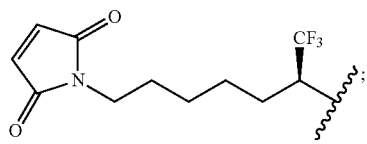 [SMILES: *[C@@H](CCCCCN1C(=O)C=CC1=O)C(F)(F)F]

(R)-MTMH is

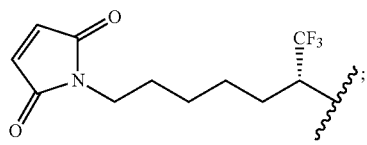 [SMILES: *[C@H](CCCCCN1C(=O)C=CC1=O)C(F)(F)F]

PABO(CO) is

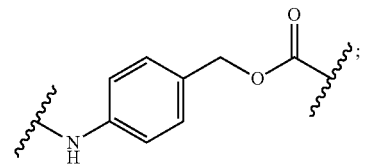 [SMILES: *Nc1ccc(COC(*)=O)cc1]

ABA is

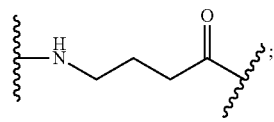 [SMILES: *NCCCC(*)=O]

MMAE is

Fmoc-Cl is 9-fluorenylmethyl chloroformate; DIAD is diisopropyl azodicarboxylate; Z-Glu-OMe is (S)-4-(((benzyloxy)carbonyl)amino)-5-methoxy-5-oxopentanic acid; HATU is 1-[Bis(dimethylamino)methylene]-1H-1,2,3-triazolo[4,5-b]pyridinium 3-oxid hexafluorophosphate; EDCl is 1-Ethyl-3-(3-dimethylaminopropyl)carbodiimide; DMSO is Dimethyl sulfoxide; HOBT is Hydroxybenzotriazole; DCM is dichloromethane; PE is petroleum ether; DMF is N,N-dimethylformamide; DMSO is dimethylsulfoxide; EtOAc is ethyl acetate; EtOH is ethanol; MeOH is methanol; Cbz is benzyloxycarbonyl, a amine protecting group; BOC is tert-butylcarbonyl, amine protecting group; HOAc is acetic acid; $NaBH(OAc)_3$ is sodium triacetoxyborohydride; r.t. is room temperature; THF is tetrahydrofuran; $Boc_2O$ is di-tert-butyl dicarbonate; TFA is trifluoroacetic acid; DIPEA is diisopropylethylamine; $Pd(dppf)Cl_2$ is [1,1'-Bis(diphenylphosphino)ferrocene]dichloropalladium(II); $POCl_3$ is phosphorus oxychloride; NaH is sodium hydride; LAH is Lithium Aluminium Hydride; $Pd(OAc)_2$ is Palladium (II) acetate; $Pd_2(dba)_3$ is tris(dibenzylideneacetone)dipalladium; $Pd(PPh_3)_4$ is tetrakis(triphenylphosphine)palladium; $Et_3SiH$ is triethylsilane; $PPh_3$ is triphenyl phosphine; Xantphos is 4,5-Bis(diphenylphosphino)-9,9-dimethylxanthene;

$MeSO_3H$ is methanesulfonic acid; Xphos is 2-Dicyclohexylphosphino-2',4',6'-triisopropylbiphenyl; Lawesson's reagent is 2,4-Bis(4-methoxylphenyl)-1,3-dithia-2,4-diphosphetane-2,4-disulfide; NBS is N-bromosuccinimide; t-BuOK is potassium tert-butylate;

Compounds are named either manually or by using ChemDraw®, or using vendors catalogue name if commercially available.

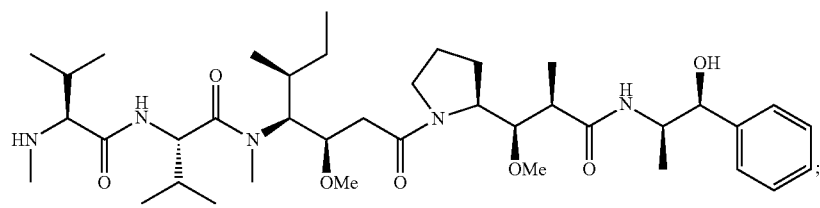 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Figure 1:
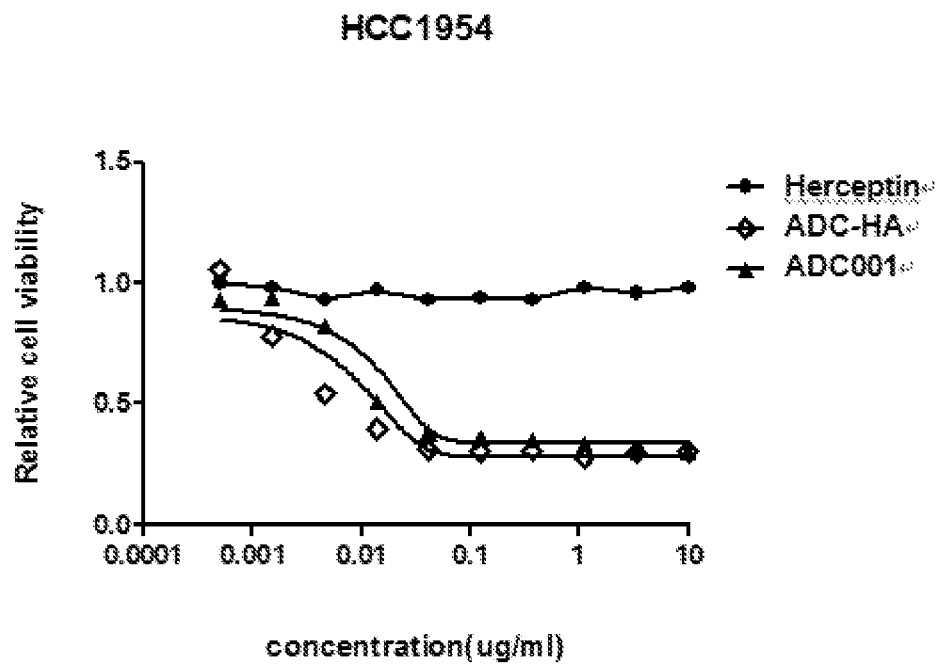
FIG. 1 showed the antiproliferative activity of Herceptin and different ADCs and the result suggested that the study ADC001 (EXAMPLE 9) and the control ADC-HA showed comparable activity in the inhibition on the growth of breast cancer cell line HCC1954 in vitro. Herceptin alone is ineffective in this assay.
Figure 2:
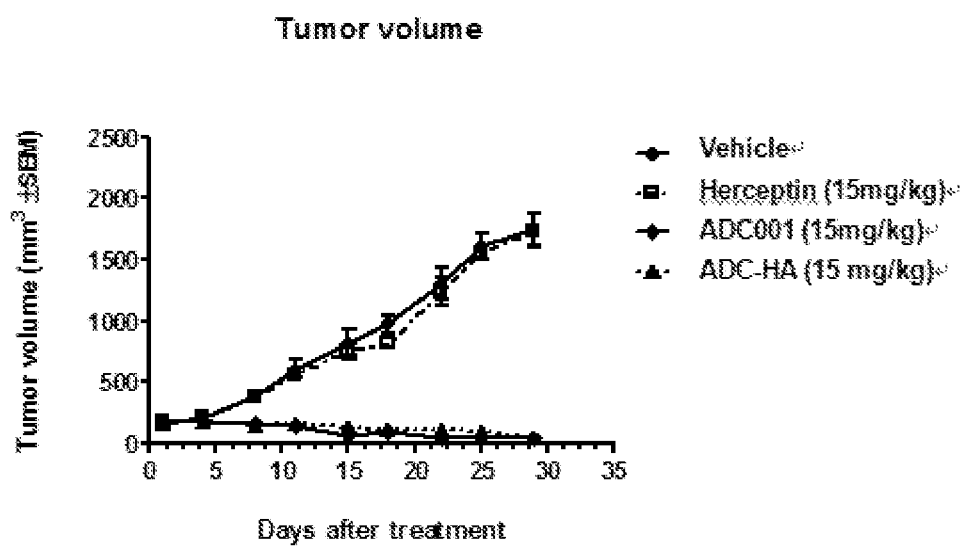
FIG. 2 showed the tumor growth curves from each group. The result suggested that the study ADC001 (EXAMPLE 9) and the control ADC-HA displayed comparable activity to inhibit tumor growth in the HCC1954 xenograft mice model.
Figure 3:
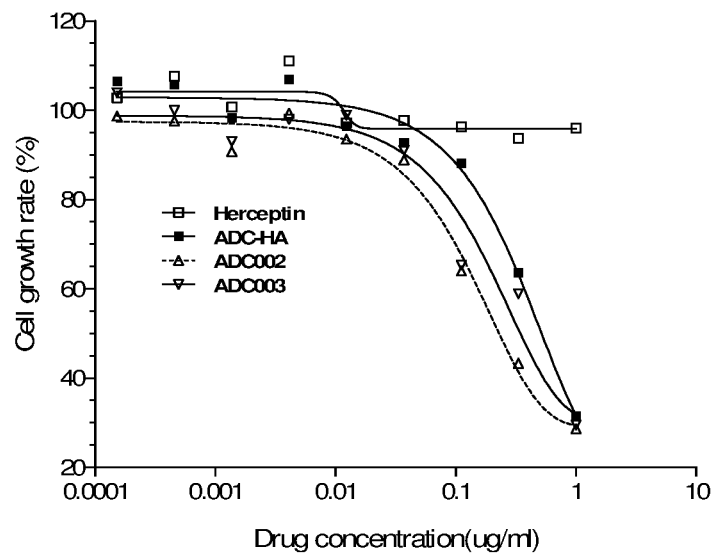
FIGS. 3 and 4 showed the antiproliferative activity of Herceptin and ADCs (ADC002 to ADC006, EXAMPLE 10 to 14) and the result suggested that the study ADCs and the control ADC-HA showed comparable activity in the inhibition on the growth of breast cancer cell line HCC1954 in vitro. Herceptin alone is ineffective in this assay FIGS. 5 to 10 showed the tumor growth curves for control ADC-HA and ADCs (ADC-002 to ADC006, EXAMPLE 10 to 14).
Figure 4:
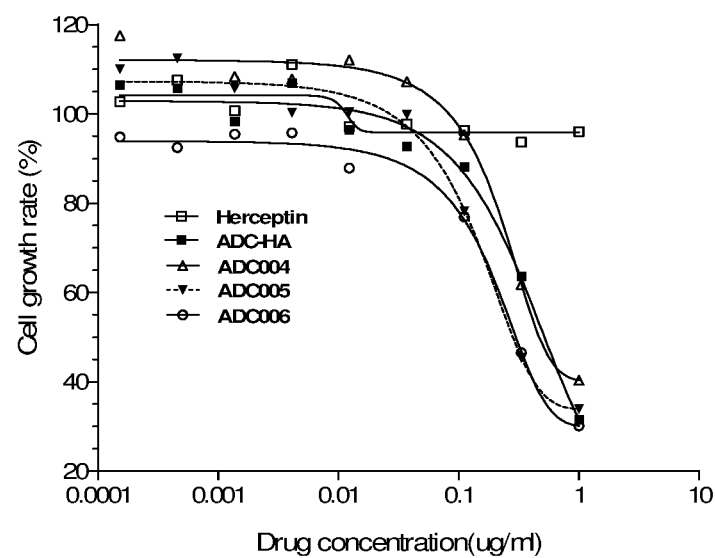
Figure 5:
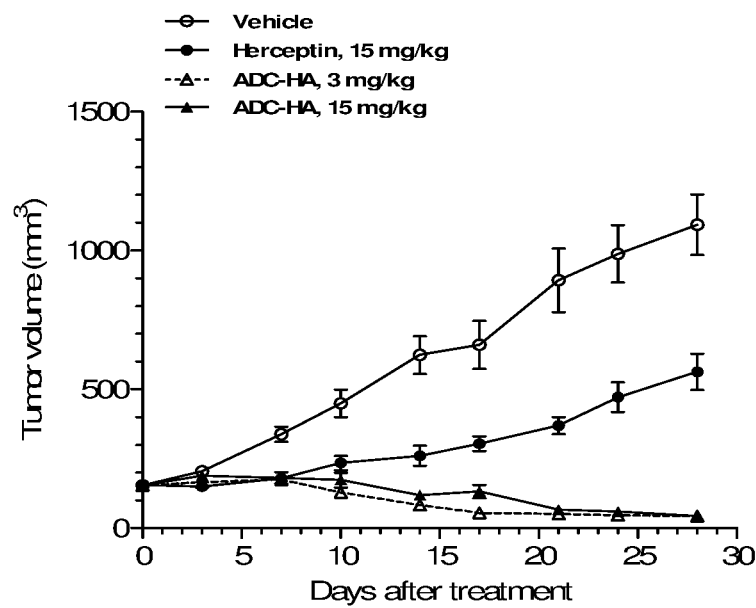
Figure 6:
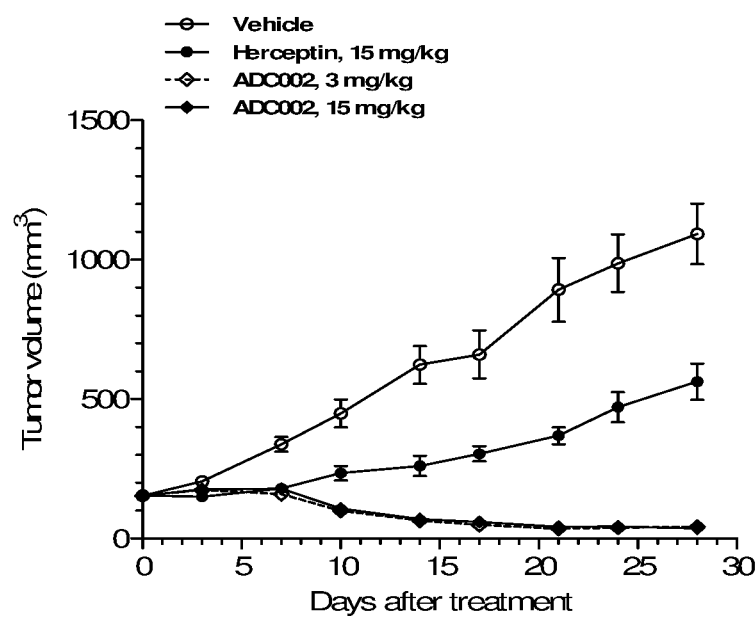
Figure 7:
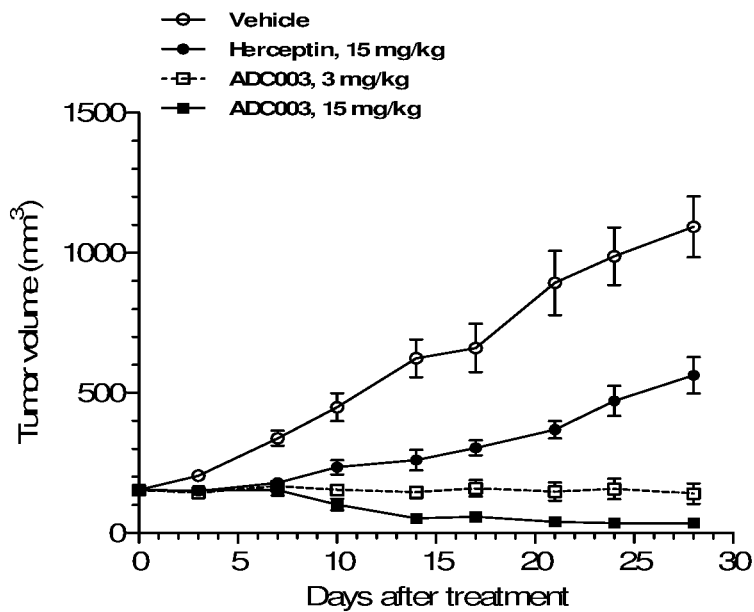
Figure 8:
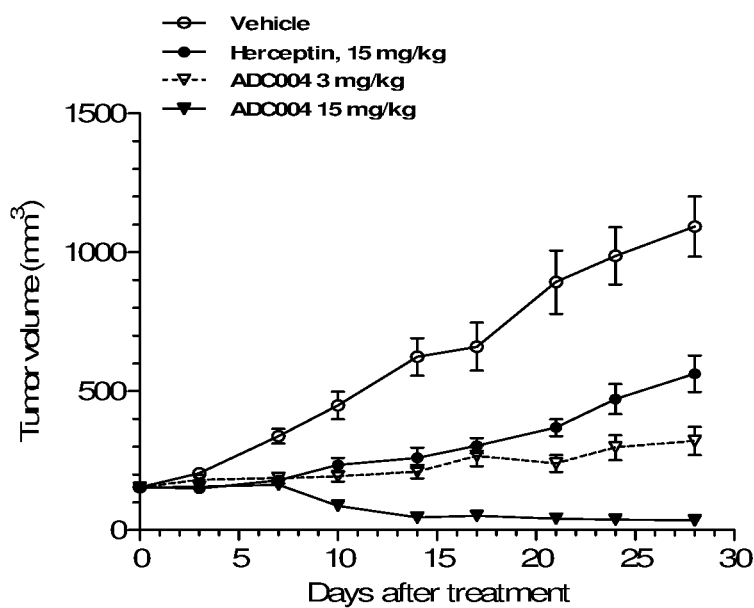
Figure 9:
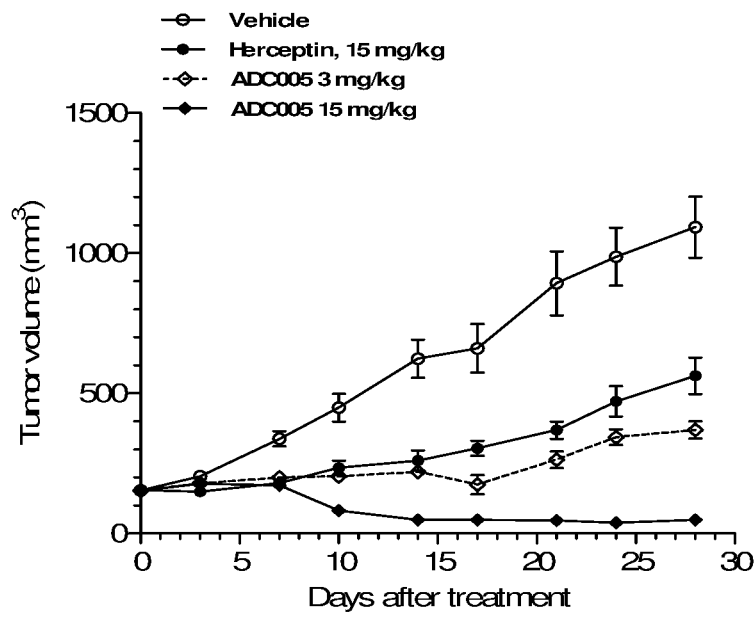
Figure 10:
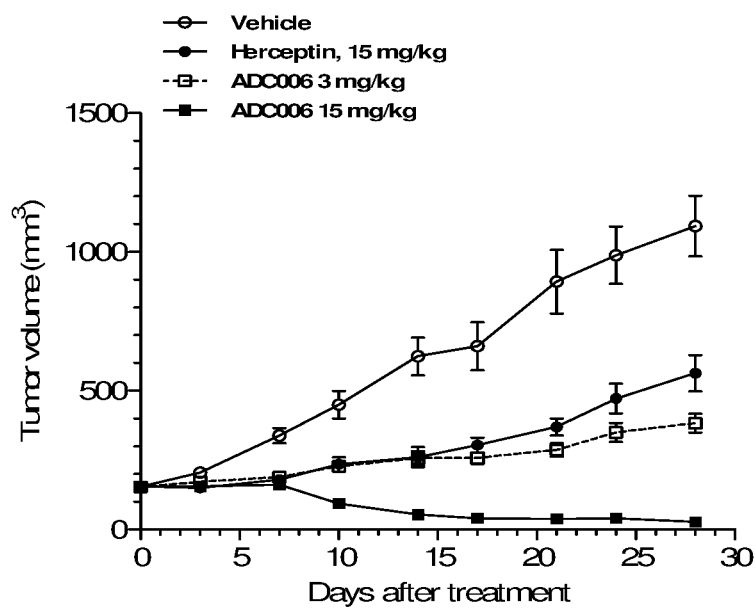
Figure 11:
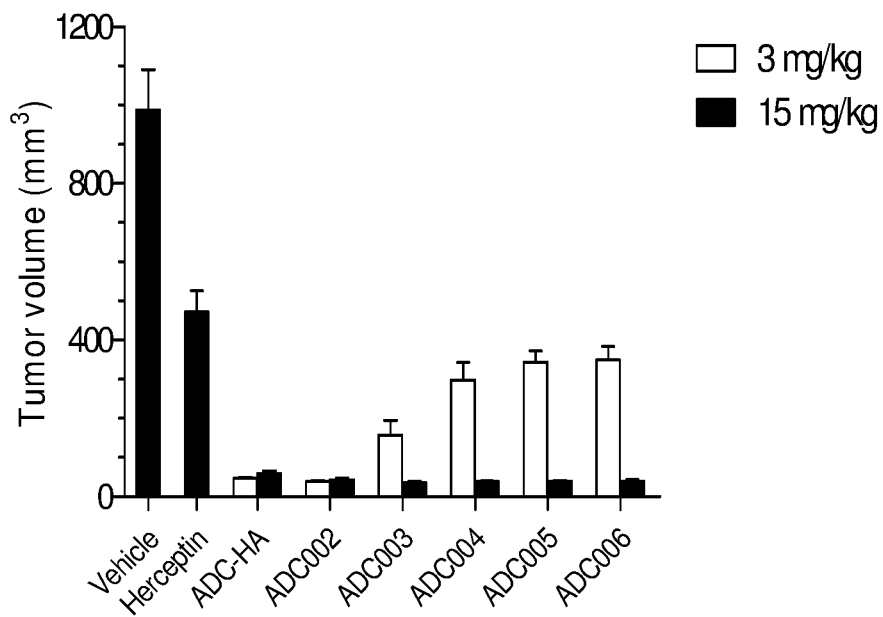
FIG. 11 showed the comparison of tumor sizes at termination of the study between control ADC-HA and ADCC-002 to ADC006.
Figure 12:
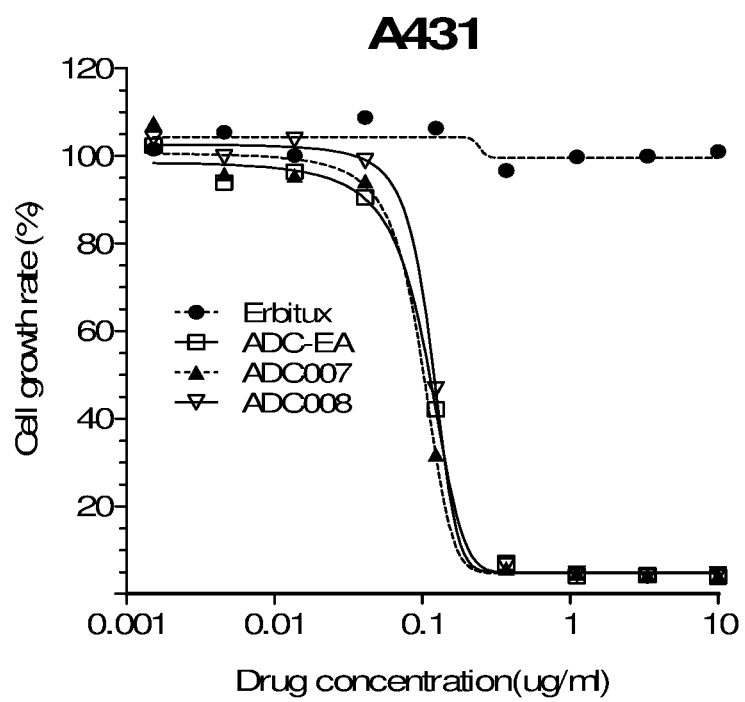

FIG. 12 showed the antiproliferative activity of Erbitux, control ADC-EA, ADC007 (EXAMPLE 15) and ADC008 (EXAMPLE 16).

Figure 13:
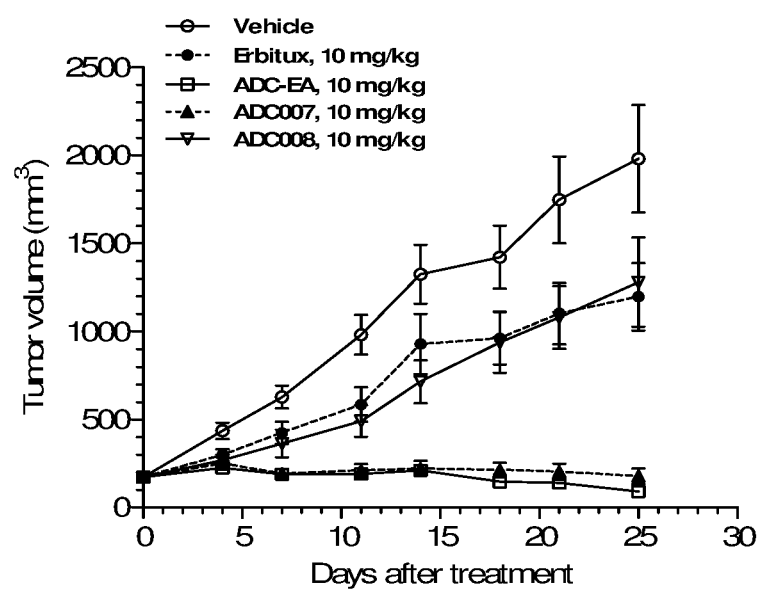

FIG. 13 showed the tumor growth curves for control ADC-EA, ADC007 (EXAMPLE 15) and ADC008 (EXAMPLE 16).

DETAILED DESCRIPTION OF THE PREFERRED EMBODIMENT

To describe the present invention in more detail, the following examples are provided. However, the scope of the present invention is not limited to these.

INTERMEDIATE 1

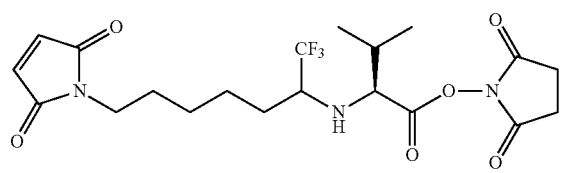 [SMILES: CC(C)[C@H](NC(CCCCCN1C(=O)C=CC1=O)C(F)(F)F)C(=O)ON1C(=O)CCC1=O]

(2S)-2,5-Dioxopyrrolidin-1-yl-2-{[7-(2,5-dioxo-2,5-dihydro-1H-pyrrol-1-yl)-1,1,1-trifluoro-heptan-2-yl]amino}-3-methylbutanoate Step 1: (2S)-3-Methyl-2-[(1,1,1-trifluorooct-7-en-2-yl)amino]butan-1-ol

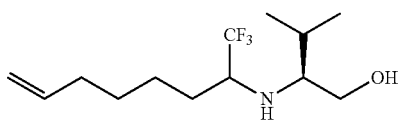 [SMILES: C=CCCCCC(N[C@H](CO)C(C)C)C(F)(F)F]

To a stirred suspension of Mg (10.2 g, 420 mmol) with a few small crystals of iodine in 80 mL of THF was added a small portion of a solution of 6-bromohex-1-ene (22.8 g, 140 mmol) in anhydrous THF (40 mL). After the reaction initiated, the remaining 6-bromohex-1-ene THF solution was added dropwise at a rate to maintain a gentle refluxing. After complete addition, the resulting mixture was heated at 70° C. for 1 h. The Grignard reagent (~120 mL in THF) obtained was then used directly for the next step.

The Grignard reagent from above was cooled to −78° C. and a solution of (4S)-4-isopropyl-2-(trifluoromethyl)oxazolidine (17 g, 93.4 mmol) in THF (40 mL) was added dropwise. The resulting mixture was warmed up to 0° C. and stirred for 1.5 h. The reaction was quenched with sat. $NH_4Cl$ (50 mL), extracted with EtOAc (4×100 mL). The organic phase was dried over $Na_2SO_4$, filtered and concentrated. The residue was purified by flash column chromatography elution with Pet. ether/EtOAc (0-4%) to give the title compound (11.5 g, 46%) as a yellow oil.

Step 2: (2S)-3-Methyl-2-[(1,1,1-trifluorooct-7-en-2-yl)amino]butanoic acid

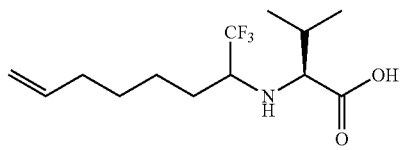 [SMILES: C=CCCCCC(N[C@H](C(=O)O)C(C)C)C(F)(F)F]

To a solution of $H_5IO_6$ (33.2 g, 145.8 mmol) in anhydrous $CH_3CN$ (100.0 mL) was added $CrO_3$ (486 mg, 4.86 mmol) and stirred at room temperature for 1 h. The mixture was then cooled to 0° C. and a solution of (2S)-3-methyl-2-[(1,1,1-trifluorooct-7-en-2-yl)amino]-butan-1-ol (6.5 g, 24.3 mmol, in 20 ml $CH_3CN$) was added dropwise. The resulting mixture was stirred at 0° C. for 1.5 h, quenched with $K_2HPO_4$ (16.3 g in 50 mL of $H_2O$) and extracted with EtOAc (3×100 mL). The combined organic phases were washed with brine, dried over $Na_2SO_4$, filtered and concentrated. The residue was purified by flash column chromatography elution with Pet. ether/EtOAc (0-4%-10% EtOAc) to give the title compound (1.04 g, 12.7%) as a yellow oil.

Step 3: (2S)-Tert-butyl 3-methyl-2-[(1,1,1-trifluorooct-7-en-2-yl)amino]butanoate

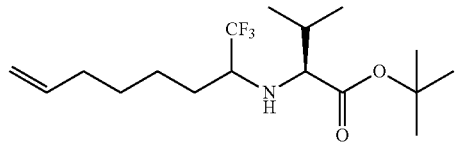 [SMILES: C=CCCCCC(N[C@H](C(=O)OC(C)(C)C)C(C)C)C(F)(F)F]

To a solution of (2S)-3-methyl-2-[(1,1,1-trifluorooct-7-en-2-yl)amino]butanoic acid (650 mg, 2.3 mmol) in t-BuOAc (10.0 mL) was added dropwise 70% $HClO_4$ (398 mg, 2.8 mmol) at 0° C. and stirred for 1 h at this temperature. After warming to room temperature and further stirred for 16 h, the reaction mixture was poured into EtOAc (50 mL), washed successively with $H_2O$ (30 mL), sat. aq. $NaHCO_3$, (30 ml), and brine, dried over $Na_2SO_4$, filtered, and concentrated. The residue was purified by flash column chromatography elution with Pet. ether/EtOAc (0~2%~5%~10% EtOAc) to give the title compound (0.56 g, 72%) as a colorless oil.

Step 4: (2S)-Tert-butyl 3-methyl-2-[(1,1,1-trifluoro-7-hydroxyheptan-2-yl)amino]butanoate

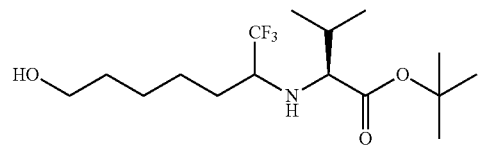 [SMILES: CC(C)[C@H](NC(CCCCCO)C(F)(F)F)C(=O)OC(C)(C)C]

To a solution of (2S)-tert-butyl 3-methyl-2-[(1,1,1-trifluorooct-7-en-2-yl)amino]-butanoate (1.4 g, 4.2 mmol) in anhydrous DCM (6 mL) and MeOH (6 mL) was cooled to −78° C. and charged with $O_3$ for 2 min. The mixture was then warmed to 0° C. and NaBH₄ (481 mg, 12.7 mmol) was added. The resulting mixture was stirred at the same temperature for 2 h, quenched with sat. aq NH₄Cl (4 mL), dried over Na₂SO₄, filtered and concentrated. The residue was purified by flash column chromatography elution with Pet. ether/EtOAc (4%~10% EA) to give the title compund 7 (1.05 g, 72%) as a colourless oil.

¹H NMR (CDCl₃) δ 3.63 (t, J=6.5 Hz, 2H), 3.06 (d, J=6.0 Hz, 1H), 3.01 (d, J=4.6 Hz, 1H), 2.90-2.79 (m, 1H), 1.92-1.80 (m, 1H), 1.67-1.55 (m, 5H), 1.44 (s, 8H), 1.42-1.31 (m, 3H), 0.95-0.83 (m, 6H).

Step 5: (2S)-Tert-butyl 2-((7-(2,5-dioxo-2,5-dihydro-1H-pyrrol-1-yl)-1,1,1-trifluoroheptan-2-yl)amino)-3-methylbutanoate

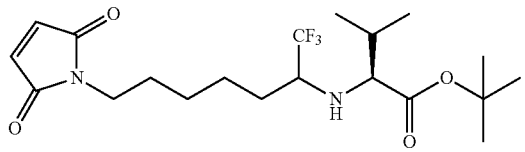 [SMILES: CC(C)[C@H](NC(CCCCCN1C(=O)C=CC1=O)C(F)(F)F)C(=O)OC(C)(C)C]

To a solution of triphenyl phosphine (845 mg, 3.2 mmol) in THF (35 mL) at −78° C. under N₂ was added DIAD (651 mg, 3.2 mmol) dropwise. The yellow reaction mixture was stirred at −78° C. for 5 min and (2S)-tert-butyl 3-methyl-2-[(1,1,1-trifluoro-7-hydroxyheptan-2-yl)amino]butanoate (1.1 g, 3.22 mmol) in THF (5 mL) was added. After further stirring for 5 min, neopentyl alcohol (142 mg, 1.61 mmol) and 1H-pyrrole-2,5-dione (313 mg, 3.22 mmol) were added to the reaction mixture as solids. The reaction was then stirred overnight at ambient temperature and concentrated. The residue was purified by flash column chromatography elution with Pet. ether/EtOAc (0~15% EtOAc) to give the title compound (550 mg, 40.7%) as a colorless oil.

¹H NMR (CDCl₃) δ 6.69 (s, 2 H), 3.52 (t, J=7.2 Hz, 2 H), 3.06-3.01 (m, 1 H), 2.84-2.82 (m, 1 H), 1.89-1.87 (m, 1 H), 1.66-1.52 (m, 8 H), 1.50-1.25 (m, 9 H), 0.95-0.86 (m, 6 H).

Step 6: (2S)-2,5-Dioxopyrrolidin-1-yl-2-{[7-(2,5-dioxo-2,5-dihydro-1H-pyrrol-1-yl)-1,1,1-trifluoroheptan-2-yl]amino}-3-methylbutanoate

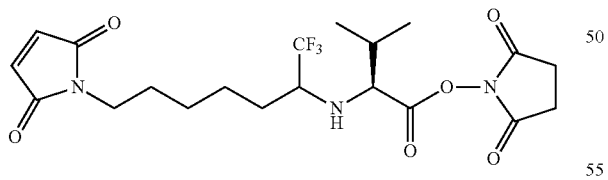

To a solution of (2S)-tert-butyl 2-((7-(2,5-dioxo-2,5-dihydro-1H-pyrrol-1-yl)-1,1,1-trifluoroheptan-2-yl)amino)-3-methylbutanoate (350 mg, 0.84 mmol) in anhydrous DCM (6 mL) under N₂ at 0° C. was added TFA (6 mL) dropwise. The resulting mixture was stirred at room temperature for 2 h, concentrated and co-evaporated with toluene (2×10 mL) to remove TFA. The residue was then re-dissloved in anhydrous THF (5 mL) under N₂ at 0° C., and triethylamine (251 mg, 2.492 mmol) was added followed by DCC (171 mg, 0.83 mmol). After stirring at room temperature for 5 min, N-hydroxysuccinimide (96 mg, 0.83 mmol) was added. The mixture was stirred at room temperature for 16 h, filtered and concentrated to give the crude title compound (260 mg), which was used for next reaction step without further purification.

INTERMEDIATE 2 & INTERMEDIATE 3

INTERMEDIATE 2

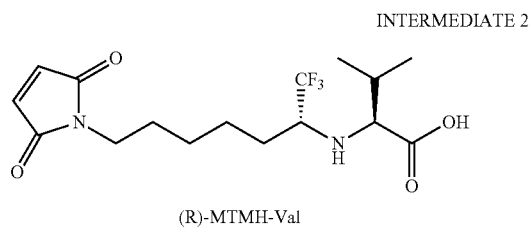

(R)-MTMH-Val

INTERMEDIATE 3

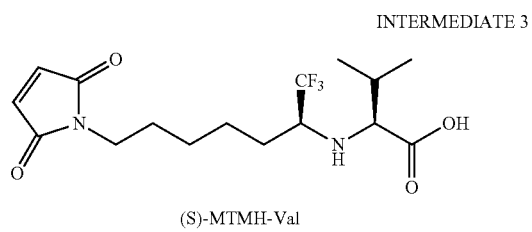

(S)-MTMH-Val (S)-2-(((R)-7-(2,5-dioxo-2,5-dihydro-1H-pyrrol-1-yl)-1,1,1-trifluoroheptan-2-yl)amino)-3-methyl-butanoic acid, (R)-MTMH-Val and (S)-2-(((S)-7-(2,5-dioxo-2,5-dihydro-1H-pyrrol-1-yl)-1,1,1-trifluoroheptan-2-yl)amino)-3-methylbutanoic acid, (S)-MTMH-Val Step 1:
(4S)-4-isopropyl-2-(trifluoromethyl)oxazolidine

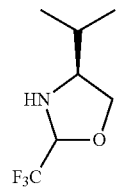

To a mixture of (S)-2-amino-3-methylbutan-1-ol (85 g, 824 mmol, 1.0 eq) and 2, 2, 2-trifluoro-1-methoxy-ethanol (75 g, 577 mmol, 0.7 eq) in toluene (1.5 L) was added PPTS (10.4 g, 41.2 mmol, 0.05 Eq) in one portion at room temperature under N₂. The mixture was refluxed for 3 h with azeotropic removal of methanol/water (Dean-Stark trap). TLC showed the reaction was complete. The mixture was cooled to room temperature, filtered and concentrated in vacuum to afford the title compound (86 g, crude) as a yellow oil.

Step 2: (2S)-3-Methyl-2-[(1,1,1-trifluorooct-7-en-2-yl)amino]butan-1-ol

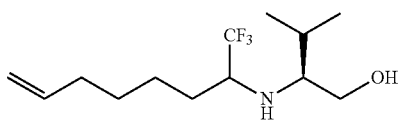 [SMILES: C=CCCCCC(N[C@H](CO)C(C)C)C(F)(F)F]

To a mixture of magnesium (18.2 g, 750 mmol, 1.5 eq) and I₂ (cat) in THF (500 mL) was added dropwise a solution of 6-bromohex-1-ene (81.5 g, 499.8 mmol, 1.0 eq) in THF (500 mL) at 20° C. over a period of 30 min under N₂. During the addition, the reaction temperature risen and was maintained at 60° C. After further stirring at 60° C. for another 1.5 h, the mixture was cooled to room temperature and used for the next step without purification.

To Grignard reagent, bromo(hex-5-enyl) magnesium (0.5 M, 500 mL, 1.25 eq) from above at −78° C. under N₂ was added dropwise a solution of (4S)-4-isopropyl-2-(trifluoromethyl)oxazolidine (36.6 g, 200 mmol, 1.00 eq) in THF (300 mL). The mixture was stirred at −78° C. for 30 min, then warmed to 20° C. and stirred for 4.5 h. TLC (PE:EA=5:1) showed the reaction was complete. The mixture was quenched with NH₄Cl (500 mL) and extracted with EtOAc (1000 mL×3). The combined organic phases were washed with saturated brine (500 mL×2), dried with anhydrous Na₂SO₄, filtered and concentrated. The residue was purified by silica gel chromatography (Pet. ether:EtOAc=20:1) to afford the title compound (19 g, 35.5% yield) as a yellow oil.

Step 3: (2S)-3-Methyl-2-[(1,1,1-trifluorooct-7-en-2-yl)amino]butanoic acid

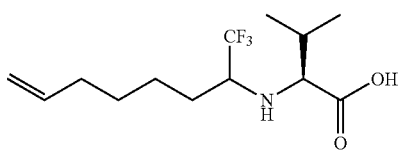 [SMILES: C=CCCCCC(N[C@H](C(=O)O)C(C)C)C(F)(F)F]

To a mixture of (2S)-3-methyl-2-[(1,1,1-trifluorooct-7-en-2-yl)amino]butan-1-ol (19 g, 71 mmol, 1 eq) in CH₃CN (515 mL) was added pentahydroxy(oxo)-iodane (48.6 g, 213.2 mmol, 3 eq), CrO3 (142 mg, 1.4 mmol, 0.02 eq) and water (4 mL) at WC. The mixture was stirred at 0° C. for 4 h. TLC showed the reaction was complete. The mixture was concentrated in vacuum. The residue was purified by silica gel chromatography (Pet. ether:EtOAc=10:1) to afford the title compound (16 g, 80% yield) as a yellow oil.

Step 4: (2S)-Tert-butyl 3-methyl-2-[(1,1,1-trifluorooct-7-en-2-yl)amino]butanoate

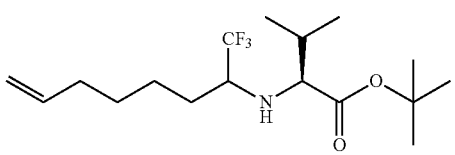 [SMILES: C=CCCCCC(N[C@H](C(=O)OC(C)(C)C)C(C)C)C(F)(F)F]

To a mixture of (2S)-3-methyl-2-[(1,1,1-trifluorooct-7-en-2-yl)amino]butanoic acid (7 g, 24.9 mmol, 1 eq) in tert-butyl acetate (200 mL) was added 70% HClO₄ (7.5 g, 74.7 mmol, 3 eq) in one portion at 30° C. under N₂. The mixture was stirred at 30° C. for 3 h. TLC showed the reaction was complete. The mixture was diluted with EtOAc (400 mL) and washed with water (400 mL). The organic layer was dried over Na₂SO₄ and concentrated. The residue was purified by silica gel chromatography (Pet. ether:EtOAc=60:1) to afford the title compound (7 g, 83.4% yield) as yellow oil.

Step 5: (2S)-Tert-butyl 3-methyl-2-[(1,1,1-trifluoro-7-hydroxyheptan-2-yl)amino]butanoate

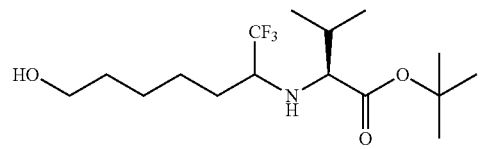 [SMILES: CC(C)[C@H](NC(CCCCCO)C(F)(F)F)C(=O)OC(C)(C)C]

Ozone was bubbled into a solution of (2S)-tert-butyl 3-methyl-2-[(1,1,1-trifluorooct-7-en-2-yl)amino]butanoate (14.0 g, 41.5 mmol, 1 eq) in DCM (100 mL) and MeOH (10 mL) at −78° C. for 3 min. After excess O₃ was purged by N₂, NaBH₄ (4.7 g, 124.5 mmol, 3 eq) was added at 0° C. The mixture was stirred at 20° C. for 3 h. TLC showed starting material was consumed completely. After quenched by saturated aqueous NH₄Cl (50 mL), the mixture was extracted with EtOAc (200 mL). The organic layer was concentrated to give the crude product. The crude product was purified by silica gel chromatography eluted with (Pet. ether:EtOAc=20:1) to give the title compound (11 g, 77.7% yield) as a yellow oil.

Step 6: (2S)-Tert-butyl 2-((7-(2,5-dioxo-2,5-dihydro-1H-pyrrol-1-yl)-1,1,1-trifluoroheptan-2-yl)amino)-3-methylbutanoate

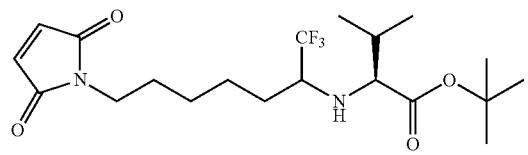

To a solution of PPh₃ (4.61 g, 17.57 mmol, 1.50 eq) in THF (40 mL) at −78° C. under N₂ was added dropwise DIAD (3.55 g, 17.57 mmol, 1.50 eq). After stirred at −78° C. for 5 min, (2S)-tert-butyl 3-methyl-2-[(1,1,1-trifluoro-7-hydroxyheptan-2-yl)amino]butanoate (4.0 g, 11.7 mmol, 1 eq) in THF (5 mL) was added and stirred for 5 min. Followed 2, 2-dimethylpropan-1-ol (774.6 mg, 8.8 mmol, 0.75 eq) and 1H-pyrrole-2,5-dione (1.7 g, 17.6 mmol, 1.5 eq) were added to the reaction mixture as solids. The reaction was stirred for 3 h at 30° C. TLC showed the starting material was consumed. The mixture was concentrated and purified with silica gel column (Pet. ether:EtOAc=10:1) to give the title compound (4.00 g, 9.51 mmol, 81.17% yield) as a white solid.

Step 7: (S)-2-(((R)-7-(2,5-dioxo-2,5-dihydro-1H-pyrrol-1-yl)-1,1,1-trifluoroheptan-2-yl)amino)-3-methyl-butanoic acid, (R)-MTMH-Val and (S)-2-(((S)-7-(2,5-dioxo-2,5-dihydro-1H-pyrrol-1-yl)-1,1,1-trifluoroheptan-2-yl)amino)-3-methylbutanoic acid, (S)-MTMH-Val

INTERMEDIATE 2

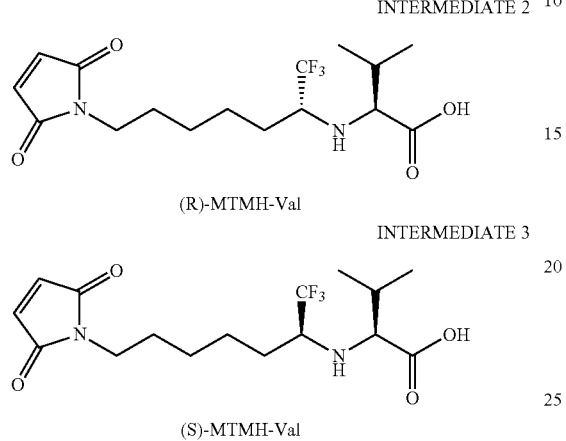

(R)-MTMH-Val

INTERMEDIATE 3

(S)-MTMH-Val

A mixture of (2S)-tert-butyl 2-((7-(2,5-dioxo-2,5-dihydro-1H-pyrrol-1-yl)-1,1,1-trifluoro-heptan-2-yl)amino)-3-methylbutanoate (6.0 g, 14.3 mmol, 1 eq) in DCM (40 mL) and TFA (40 mL) was stirred at 30° C. for 12 h. The mixture was then concentrated and purified by prep-HPLC (Instrument: Shimadzu pump LC-20A; Column: SYNERGI 200*50 10 um; Mobile phase: A for H2O (Add 0.75% TFA, v/v) and B for CH3CN; Gradient: B 30-60%; Gradient Time: 30 min; Retention Time: 25-30 min; Flow rate: 80 mL/min) to afford peak 1: INTERMEDIATE 2 (3.20 g, 8.78 mmol, 61.55% yield) as a white solid and peak 2, INTERMEDIATE 3 (1.10 g, 3.02 mmol, 21.16% yield) as a yellow oil.

INTERMEDIATE 2, (R)-MTMH-Val: $^1$H NMR (CDCl$_3$) δ 6.72 (s, 2H), 3.54 (t, 2H), 3.30 (d, 1H), 3.00 (m, 1H), 2.13 (m, 1H), 1.75-1.25 (m, 8H), 1.03 (d, 3H), 0.98 (d, 3H). LCMS: 365.1 (MO.

INTERMEDIATe 3, (S)-MTMH-Val: $^1$H NMR (CDCl$_3$) δ 6.72 (s, 2H), 3.54 (t, 2H), 3.33 (d, 2H), 2.97 (m, 1H), 2.02 (m, 1H), 1.75-1.25 (m, 8H), 1.03 (d, 3H), 0.99 (d, 3H). LCMS: 365.1 (MH$^+$).

INTERMEDIATE 4

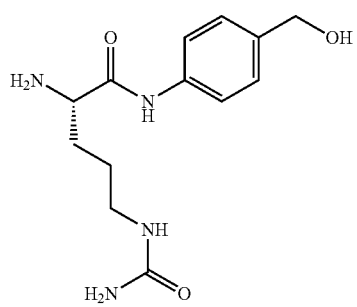 [SMILES: NC(=O)NCCC[C@H](N)C(=O)Nc1ccc(CO)cc1]

Cit-PAB-OH

Step 1: Fmoc-Cit

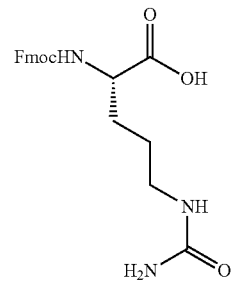

To a solution of L-citrulline (20.00 g, 114.16 mmol, 1.00 eq) in 10% Na$_2$CO$_3$ (200 mL) was added dropwise a solution of Fmoc-Cl (35.40 g, 136.84 mmol, 1.20 Eq) in dioxane (100 mL) at 0° C. over a period of 5 min under N$_2$. The reaction mixture was warmed to 20° C. for 4 h. TLC showed the starting material was consumed completely. The reaction mixture was added H$_2$O (50 mL). The aqueous phase was separated and adjusted to PH 2~3 with 2M HCl (50 mL). The mixture was extracted with EtOAc (150 mL×3). The combined organic phases were washed with saturated brine (100 mL×2), dried over anhydrous Na$_2$SO$_4$, filtered and concentrated to give the title compound (40.00 g, 100.65 mmol, 88.17% yield) as a white solid. LCMS(ESI): 398.1 (MH$^+$).

Step 2: Fmoc-Cit-PAB-OH

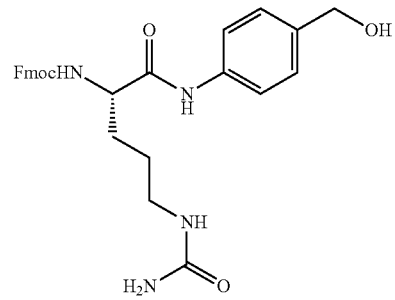

To a solution of Fmoc-cit (40.00 g, 100.65 mmol, 1.00 Eq) and 4-aminobenzyl alcohol (14.87 g, 120.78 mmol, 1.2 eq) in DCM (1000 mL) was added dropwise a solution of EEDQ (49.78 g, 201.30 mmol, 2.0 eq) in MeOH (500 mL) at 20° C. over a period of 30 min under N$_2$. The reaction mixture was stirred at 20° C. for 16 h. TLC (MeOH: EtOAc=1:10) showed the starting material was consumed completely. The reaction mixture was concentrated and the residue was washed with tert-butyl methyl ether (200 mL×3), filtered and concentrated to give the crude title compound (45.00 g, 89.54 mmol, 88.96% yield) as a white solid.

Step 3: Cit-PAB-OH

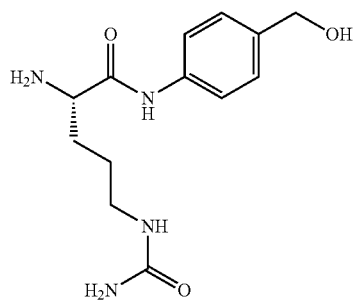 [SMILES: NC(=O)NCCC[C@H](N)C(=O)Nc1ccc(CO)cc1]

To a solution of Fmoc-cit-PAB-OH (15.00 g, 29.85 mmol, 1.00 Eq) in DMF (124.5 mL) was added dropwise a solution of piperidine (21.93 g, 257.58 mmol, 8.63 Eq) in DMF (20 mL) at 20° C. over a period of 10 min. The reaction mixture was stirred at 20° C. for 3 h. TLC (DCM:MeOH=5:1) showed the starting material was consumed completely. The reaction was washed with DMF (30 mL×2). The combined organic phases were concentrated to give the residue which was purified by pre-HPLC (formic acid) to give the title compound (7.50 g, 26.76 mmol, 89.63% yield) as a white solid. LCMS(ESI): 218.1 (MH$^+$).

INTERMEDIATE 5

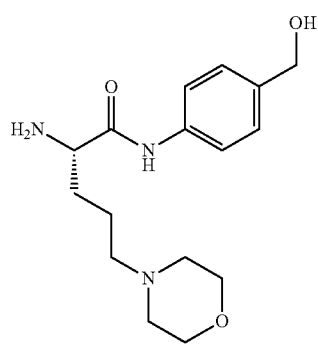 [SMILES: N[C@@H](CCCN1CCOCC1)C(=O)Nc1ccc(CO)cc1]

(S)-2-Amino-N-(4-(hydroxymethyl)phenyl)-5-morpholinopentanamide

Step 1: (S)-Methyl 2-(((benzyloxy)carbonyl)amino)-5-morpholino-5-oxopentanoate

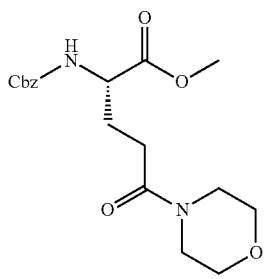 [SMILES: COC(=O)[C@H](CCC(=O)N1CCOCC1)NC(=O)OCc1ccccc1]

To a solution of Z-Glu-OMe (10 g, 33.87 mmol) in dry DMF (100 mL) was added DIPEA (13.13 g, 101.60 mmol), HATU (15.45 g, 40.64 mmol) and morpholine (4.43 g, 50.8 mmol) and then stirred at 20° C. for 16 h. The mixture was poured into water (200 ml) and EtOAc (500 ml). The organic layer was separated, washed with water (100 mL×2) and brine (100 mL), dried over anhydrous NaSO$_4$ and concentrated to give the title compound (11 g, crude) as an oil. MS: 365 (MH$^+$)

Step 2: (S)-Methyl 2-(((benzyloxy)carbonyl)amino)-5-morpholinopentanoate

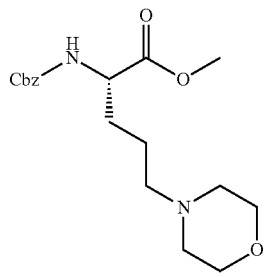 [SMILES: COC(=O)[C@H](CCCN1CCOCC1)NC(=O)OCc1ccccc1]

To a solution of (S)-methyl 2-(((benzyloxy)carbonyl) amino)-5-morpholino-5-oxopentanoate (3 g, 8.2 mmol) in dry THF (40 mL) was added a solution of 10M borane methyl sulfide complex in THF (4 mL) at 0° C. and then stirred at 16° C. for 16 h. The mixture was quenched with CH$_3$OH and followed by 1M aqueous HCl (40 mL), stirred at 90° C. for 30 min and evaporated to dryness. The residue was dissolved with water (100 mL), adjusted to pH 10 with aq NaOH and extracted with EtOAc (100 mL×3). The combined organic layers were washed with brine (50 mL×2), dried over anhydrous NaSO$_4$ and concentrated under reduced pressure. The residue from four parallel reactions were pooled and purified by column chromatography (DCM:MeOH=10:1) to give the title compound (5.5 g, yield 47.7%) as an oil. MS: 351 (MH+)

Step 3: (S)-2-(((Benzyloxy)carbonyl)amino)-5-morpholinopentanoic acid

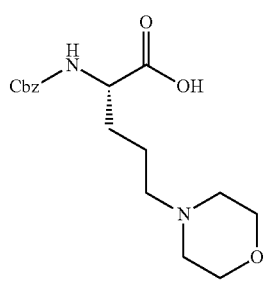 [SMILES: O=C(N[C@@H](CCCN1CCOCC1)C(=O)O)OCc1ccccc1]

To a solution of (S)-methyl 2-(((benzyloxy)carbonyl) amino)-5-morpholinopentanoate (5.5 g, 15.70 mmol) in THF (50 mL) was added LiOH—H$_2$O (1.32 g, 31.39 mmol). Then the mixture was stirred at 0° C. for 2 h and evaporated to dryness to give the crude title compound (5.0 g, crude).

Step 4: (S)-Benzyl (1-((4-(hydroxymethyl)phenyl)amino)-5-morpholino-1-oxopentan-2-yl) carbamate

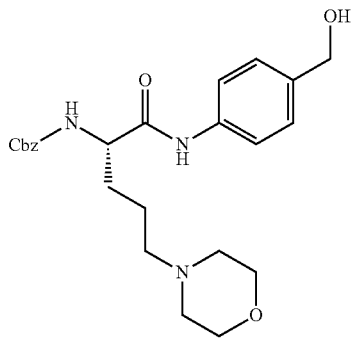 [SMILES: O=C(N[C@@H](CCCN1CCOCC1)C(=O)Nc1ccc(CO)cc1)OCc1ccccc1]

To a solution of (S)-2-(((benzyloxy)carbonyl)amino)-5-morpholinopentanoic acid (3.00 g, 8.92 mmol) in dry DMF (200 mL) was added HOBt (1.21 g, 8.92 mmol), EDCl (1.71 g, 8.92 mmol) and 4-aminobenzyl alcohol (1.65 g, 13.38 mmol and then stirred at 0° C. for 6 h. The mixture was poured into water (100 mL) and EtOAc (150 mL. The organic layer was separated, washed with water (50 mL×2), brine (50 mL), dried over anhydrous NaSO$_4$ and concentrated under reduced pressure. The residue was purified by column chromatography (DCM:MeOH=10:1) to afford the title compound (1.2 g, yield 30.47%). MS: 442 (MH$^+$)

Step 5: (S)-2-Amino-N-(4-(hydroxymethyl)phenyl)-5-morpholinopentanamide

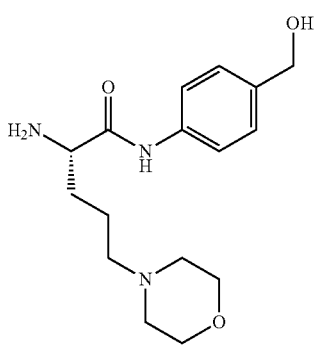 [SMILES: N[C@@H](CCCN1CCOCC1)C(=O)Nc1ccc(CO)cc1]

To a solution of (S)-benzyl (1-((4-(hydroxymethyl)phenyl)amino)-5-morpholino-1-oxopentan-2-yl)carbamate (600.00 mg, 1.36 mmol) in MeOH (50 mL) was added Pd/C (200.00 mg) under N$_2$. The suspension was degassed under vacuum and purged with H$_2$ several times. The mixture was stirred under H$_2$ (15 psi) at 25° C. for 0.5 h. The catalyst was filtered off and the filtrate was concentrated to afford the crude title compound (350.00 mg). MS: 308 (MH$^+$)

INTERMEDIATE 6

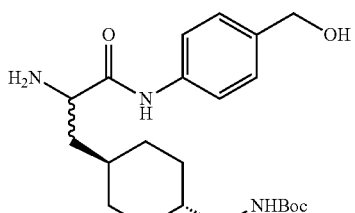

tert-Butyl ((trans-4-(2-amino-3-((4-(hydroxymethyl)phenyl)amino)-3-oxopropyl)cyclo hexyl)methyl) carbamate Step 1: Trans-4-(((tert-Butoxycarbonyl)amino)methyl)cyclohexanecarboxylic acid

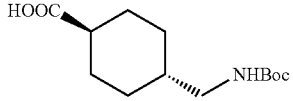

To a mixture of trans-4-(aminomethyl)cyclohexanecarboxylic acid (50 g, 318 mmol) and Boc$_2$O (69.4 g, 318 mmol) in H$_2$O (500 mL) was added a solution of NaOH (12.7 g, 318 mmol) in H$_2$O (500 mL) in one portion at 15° C. under N$_2$. The mixture was stirred at 15° C. for 16 h. TLC showed most starting material was consumed. The mixture was adjusted to pH 3 with HOAc (40 mL) and extracted with EtOAc (400 mL×3). The combined organic phases were dried with anhydrous Na$_2$SO$_4$, filtered and concentrated to afford the crude title compound (77 g) as a white solid.

$^1$H NMR (CDCl$_3$) δ 4.62 (m, 1H), 2.98 (m, 2H), 2.25 (m, 1H), 2.04 (d, 2H), 1.83 (d, 2H), 1.438-1.37 (m, 12H), 0.96 (m, 2H).

Step 2: tert-Butyl ((trans-4-(hydroxymethyl)cyclohexyl)methyl)carbamate

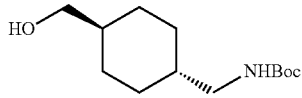 [SMILES: CC(C)(C)OC(=O)NC[C@H]1CC[C@H](CO)CC1]

To a mixture of trans-4-(((tert-Butoxycarbonyl)amino)methyl)cyclohexanecarboxylic acid (37.0 g, 143.8 mmol) in THF (1 L) was added LiAlH4 (8.2 g, 215.7 mmol) at 0° C. under N$_2$. The mixture was stirred at 15° C. for 16 h. TLC showed the reaction was completed. The mixture was quenched with water (8.2 mL), followed by 15% aqueous NaOH solution (8.2 mL), water (24.6 mL) and filtered. The filtrate was concentrated and the residue was purified by silica gel chromatography (Pet.ether:EtOAc=2:1) to afford the title compound (19.0 g, 54.3% yield) as a white solid.

$^1$H NMR (CDCl$_3$) δ 4.61 (br s, 1H), 3.45 (d, 2H), 2.98 (t, 2H), 1.81 (m, 4H), 1.44 (m, 11H), 0.95 (m, 4H).

Step 3: tert-Butyl ((trans-4-formylcyclohexyl)methyl)carbamate

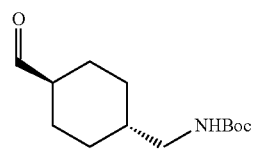 [SMILES: CC(C)(C)OC(=O)NC[C@H]1CC[C@H](C=O)CC1]

To a mixture of oxalyl chloride (11.9 g, 93.7 mmol) in DCM (375 mL) was added a solution of DMSO (11.0 g, 140.5 mmol) in DCM (675 mL) at −65° C. under N$_2$. The mixture was stirred at −65° C. for 30 min. A solution of tert-butyl ((trans-4-(hydroxymethyl)cyclohexyl)methyl)carbamate (19.00 g, 78.08 mmol) in DCM (150 mL) was then added at −65° C. The mixture was further stirred at −65° C. for another 30 min. TLC showed most starting material was consumed. A solution of Et₃N (19.4 g, 191.3 mmol) in DCM (75 mL) was added at −65° C. and stirred for 30 min. The mixture was warmed to 20° C., quenched with sat.NH₄Cl solution (150 mL) and extracted with DCM (300 mL×3). The combined organic phases were dried with anhydrous Na₂SO₄, filtered and concentrated to afford the crude title compound (19 g) as yellow oil.

Step 4: Methyl 2-(((benzyloxy)carbonyl)amino)-3-(trans-4-(((tert-butoxycarbonyl)amino)methyl)cyclo-hexyl)acrylate

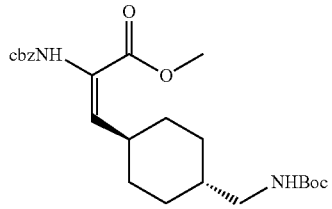

To a mixture of tert-butyl ((trans-4-formylcyclohexyl)methyl)carbamate (19.0 g, 78.7 mmol) and methyl 2-(((benzyloxy)carbonyl)amino)-2-(dimethoxyphosphoryl)acetate (28.7 g, 86.6 mmol) in DCM (600 mL) was added DBU (18.0 g, 118.1 mmol) in one portion at 20° C. under N₂. The mixture was stirred at 20° C. for 2 h. TLC showed the reaction was completed. The mixture was washed with saturated NaHCO₃ (300 mL×2). The organic layer was concentrated and the residue was purified by silica gel chromatography (Pet. ether:EtOAc=3:1) to afford the title compound (20 g, 56.9% yield) as a colorless oil.
¹H NMR (CDCl₃) δ 7.35 (m, 5H), 6.45 (d, 1H), 6.08 (br s, 1H), 5.15 (s, 2H), 4.60 (br s, 1H), 3.74 (s, 3H), 2.97 (m, 2H), 2.32 (m, 1H), 1.77 (m, 4H), 1.45 (s, 9H), 1.12 (m, 2H), 0.95 (m, 3H).

Step 5: 2-(((Benzyloxy)carbonyl)amino)-3-(trans-4-(((tert-butoxycarbonyl)amino)methyl)cyclo-hexyl)acrylic acid

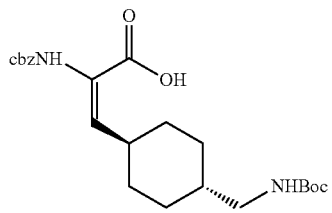

To a mixture of methyl 2-(((benzyloxy)carbonyl)amino)-3-(trans-4-(((tert-butoxycarbonyl) amino)methyl)cyclohexyl)acrylate (20.0 g, 44.8 mmol) in MeOH (150 mL) was added LiOH.H₂O (5.6 g, 134.4 mmol) in H₂O (50 mL) at 25° C. under N₂. The mixture was stirred at 25° C. for 16 h. TLC showed the reaction was completed. The mixture was adjusted to pH 3 with HOAc and concentrated to remove MeOH. The aqueous phase was extracted with ethyl acetate (50 mL×3). The combined organic phases were dried with anhydrous Na₂SO₄, filtered and concentrated to afford the crude title compound (18.00 g) as a colorless oil.

Step 6: Benzyl (1-(trans-4-((((tert-butoxycarbonyl)amino)methyl)cyclohexyl)-3-((4-(hydroxylmethyl)phenyl)amino)-3-oxoprop-1-en-2-yl)carbamate

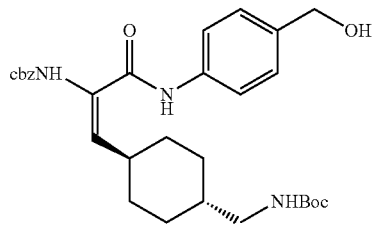

A mixture of 2-(((Benzyloxy)carbonyl)amino)-3-(trans-4-(((tert-butoxycarbonyl)amino)methyl)cyclohexyl)acrylic acid (18.0 g, 41.6 mmol), 4-aminobenzyl alcohol (7.7 g, 62.4 mmol), HATU (23.7 g, 62.4 mmol) and DIPEA (16.1 g, 124.9 mmol) in DMF (600 mL) was stirred at 25° C. for 16 h under N₂. TLC showed the reaction was completed. The mixture was diluted with ethyl acetate (600 mL) and washed with sat.NH₄Cl solution (600 mL×3). The organic layer was separated, dried with anhydrous Na₂SO₄, filtered and concentrated. The residue was purified by silica gel chromatography (Pet. ether:EtOAc=1:1) to afford the title compound (14.00 g, 26.04 mmol, 62.56% yield) as a brown solid. MS: 538 (MH⁺).

Step 7: tert-Butyl ((trans-4-(2-amino-3-((4-(hydroxymethyl)phenyl)amino)-3-oxopropyl)cyclohexyl)methyl)carbamate

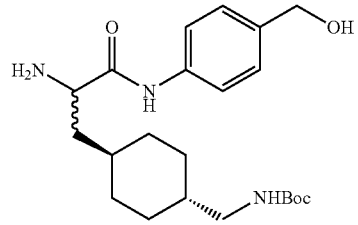 [SMILES: CC(C)(C)OC(=O)NC[C@H]1CC[C@H](CC(N)C(=O)Nc2ccc(CO)cc2)CC1]

To a solution of Benzyl (1-(trans-4-((((tert-butoxycarbonyl)amino)methyl)cyclohexyl)-3-((4-(hydroxylmethyl)phenyl)amino)-3-oxoprop-1-en-2-yl)carbamate (7.0 g, 13.0 mmol) in MeOH (100 mL) was added 10% Pd/C (1.0 g) under N₂. The suspension was degassed under vacuum and purged with H₂ several times. The mixture was stirred under H₂ (15psi) at 25° C. for 20 min. TLC showed the starting material was consumed completely. The reaction mixture was filtered and the filtrate was concentrated. The residue was purified by prep-HPLC to give the title compound (1.4 g, 26.3% yield) as a white solid. MS: 406 (MH⁺)

INTERMEDIATE 7

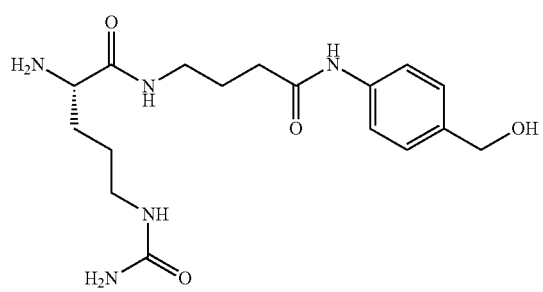 [SMILES: NC(=O)NCCC[C@H](N)C(=O)NCCCC(=O)Nc1ccc(CO)cc1]

Cit-ABA-PAB-OH

Step 1: 4-((((9H-Fluoren-9-yl)methoxy)carbonyl)amino)butanoic acid

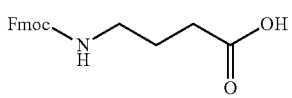

To a mixture of 4-aminobutanoic acid (5.0 g, 48.5 mmol, 1 eq) in 10% aqueous $Na_2CO_3$ solution (16.5 g, 155.7 mmol, 3.2 eq, 150 mL $H_2O$) was added dropwise a solution of (9H-fluoren-9-yl)methyl carbonochloridate (13.8 g, 53.3 mmol, 1.1 eq) in dioxane (100 mL) at 0° C. over a period of 10 min under $N_2$. The mixture was stirred at 20° C. for 4 h. TLC showed the reaction was completed. The mixture was separated and adjusted to PH 2-3 with 2M HCl and extracted with EtOAc (250 mL×3). The combined organic phases were washed with saturated brine (150 mL×2), dried over anhydrous $Na_2SO_4$, filtered and concentrated in vacuum to afford the crude title compound (16 g) as a white solid. LCMS: 326.1 ($MH^+$)

Step 2: (9H-Fluoren-9-yl)methyl (4-((4-(hydroxymethyl)phenyl)amino)-4-oxobutyl)carbamate

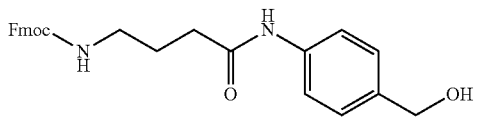

To a solution of 4-((((9H-fluoren-9-yl)methoxy)carbonyl)amino)butanoic acid (16.0 g, 49 mmol, 1 eq) in DMF (200 mL) was added then HATU (20.6 g, 54.1 mmol, 1.1 eq) and DIPEA (19.1 g, 147.5 mmol, 3 eq) at 20° C. and stirred for 30 min. Then 4-aminobenzyl alcohol (7.3 g, 59.0 mmol, 1.2 eq) was added in one portion at 20° C. The mixture was stirred at 20° C. for 16 h. TLC showed the reaction was completed. The reaction mixture was concentrated in vacuum. The residue was washed with TBME (300 mL×3), filtered and concentrated to afford the crude title compound (15 g) as a yellow solid. LCMS: 431.2 ($MH^+$)

Step 3: 4-Amino-N-(4-(hydroxymethyl)phenyl)butanamide

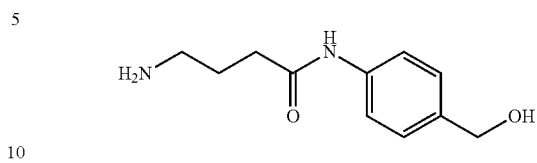

To a solution of (9H-fluoren-9-yl)methyl (4-((4-(hydroxymethyl)phenyl)amino)-4-oxobutyl)-carbamate (5.0 g, 11.6 mmol, 1 eq) in DMF (40 mL) was added piperidine (7.9 g, 92.9 mmol, 8 eq) in one portion at 20° C. Then the mixture was stirred at 20° C. for 3 h. TLC (DCM: MeOH=5:1) showed starting material was consumed completely. The reaction mixture was concentrated to give the crude title compound (5 g) as a yellow solid. LCMS: 209.1 ($MH^+$)

Step 4: Fmoc-Cit-ABA-PAB-OH

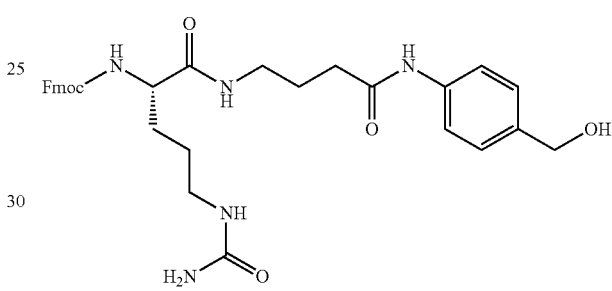

To a solution of 4-amino-N-(4-(hydroxymethyl)phenyl)butanamide (600 mg, 2.9 mmol, 1 eq) and Fmoc-cit (1.3 g, 3.2 mmol, 1.1 eq) in DCM (8 mL) was added slowly a solution of EEDQ (1.4 g, 5.8 mmol, 2 eq) in MeOH (8 mL) at 20° C. The mixture was stirred at 20° C. for 16 h. TLC (DCM:MeOH=5:1) showed the reaction was completed. The reaction mixture was concentrated and the residue was purified by prep-TLC ($SiO_2$, DCM:MeOH=5:1) to give the title compound (440 mg, 26% yield) as a white solid. LCMS: 588.3 ($MH^+$)

Step 5: Cit-ABA-PAB-OH

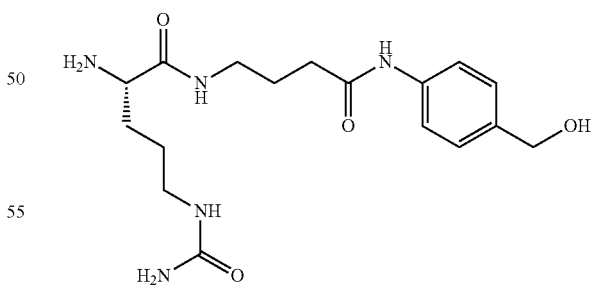

To a solution of Fmoc-Cit-ABA-PAB-OH (440 mg, 749 umol, 1 Eq) in DMF (10 mL) was added piperidine (510 mg, 6 mmol, 8 eq) in one portion at 20° C. The mixture was stirred at 20° C. for 3 h. TLC (DCM:MeOH=5:1) showed the reaction was completed. The reaction mixture was concentrated and the residue was purified by prep-TLC ($SiO_2$, DCM:MeOH=5:1) to give the crude title compound (320 mg) as a white solid. LCMS: 366.2 ($MH^+$)

EXAMPLE 1

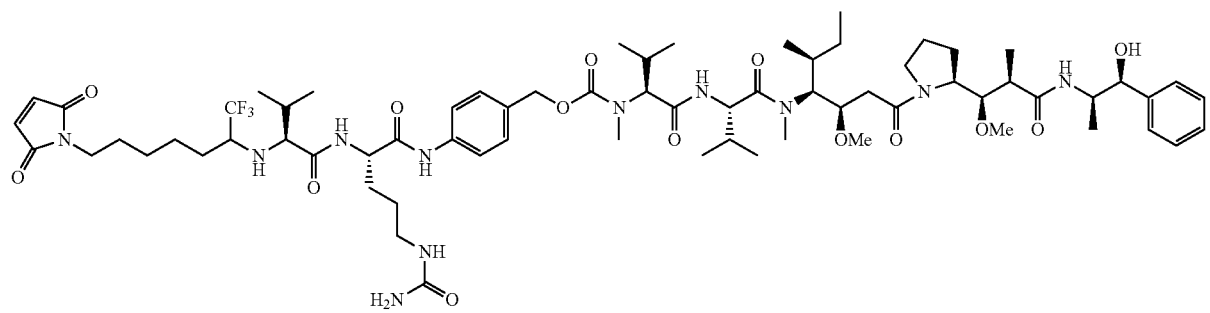

MTM H-Val-Cit-PABO(CO)-MMAE

Step 1: MTMH-Val-Cit-PAB-OH

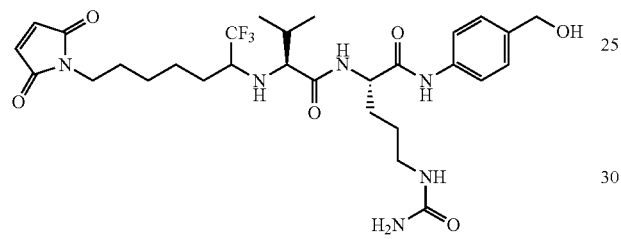

To a solution of crude (2S)-2,5-dioxopyrrolidin-1-yl-2-{[7-(2,5-dioxo-2,5-dihydro-1H-pyrrol-1-yl)-1,1,1-trifluoro-heptan-2-yl]amino}-3-methylbutanoate (INTERMEDIATE 1) (0.56 mmol) in DMF (5 mL) was added Cit-PAB-OH (INTERMEDIATE 4) (0.56 mmol) under $N_2$. The resulting mixture was stirred at room temperature for 16 h. Solvent was removed in vacuo. The thick oily residue was washed with tert-butyl methyl ether (10 mL×2) to give the crude title compound, which was used for next step without further purification. LCMS(ESI): 627.3 ($MH^+$)

Step 2: MTMH-Val-Cit-PAB (4-nitrophenyl) carbonate

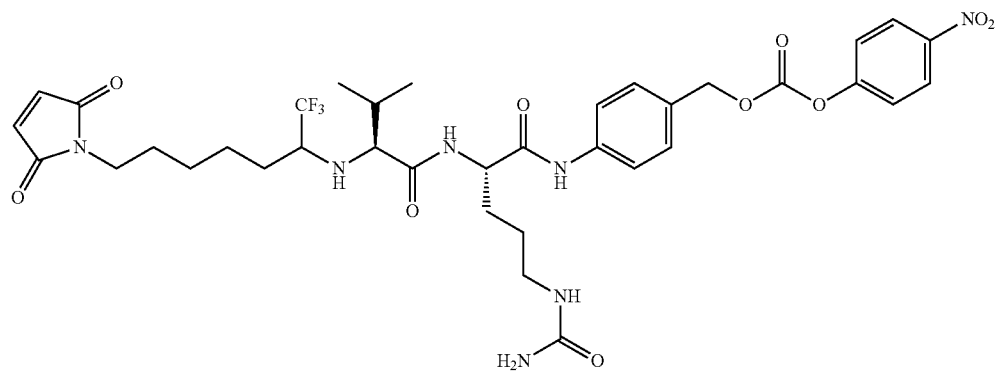 [SMILES: CC(C)[C@H](NC(CCCCCN1C(=O)C=CC1=O)C(F)(F)F)C(=O)N[C@@H](CCCNC(N)=O)C(=O)Nc1ccc(COC(=O)Oc2ccc([N+](=O)[O-])cc2)cc1]

To a solution of MTMH-Val-Cit-PAB-OH (260 mg crude, 0.56 mmol) in DMF (3 mL) was added bis(4-nitrophenyl) carbonate (340 mg 1.12 mmol) and DIPEA (108 mg, 0.84 mmol). The mixture was stirred at room temperature for about 1 h and concentrated. The residue was washed with tert-butyl methyl ether (10 mL×2) to give the title compound, which was used directly for next step without further purification. LCMS(ESI): 792.3 ($MH^+$)

Step 3: MTMH-Val-Cit-PABO(CO)-MMAE

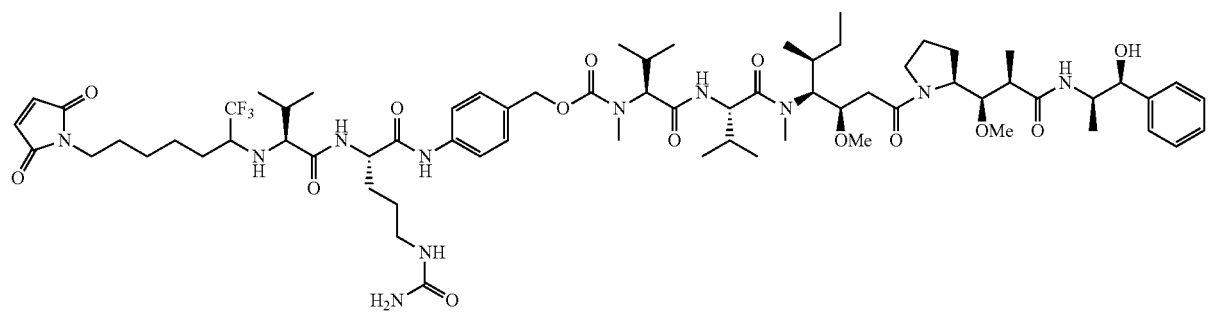 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(CCCCCN2C(=O)C=CC2=O)C(F)(F)F)C(C)C)cc1)C(C)C]

To a solution of MMAE (0.28 mmol) and MTMH-Val-Cit-PAB (4-nitrophenyl) carbonate (0.56 mmol) in anhydrous DMF (2.5 mL) was added HOBt (23 mg, 0.17 mmol). After stirring at room temperature for 2 min, pyridine (0.5 mL) was added. The mixture was stirred at room temperature for 16 h and then concentrated. The residue was purified by Prep-HPLC to give the title compound (40 mg, 10.4%) as a white solid, LCMS(ESI):=685.9 [(M/2)H$^+$]

EXAMPLE 2

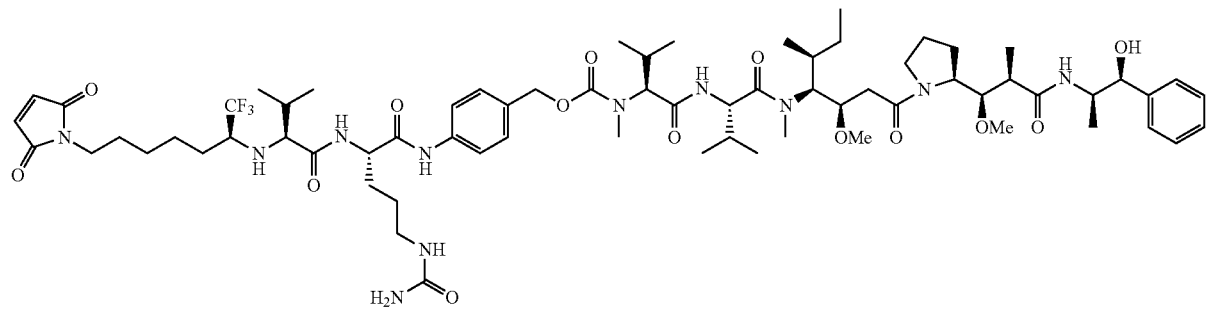 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](N[C@@H](CCCCCN2C(=O)C=CC2=O)C(F)(F)F)C(C)C)cc1)C(C)C]

(S)-MTMH-Val-Cit-PABO(CO)-MMAE

Step 1: (S)-MTMH-Val-Cit-PAB-OH

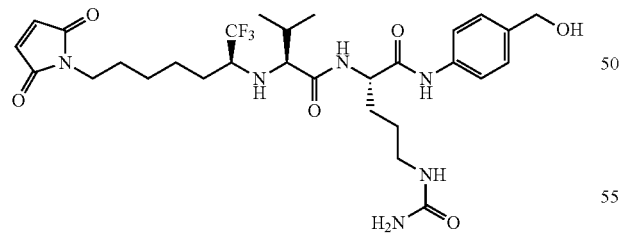

To a mixture of (S)-MTMH-Val (INTERMEDIATE 3) (300 mg, 823 umol, 1 eq), HOBt (133.5 mg, 988 umol, 1.20 eq), EDCl (189 mg, 988 umol, 1.20 eq), DIPEA (426 mg, 3.3 mmol, 4 eq) and Cit-PAB-OH (INTERMEDIATE 4) (277 mg, 988 umol, 1.20 eq) in DMF (10 mL) was stirred at 30° C. for 6 h. TLC showed the reaction was completed. The mixture was concentrated in vacuum. The residue was purified by prep-TLC (EtOAc:MeOH=10:1) to afford the title compound (410 mg, 52.3% yield) as a white solid. MS: 627 (MH+)

Step 2: (S)-MTMH-Val-Cit-PAB (4-nitrophenyl) carbonate

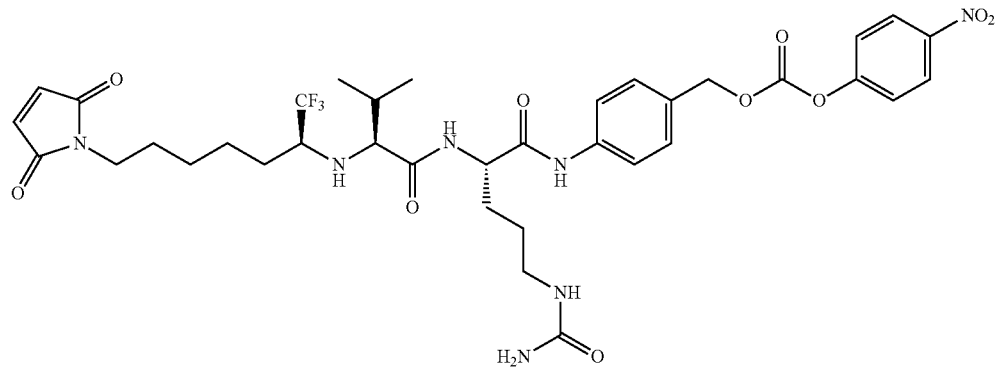 [SMILES: CC(C)[C@H](N[C@@H](CCCCCN1C(=O)C=CC1=O)C(F)(F)F)C(=O)N[C@@H](CCCNC(N)=O)C(=O)Nc1ccc(COC(=O)Oc2ccc([N+](=O)[O-])cc2)cc1]

To a mixture of (S)-MTMH-Val-Cit-PAB-OH (250 mg, 399 umol, 1 eq) in DMF (10 mL) was added DIPEA (77 mg, 598 umol, 1.5 eq) and bis(4-nitrophenyl) carbonate (243 mg, 798 umol, 2.0 eq) in one portion at 25° C. under $N_2$. The mixture was stirred at 25° C. for 15 h. LCMS showed the reaction was completed. The mixture was concentrated in vacuum. The residue was purified by prep-TLC (EtOAc) to afford the title compound (185 mg, 58.6% yield) as a white solid. MS: 792 (MH+)

Step 3: (S)-MTMH-Val-Cit-PABO(CO)-MMAE

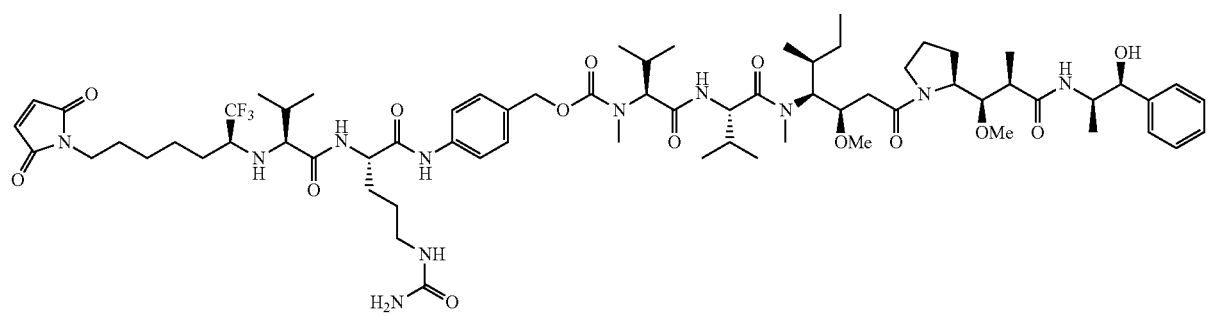 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](N[C@@H](CCCCCN2C(=O)C=CC2=O)C(F)(F)F)C(C)C)cc1)C(C)C]

To a mixture of MMAE (200 mg, 279 umol, 1 eq) and LS)-MTMH-Val-Cit-PAB (4-nitrophenyl) carbonate (250 mg, 316 umol, 1.13 eq) in DMF (10 mL) was added HOBt (25 mg, 185 umol, 0.66 eq) and pyridine (980 mg, 12.4 mmol, 44.5 eq.) in one portion at 25° C. under $N_2$. And then the reaction mixture was allowed to stir at 25° C. for 15 h. LCMS showed the reaction was completed. The mixture was diluted with EtOAc (200 mL) and washed with water (150 mL×3). The organic layer was concentrated to give the residue which was purified by prep-HPLC (FA) to give the title compound (109 mg, 30% yield) as a white solid. LCMS (ESI): 686 [(M/2)H$^+$]

EXAMPLE 3

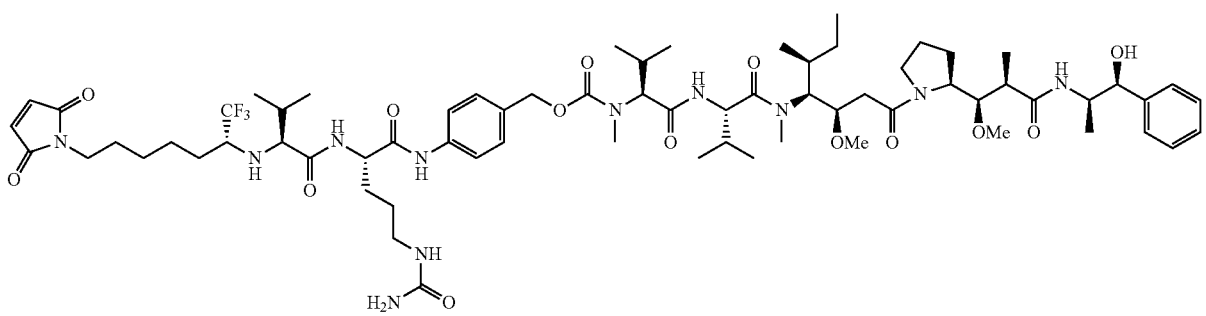 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](N[C@H](CCCCCN2C(=O)C=CC2=O)C(F)(F)F)C(C)C)cc1)C(C)C]

(R)-MTMH-Val-Cit-PABO(CO)-MMAE

The title compound was prepared in a similar manner as described for (S)-MTMH-Val-Cit-PABO(CO)-MMAE (EXAMPLE 2), step 1 to 3, from (R)-MTMH-Val (INTERMEDIATE 2) and Cit-PAB-OH (INTERMEDIATE 4). LCMS (ESI): 686.1 [(M/2)H$^+$]

EXAMPLE 4

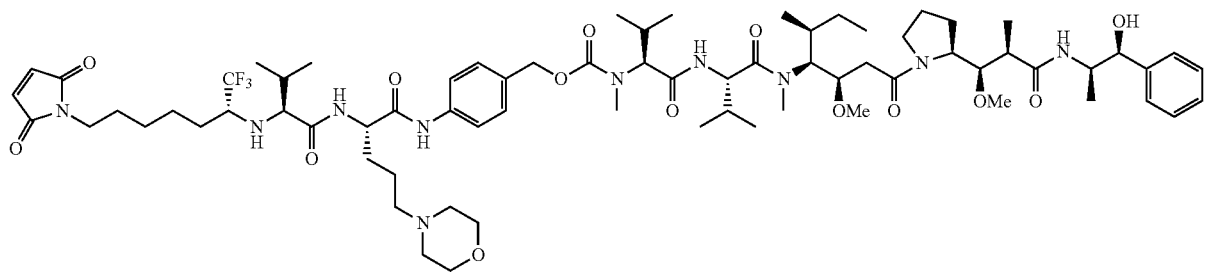 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCN2CCOCC2)NC(=O)[C@@H](N[C@H](CCCCCN2C(=O)C=CC2=O)C(F)(F)F)C(C)C)cc1)C(C)C]

(R)-MTMH-DP1-PABO(CO)-MMAE

Step 1: (R)-MTMH-DP1-PAB-OH

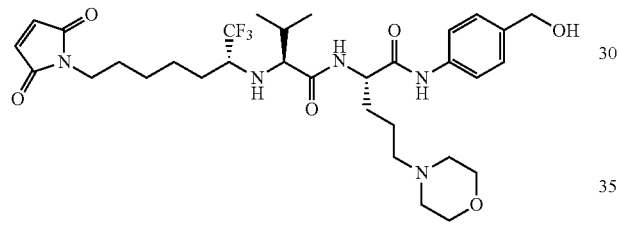

To a solution of (S)-MTMH-Val (INTERMEDIATE 2) (350 mg, 0.96 mmol) in DMF (15 mL) was added HOBt (155.75 mg, 1.15 mmol), EDO (220.97 mg, 1.15 mmol), DIPEA (496.59 mg, 3.84 mmol) and (S)-2-amino-N-(4-(hydroxymethyl)phenyl)-5-morpholinopentanamide (INTERMEDIATE 5) (390 mg, 1.1 mmol) under N$_2$ and was then stirred at 25° C. for 6 h. The reaction mixture was evaporated to dryness and the residue was purified by column chromatography (EtOAc:MeOH=10:1) to afford the title compound (400 mg, yield 63.70%). MS: 654 (MO Step 2: (R)-MTMH-DP1-PAB (4-nitrophenyl) carbonate

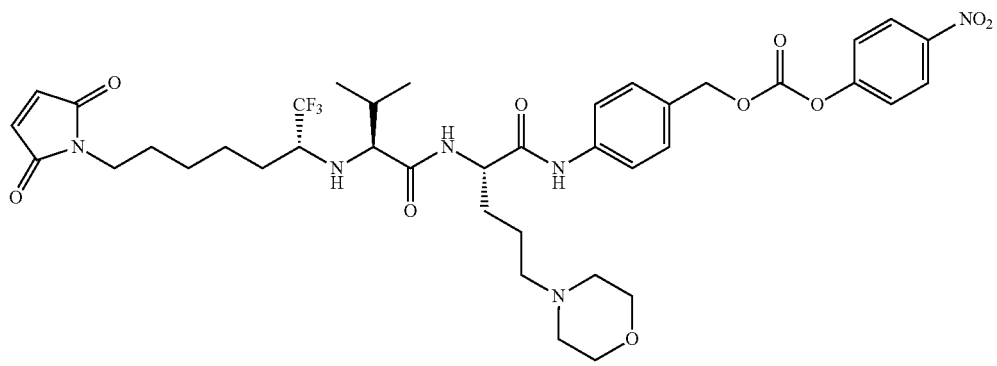 [SMILES: CC(C)[C@H](N[C@H](CCCCCN1C(=O)C=CC1=O)C(F)(F)F)C(=O)N[C@@H](CCCN1CCOCC1)C(=O)Nc1ccc(COC(=O)Oc2ccc([N+](=O)[O-])cc2)cc1]

To a solution of (R)-MTMH-DP1-PAB-OH in DMF (10 mL) was added DIEA (77.10 mg, 0.597 mmol) and bis(4-nitrophenyl) carbonate (349 mg, 1.15 mmol) under N$_2$. The mixture was stirred at 25° C. for 16 h and evaporated to dryness. The residue was purified by prep-TLC (EtOAc) to afford the title compound (300 mg, yield 79.84%). MS: 819 (MO Step 3: (R)-MTMH-DP1-PABO(CO)-MMAE

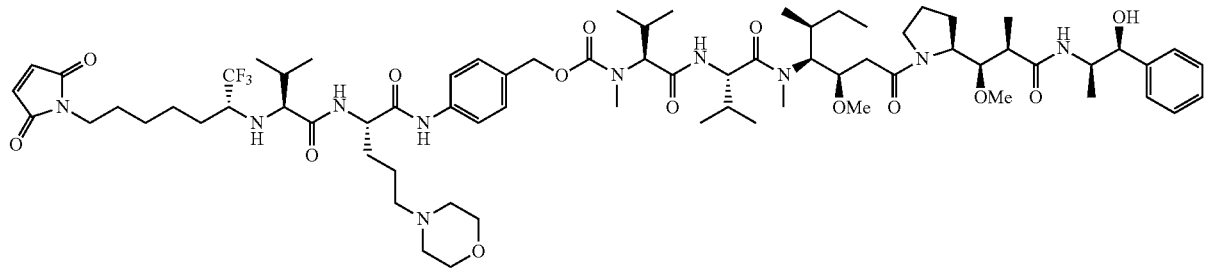 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCN2CCOCC2)NC(=O)[C@@H](N[C@H](CCCCCN2C(=O)C=CC2=O)C(F)(F)F)C(C)C)cc1)C(C)C]

To a solution of (R)-MTMH-DP1-PAB (4-nitrophenyl) carbonate (200 mg, 0.244 mmol) in DMF (4 mL) was added MMAE (200 mg, 0.278 mmol), HOBt (10 mg, 0.074 mmol) and pyridine (0.8 mL) under N$_2$. The mixture was stirred at 25° C. for 16 h, diluted with EtOAc (50 mL), washed with water (20 mL×2), brine (20 mL) and concentrated. The residue was purified by prep-HPLC (FA) to afford the title compound (160 mg, yield 46.87%). LCMS (ESI): 699.5 [(M/2)H$^+$]

EXAMPLE 5

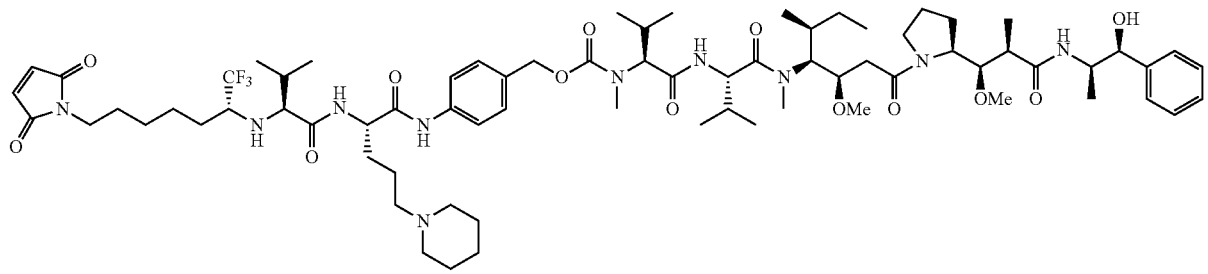 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCN2CCCCC2)NC(=O)[C@@H](N[C@H](CCCCCN2C(=O)C=CC2=O)C(F)(F)F)C(C)C)cc1)C(C)C]

(R)-MTMH-DP2-PABO(CO)-MMAE

The title compound was prepared in a similar manner as (R)-MTMH-DP1-PAB(CO)-MMAE (EXAMPLE 4) but with piperidine to replace morpholine of INTERMEDIATE 5 for the required corresponding intermediate. LCMS (ESI): 698.6 [(M/2)H$^+$]

EXAMPLE 6

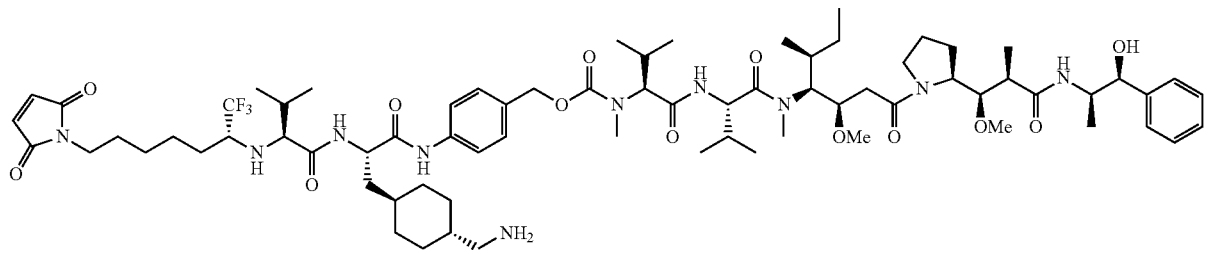 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C[C@H]2CC[C@H](CN)CC2)NC(=O)[C@@H](N[C@H](CCCCCN2C(=O)C=CC2=O)C(F)(F)F)C(C)C)cc1)C(C)C]

(R)-MTMH-DP3-PABO(CO)-MMAE

Step 1: (R)-MTMH-Boc-DP3-PAB-OH

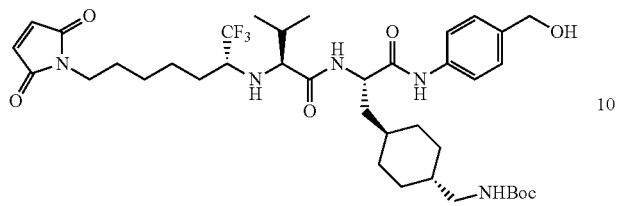

To a mixture of (S)-MTMH-Val (INTERMEDIATE 2) (225.0 mg, 617.5 umol) in DMF (12 mL) was added HOBt (108.5 mg, 802.8 umol), EDO (153.9 mg, 802.8 umol) and DIEA (239.4 mg, 1.9 mmol) at 25° C. under $N_2$. After 5 min, tert-butyl ((trans-4-(2-amino-3-((4-(hydroxymethyl)phenyl)amino)-3-oxopropyl)cyclohexyl)methyl)carbamate (INTERMEDIATE 6) (300.5 mg, 741.0 umol) was added and the mixture was further stirred at 25° C. for 4 h. TLC showed that most of starting material was consumed. The mixture was diluted with EtOAc (20 mL), washed with sat.$NH_4Cl$ solution (30 mL×3) and concentrated. The residue was purified by prep-TLC and then SFC to give the title compound (peak 1: 140 mg, 30% yield) as a white solid.

Step 2: (R)-MTMH-Boc-DP3-PABO(CO)-MMAE

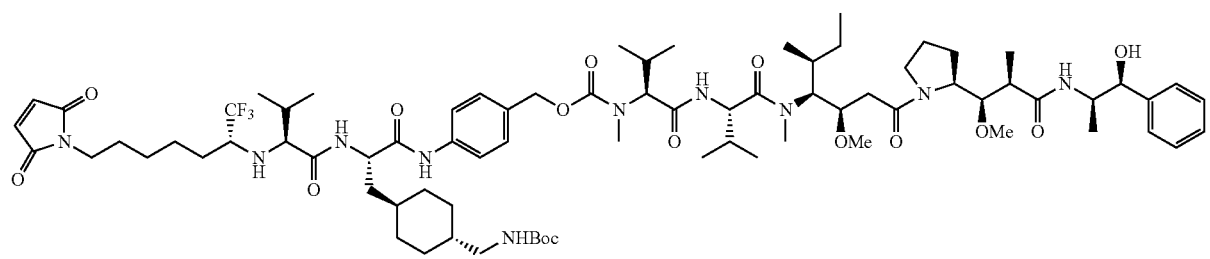 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C[C@H]2CC[C@H](CNC(=O)OC(C)(C)C)CC2)NC(=O)[C@@H](N[C@H](CCCCCN2C(=O)C=CC2=O)C(F)(F)F)C(C)C)cc1)C(C)C]

The title compound was prepared in a similar manner as described for (S)-MTMH-Val-Cit-PABO(CO)-MMAE (EXAMPLE 2), step 2 to 3, from (R)-MTMH-Boc-DP3-PAB-OH. LCMS [((M−100)/2)H$^+$]: 698.5

Step 3: (R)-MTMH-DP3-PAB-MMAE

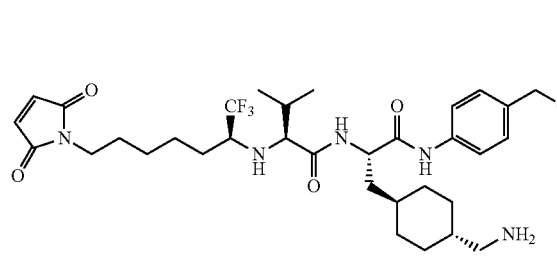

To a mixture of (R)-MTMH-Boc-DP3-PABO(CO)-MMAE (200.00 mg, 133.70 umol) in $CH_3CN$ (4.25 mL) and $H_2O$ (0.25 mL) was added TFA (0.5 mL) in one portion at 25° C. The mixture was stirred at 25-29° C. for 16 h. LCMS showed the reaction was complete. The mixture was concentrated under reduced pressure at 40° C. The residue was purified by pre-HPLC (FA), without further concentration and lyophilized directly to afford the title compound (105.00 mg, 56.3% yield) as a white solid. LCMS: 698.7 [(M/2)H$^+$]

EXAMPLE 7

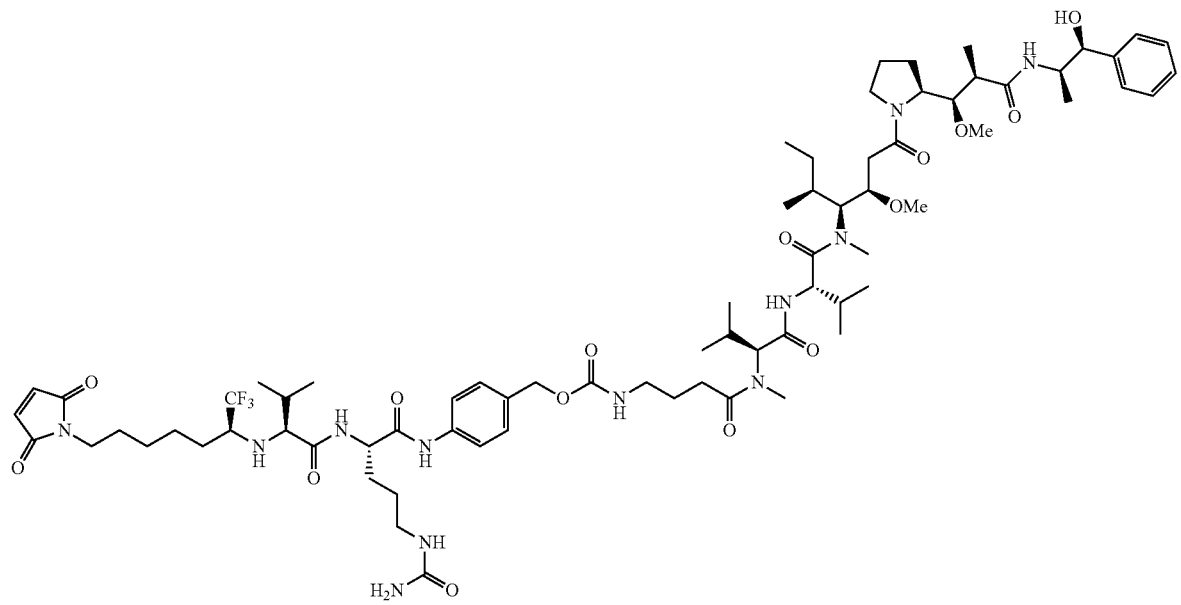 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)CCCNC(=O)OCc1ccc(NC(=O)[C@H](CCCNC(N)=O)NC(=O)[C@@H](N[C@@H](CCCCCN2C(=O)C=CC2=O)C(F)(F)F)C(C)C)cc1)C(C)C]

(S)-MTMH-Val-Cit-PABO(CO)-ABA-MMAE

Step 1: (S)-MTMH-Val-Cit-PABO(CO)-ABA

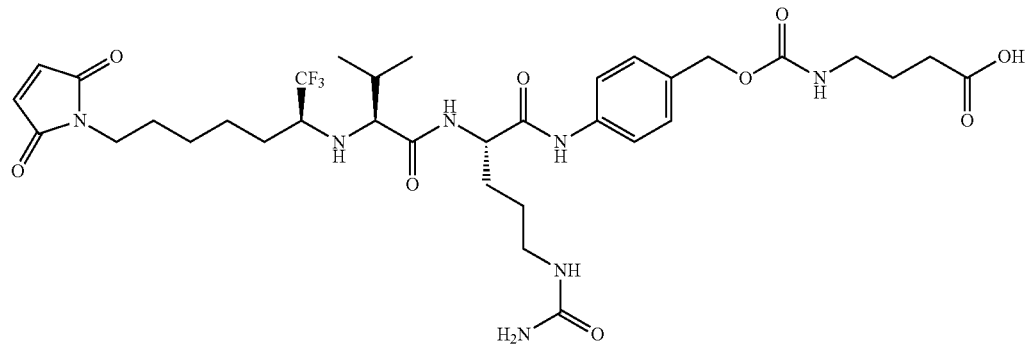 [SMILES: CC(C)[C@H](N[C@@H](CCCCCN1C(=O)C=CC1=O)C(F)(F)F)C(=O)N[C@@H](CCCNC(N)=O)C(=O)Nc1ccc(COC(=O)NCCCC(=O)O)cc1]

To a mixture of (S)-MTMH-Val-Cit-PAB (4-nitrophenyl) carbonate (420 mg, 531 umol, 1 eq) and 4-aminobutanoic acid (109 mg, 1.1 mmol, 2 eq) in DMF (8 mL) was added DIPEA (205 mg, 1.6 mmol, 3 eq) in one portion at 20° C. under $N_2$. And then the reaction mixture was allowed to stir at 20° C. for 12 h. TLC (Dichloromethane:Methanol=10:1) showed the reaction was complete. The mixture was diluted with EtOAc (50 mL), washed with water (50 ml) and concentrated under vacuum. The residue was purified by pre-TLC (DCM/MeOH=10:1) to give the title compound (236 mg, 46.47% yield, ~79% purity) as a white solid. MS: 756.3 (MH$^+$)

Step 2:
(S)-MTMH-Val-Cit-PABO(CO)-ABA-MMAE

To a mixture of (S)-MTMH-Val-Cit-PABO(CO)-ABA (50 mg, 66 umol, 1 eq) and DIEA (26 mg, 198 umol, 3 eq) in DMF (3 mL) was added HATU (30 mg, 79 umol, 1.2 eq) in one portion at 10° C. under $N_2$. The mixture was stirred at 10° C. for 30 min, then MMAE (47.5 mg, 66 umol, 1 eq) was added and the mixture was further stirred at 28° C. for 12 h. LCMS showed the reaction was completed. The mixture was concentrated and the residue was purified by pre-HPLC (Column, Phenomenex Synergi C18 150*25*10 um; Condition, 0.225% FA-CAN; Begin B, 45; End B, 75; Gradient Time(min), 10; 100% B Hold Time(min), 2; Flow Rate (ml/min), 25) to give the title compound (25 mg, 26% yield) as a white solid. LCMS: 728.7[(M/2)H$^+$]

EXAMPLE 8

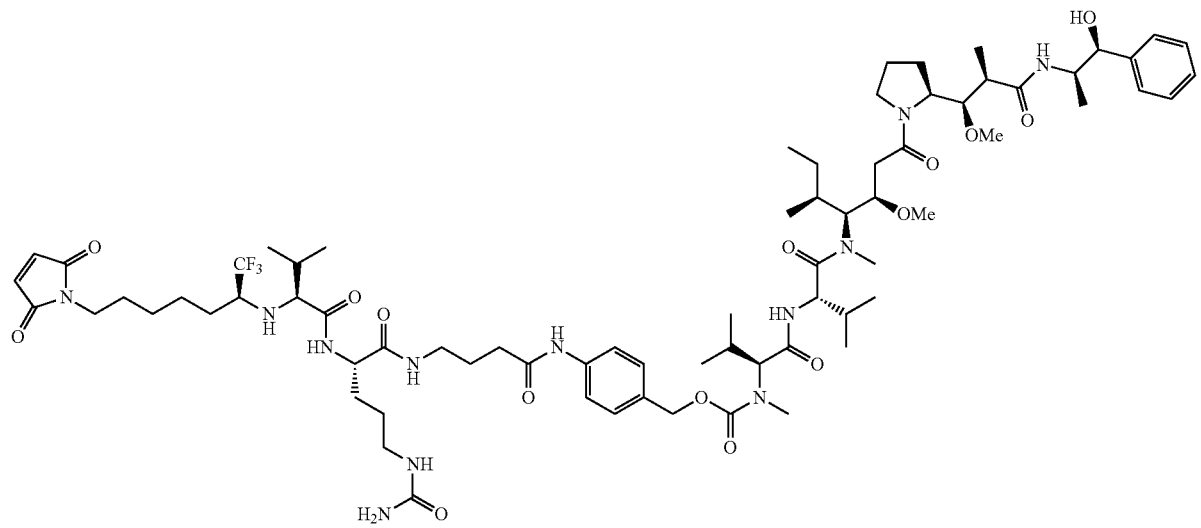 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)CCCNC(=O)[C@H](CCCNC(N)=O)NC(=O)[C@@H](N[C@@H](CCCCCN2C(=O)C=CC2=O)C(F)(F)F)C(C)C)cc1)C(C)C]

(S)-MTMH-Val-Cit-ABA-PABO(CO)-MMAE

Step 1: (S)-MTMH-Val-Cit-ABA-PAB-OH

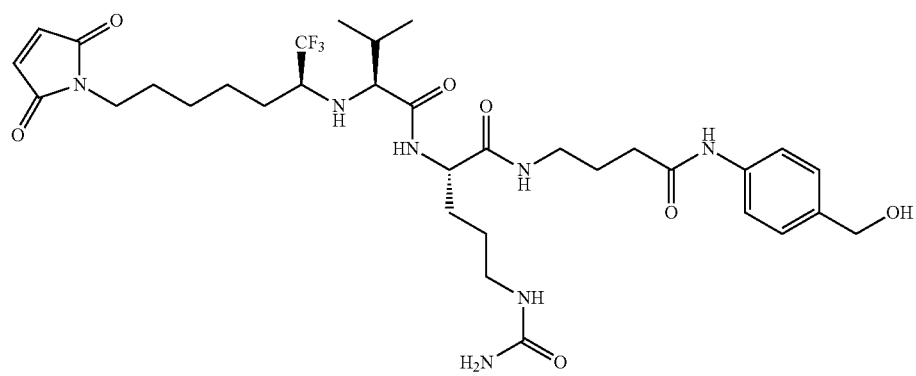 [SMILES: CC(C)[C@H](N[C@@H](CCCCCN1C(=O)C=CC1=O)C(F)(F)F)C(=O)N[C@@H](CCCNC(N)=O)C(=O)NCCCC(=O)Nc1ccc(CO)cc1]

To a solution of (S)-MTMH-Val (INTERMEDIATE 3) (383 mg, 1.05 mmol, 1.2 eq) in DMF (8 mL) was added DIPEA (453 mg, 3.50 mmol, 4 eq), HOBt (142 mg, 1.05 mmol, 1.2 eq) and EDCl (202 mg, 1.05 mmol, 1.2 eq) in one portion at 20° C. and stirred for 10 min under $N_2$ Cit-ABA-PAB-OH (INTERMEDIATE 7) (320 mg, 876 umol, 1 eq) was added in one portion at 20° C. and the mixture was further stirred at 20° C. for 16 h under $N_2$. TLC (DCM:MeOH=5:1) showed the reaction was completed. The reaction mixture was concentrated and the residue was purified by prep-TLC (SiO$_2$, DCM:MeOH=5:1) to give the crude title compound (370 mg). LCMS: 712.2 (MH$^+$)

Step 2: (S)-MTMH-Val-Cit-ABA-PAB (4-nitrophenyl) carbonate

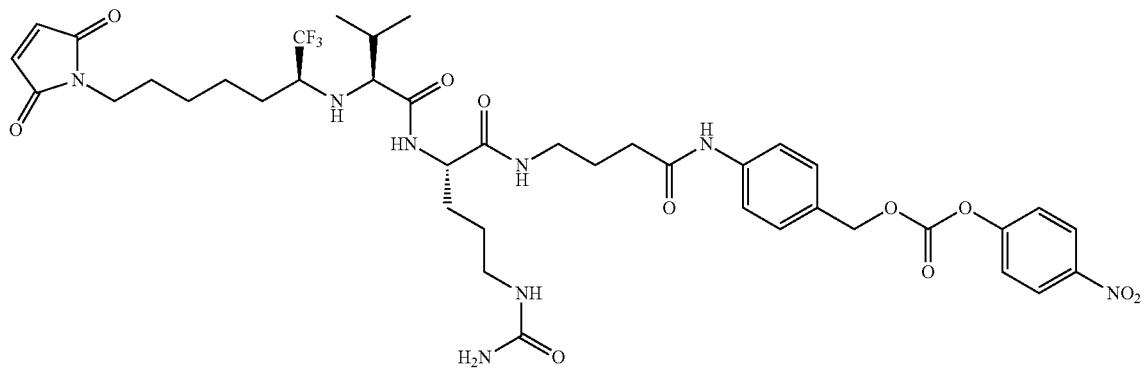 [SMILES: CC(C)[C@H](N[C@@H](CCCCCN1C(=O)C=CC1=O)C(F)(F)F)C(=O)N[C@@H](CCCNC(N)=O)C(=O)NCCCC(=O)Nc1ccc(COC(=O)Oc2ccc([N+](=O)[O-])cc2)cc1]

To a solution of (S)-MTMH-Val-Cit-ABA-PAB-OH (370 mg, 520 umol, 1 eq) in DMF (10 mL) was added DIPEA (80.6 mg, 624 umol, 1.2 eq) at 20° C. was added bis(4-nitrophenyl) carbonate (206 mg, 676 umol, 1.3 eq) in one portion at 20° C. under $N_2$. The mixture was stirred at 20° C. for 16 h. TLC (DCM:MeOH=10:1) showed starting material was consumed completely. The mixture was concentrated and the residue was purified by pre-TLC (SiO$_2$, DCM:MeOH=10:1) to give the title compound (70 mg, 79.83 umol, 15.36% yield) as a yellow oil. LCMS: 877.3 (MH$^+$)

Step 3: (S)-MTMH-Val-Cit-ABA-PABO(CO)-MMAE

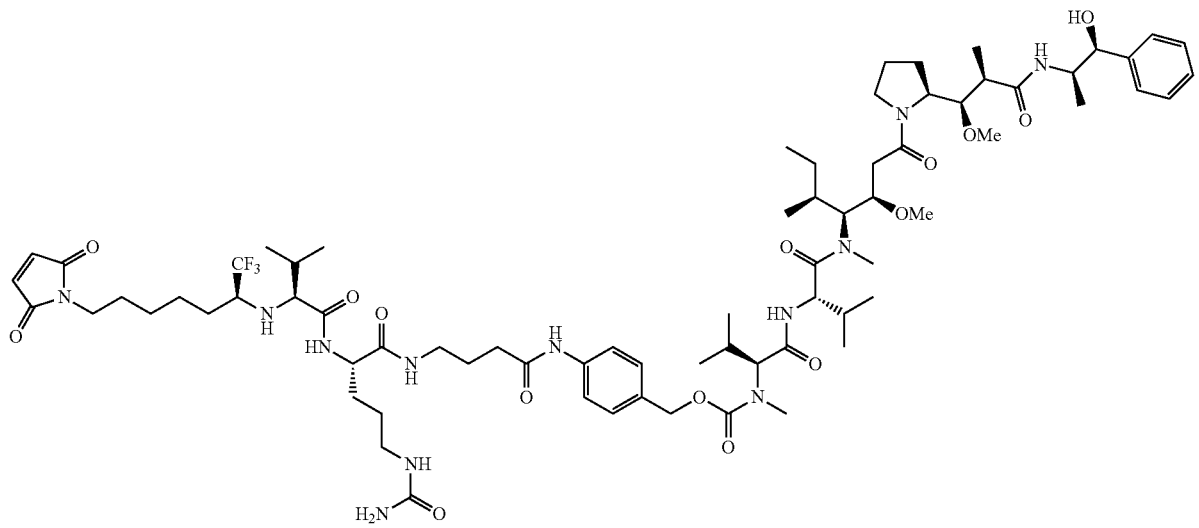 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)CCCNC(=O)[C@H](CCCNC(N)=O)NC(=O)[C@@H](N[C@@H](CCCCCN2C(=O)C=CC2=O)C(F)(F)F)C(C)C)cc1)C(C)C]

To a solution of (S)-MTMH-Val-Cit-ABA-PAB (4-nitrophenyl) carbonate (70 mg, 80 umol, 1 eq) and MMAE (57.3 mg, 79.8 umol, 1 eq) in DMF (6 mL) was added HOBt (5.4 mg, 39.9 umol, 0.5 eq) and pyridine (63.1 mg, 798 umol, 10 eq) at 20° C. The mixture was stirred at 20° C. for 16 h. TLC (DCM:MeOH=10:1) showed the reaction was completed. The mixture was concentrated in vacuum and the residue was purified by Pre-HPLC (FA condition; Column: Phenomenex Synergi Max-RP 250*80 10u; Condition: 0.225% FA-ACN; Begin B: 40; End B: 70) to afford the title compound (40.8 mg, 48.6% yield) as a white solid. LCMS: 728.5 [(M/2)H$^+$].

EXAMPLE 9
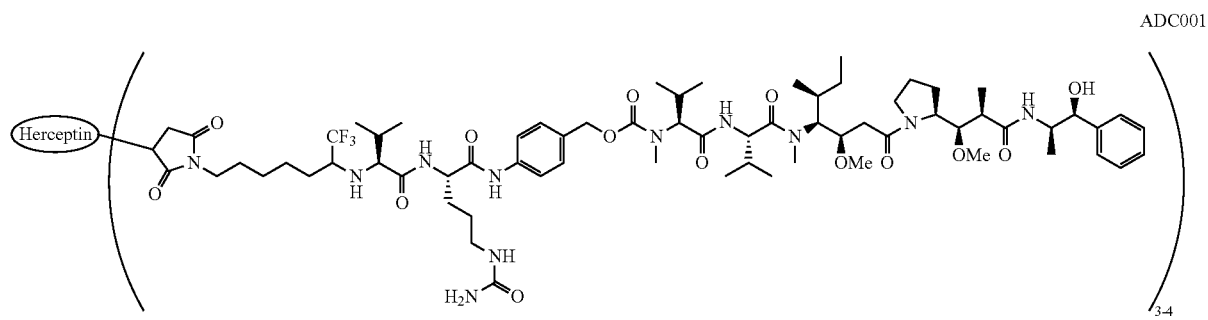
ADC001
Herceptin (240 mg) and drug-linker intermediate MTMH-Val-Cit-PAB-OH (11.3 mg), EXAMPLE 1 was coupled according to the general procedure for conjugation of drug-linker intermediate to herceptin to give the title ADC (168 mg, 70%).
Other ADC Examples With Herceptin Were Prepared In A Similar Manner As Example 9
EXAMPLE 10
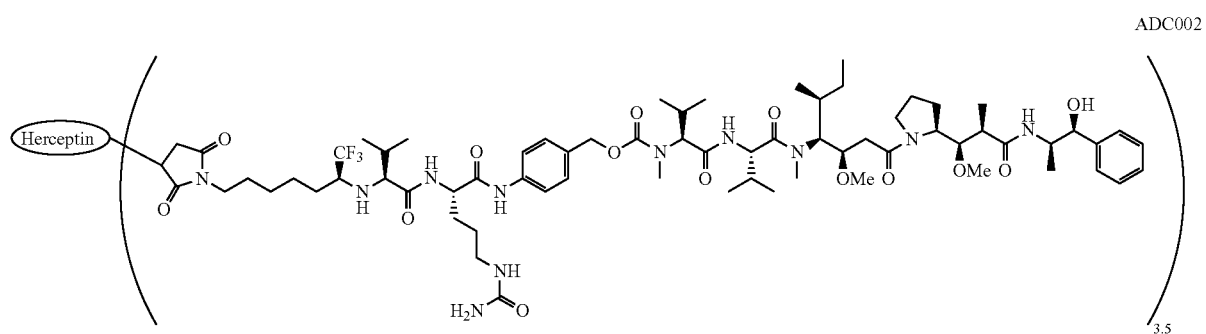
ADC002
EXAMPLE 11
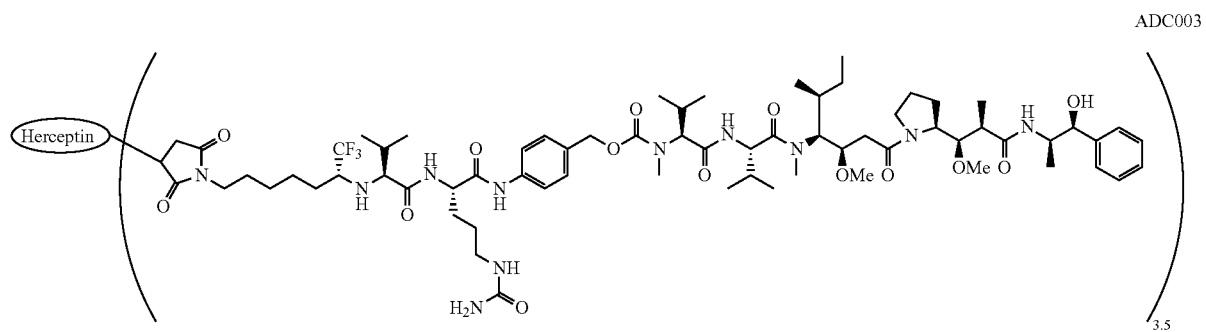
ADC003

EXAMPLE 12
ADC004
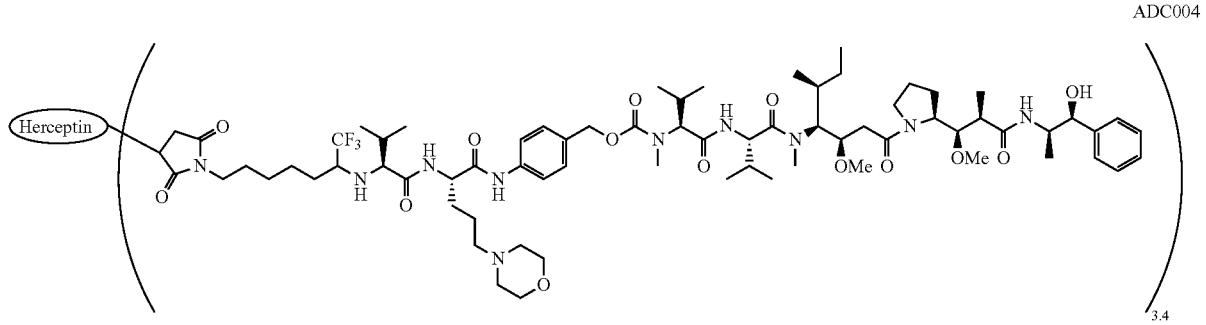
EXAMPLE 13
ADC005
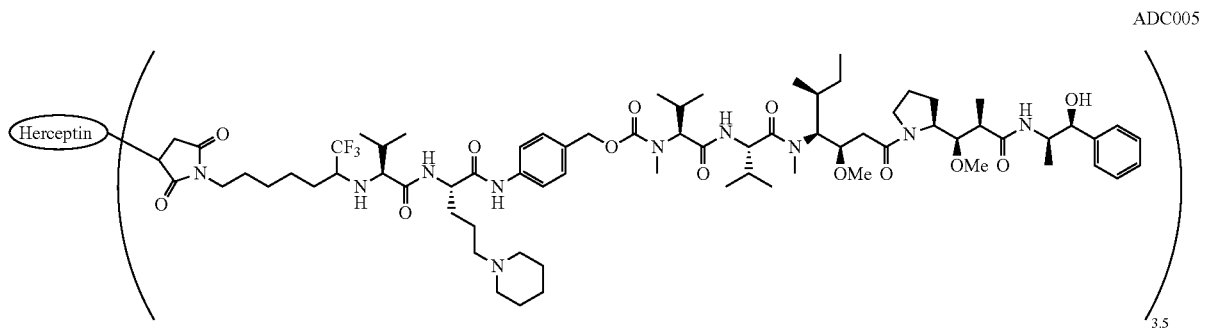
EXAMPLE 14
ADC006
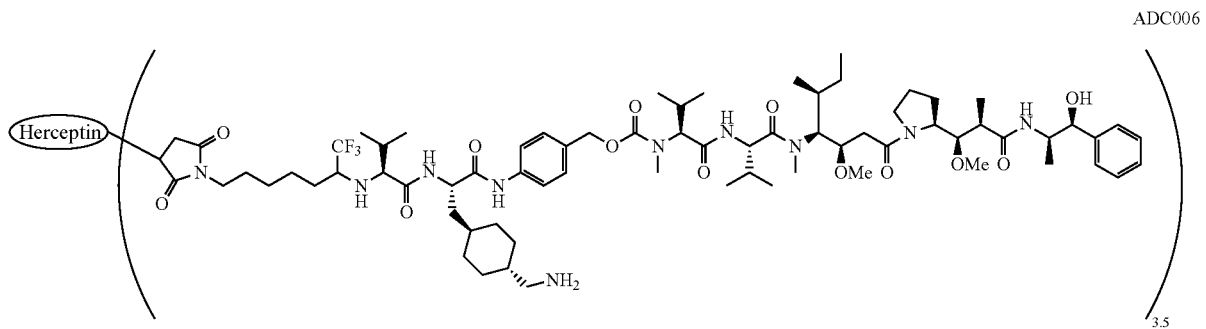
ADC Examples With Erbitux Were Also Prepared In A Similar Manner As Example 9
Example 15
ADC007
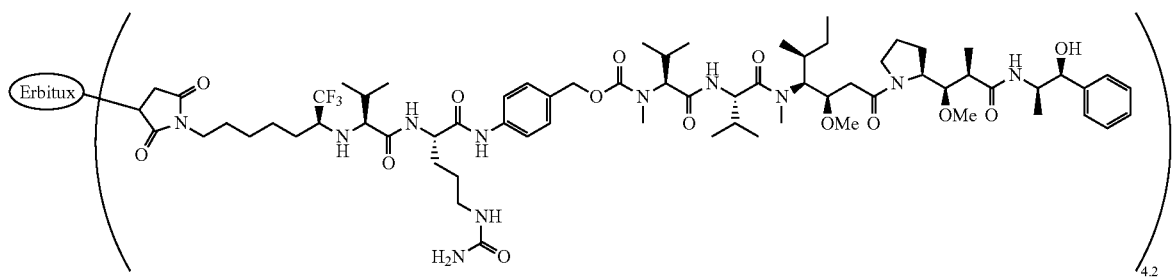

Example 16

-continued

ADC008

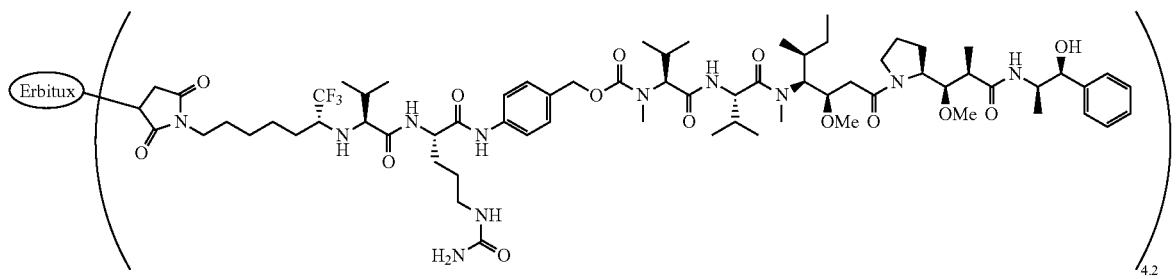

Screening of Suitable Dipeptide Units for Drug-Linker Intermediates

A convenient method was developed to identify suitable dipeptide units for the use in drug-linker intermediates. Cbz-protected dipeptides incorporated a fluorescent tag (7-amino-4-methylcouramin, 7-AMC) via a para-aminobenzyl carbonyl fragment were prepared by standard peptide chemistry as shown in Scheme 1. These dipeptide substrates were then incubated with bovine cathepsin B under a similar condition as described by Dubowchik (Biorg. Med. Chem. Lett. 1998, 8, 3341-3346). Rate of hydrolysis by bovine cathepsin B was measured by the release of 7-AMC (Table 1). Novel dipeptides with hydrolysis rates slower than the substrate A were rejected. The three dipeptide units in FS-9, FS-10 and FS-11 were selected as additional dipeptide units for drug-linker intermediate preparation.

Scheme 1. Synthesis of cbz-protected dipeptide fluorescent substrates

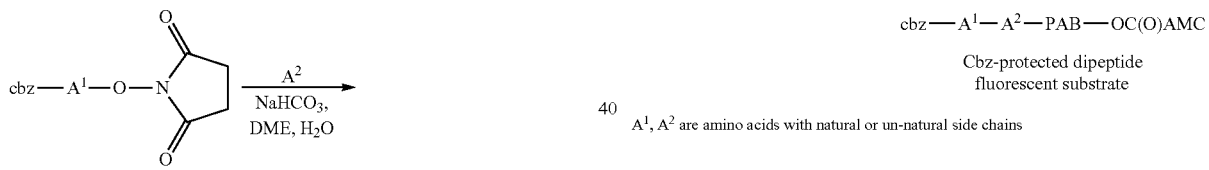

$A^1$, $A^2$ are amino acids with natural or un-natural side chains

TABLE 1

Rate of hydrolysis under the incubation with bovine cathepsin B

| Fluorescent Substrate | Rate of Hydrolysis (nmmol/min/mg) |
|---|---|
| A | 2.67 |

TABLE 1-continued
Rate of hydrolysis under the incubation with bovine cathepsin B
| Fluorescent Substrate | Rate of Hydrolysis (nmmol/min/mg) |
|---|---|
| 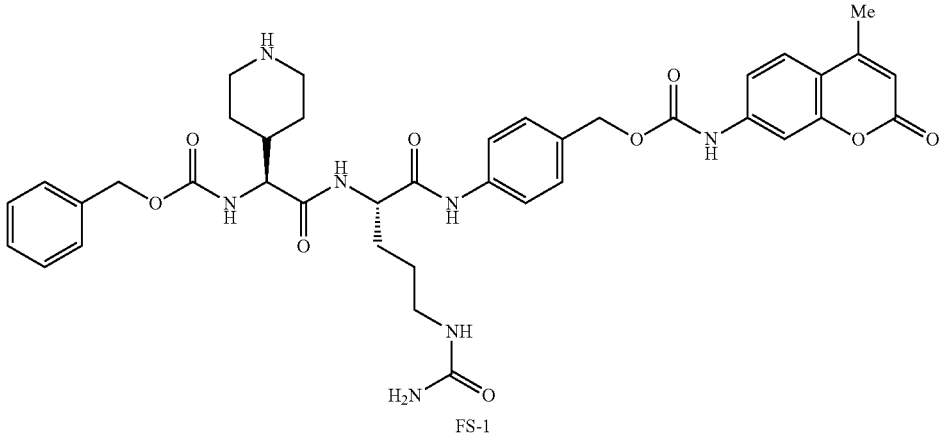 FS-1 | 0.84 |
| 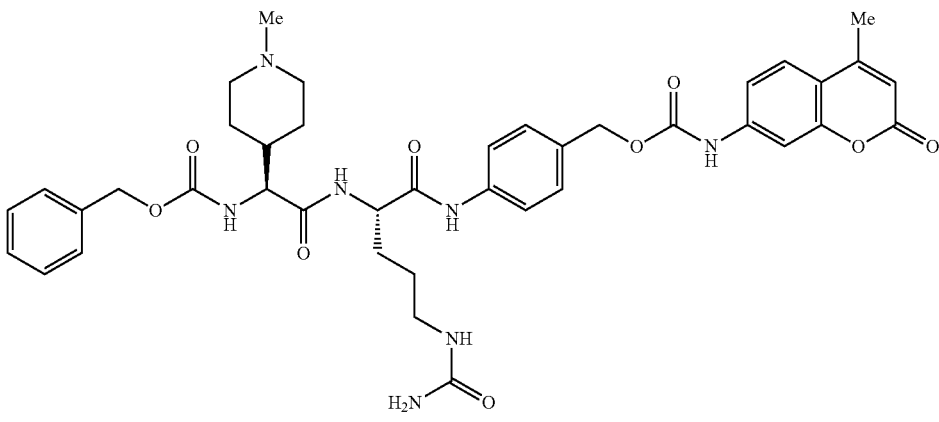 FS-2 | 0.59 |
| 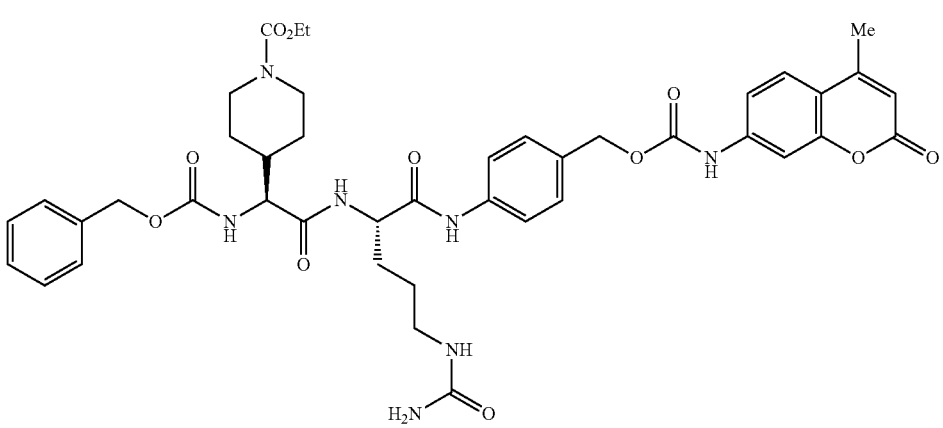 FS-3 | 0.63 |

TABLE 1-continued

Rate of hydrolysis under the incubation with bovine cathepsin B

| Fluorescent Substrate | Rate of Hydrolysis (nmmol/min/mg) |
|---|---|
| FS-4 | 0.84 |
| FS-5 | 0 |
| FS-6 | 0.55 |

TABLE 1-continued

Rate of hydrolysis under the incubation with bovine cathepsin B

| Fluorescent Substrate | Rate of Hydrolysis (nmmol/min/mg) |
|---|---|
| FS-7 | 0 |
| FS-8 | 0 |
| FS-9 | 27.2 |

TABLE 1-continued

Rate of hydrolysis under the incubation with bovine cathepsin B

| Fluorescent Substrate | Rate of Hydrolysis (nmmol/min/mg) |
|---|---|
| 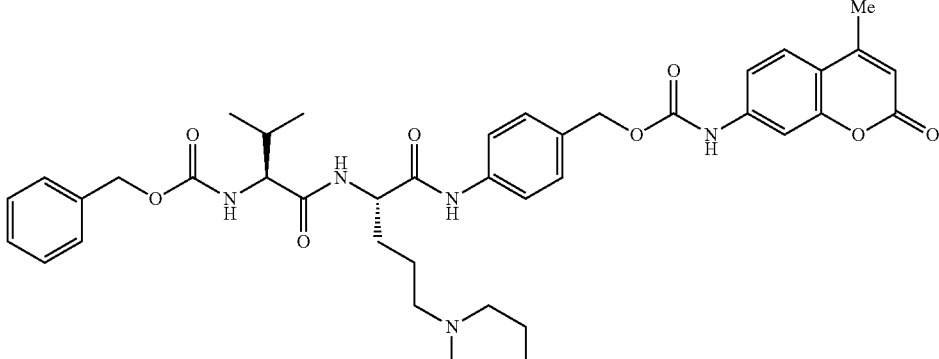 FS-10 | 25.1 |
| 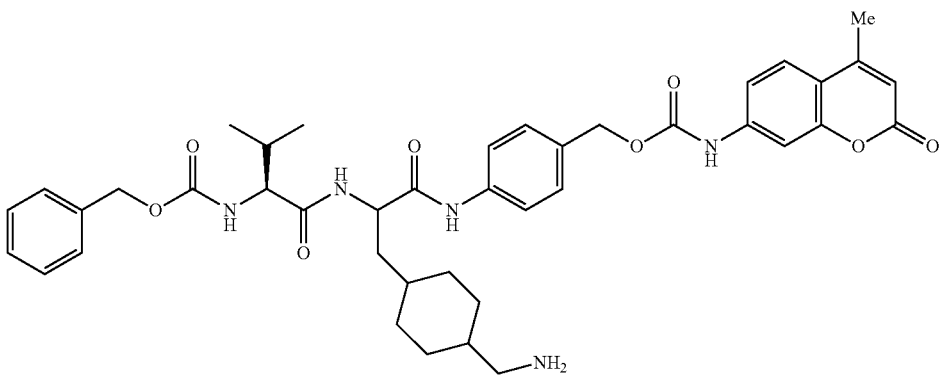 FS-11 | 20.9 |

In Vitro Cytotoxicity Study
(a) Breast Cancer Cell Line HCC1954

Breast cancer cell line HCC1954 was grown in RPMI1640 medium supplemented with 10% fetal bovine serum and maintained in an atmosphere of 5% $CO_2$ in a humidified 37° C. incubator.

The day before treatment, cells were collected and seeded into 96-well plates (2,000 cells per well). On the second day, cells were treated with a dilute concentration of Herceptin and ADCs of this invention (1, 0.3333, 0.1111, 0.037, 0.0123, 0.0041, 0.0014, 0.00046 and 0.00015 µg/ml). Each treatment was performed in triplicate.

After 72 hours treatment, cell viability was assessed by Cell Titer-Glo kit (Promega) according to the manufacturer's instruction.

The study was compared to a control ADC (ADC-HA) with the normal amide bond at the carbon center bearing the trifluoromethyl group.

ADC-HA

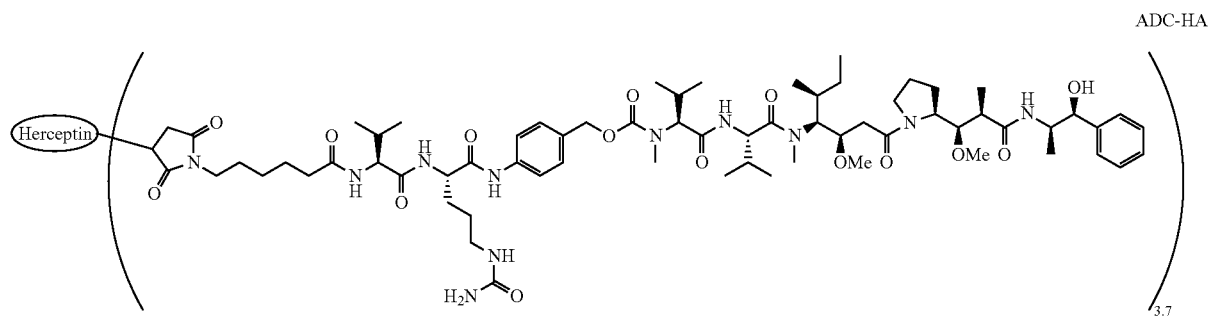

(b) A-431 Cell Line

Epidermoid carcinoma cell line A431 was grown in DMEM medium supplemented with 10% fetal bovine serum and maintained in an atmosphere of 5% $CO_2$ in a humidified 37° C. incubator.

The day before treatment, cells were collected and seeded into 96-well plates (2,000 cells per well). On the second day, cells were treated with a dilute concentration of Erbitux and ADCs of this invention (10, 3.33, 1.11, 0.37, 0.123, 0.041, 0.014, 0.0046 and 0.0015 μg/ml). Each treatment was performed in triplicate.

After 72 hours treatment, cell viability was assessed by Cell Titer-Glo kit (Promega) according to the manufacturer's instruction.

The study was compared to a control ADC (ADC-EA) with the normal amide bond at the carbon center bearing the trifluoromethyl group.

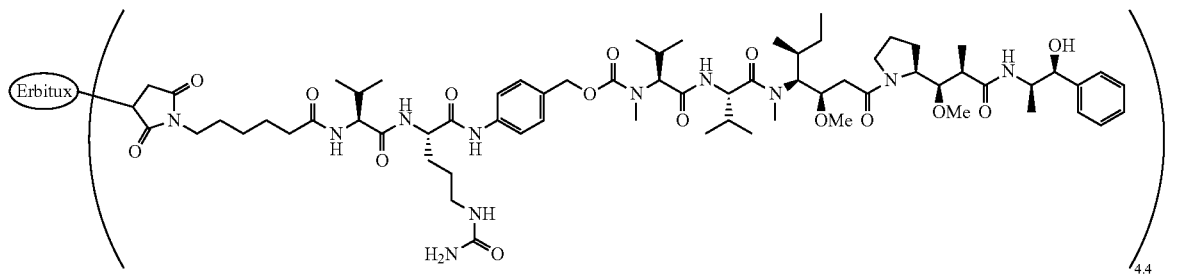

ADC-EA

In Vivo Efficacy Study (a) HCC1954 Xenograft Mice Model 7-8 Week old female NOD-SCID mice were injected with HCC1954 cells subcutaneously. Treatment was started 7 days after cell injection once the mean estimated tumor mass reached 153 mm³. Mice were grouped randomly according to the tumor volume and body weight (8 animals per group). Animals were treated with ADCs of this invention (15 mpk), Herceptin (15 mpk) as well as vehicle control on day 0 and day 15. Animals were euthanized on day 28 after the start of treatment, when the tumor volume of vehicle control group reached a mass of 1092 mm³.

(b) A-431 Xenograft Mice Model 6-8 Week old female Balb/c nude mice were injected with A431 cells subcutaneously. Treatment was started 10 days after cell injection once the mean estimated tumor mass reached 172 mm³. Mice were grouped randomly according to the tumor volume and body weight (8 animals per group). Animals were treated with ADCs of this invention (10 mpk), Erbitux (10 mpk) as well as vehicle control on day 0 and day 15. Animals were euthanized on day 25 after the start of treatment, when the tumor volume of vehicle control group reached a mass of 2000 mm³.

What is claimed is:

1. A linker of formula (I) to connect drugs to antibodies,

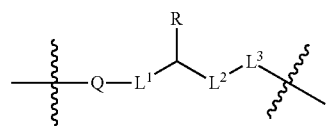

wherein,

R is selected from the group consisting of $CF_2H$, $CF_3$, $CF_2CF_3$, and $PhSO_2Me$;

Q is selected from the group consisting of

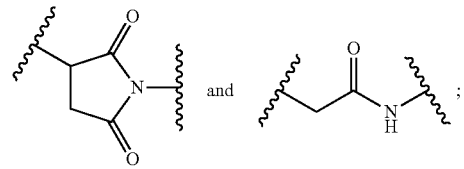 [SMILES: *C1CC(=O)N(*)C1=O ; *CC(=O)N*]

$L^1$ is selected from the group consisting of $-(CR^1R^2)_m-(CR^3R^4)-(CR^1R^2)_n-$, $-(CR^1R^2)_m-(CR^3R^4)-O-(CR^1R^2)_n-$, and $-[(CR^1R^2)(CR^1R^2)X]_p-(CR^1R^2)_q-$;

m is 1, 2, 3, or 4;

n is 1, 2, 3, or 4;

p is 1, 2, 3, 4, 5, or 6;

q is 1 or 2;

$R^1$ is selected from the group consisting of H and $C_{1-3}$ alkyl optionally substituted with 1, 2 or 3 of substituents independently selected from the group consisting of halogen, OH, $NH_2$, NHMe, and $NMe_2$;

$R^2$ is selected from the group consisting of H and $C_{1-3}$ alkyl optionally substituted with 1, 2 or 3 of substituents independently selected from the group consisting of halogen, OH, $NH_2$, NHMe, and $NMe_2$;

$R^3$ is selected from the group consisting of H and $C_{1-3}$ alkyl optionally substituted with 1, 2 or 3 of substituents independently selected from the group consisting of halogen, OH, $NH_2$, NHMe, and $NMe_2$;

$R^4$ is selected from the group consisting of H, $C_{1-3}$ alkyl, OH, $NR^5R^6$, $CO_2H$, $P(O)(OH)_2$, and $SO_3H$, said $C_{1-3}$ alkyl is optionally substituted with 1, 2 or 3 of substituents independently selected from the group consisting of halogen, OH, $NH_2$, NHMe, and $NMe_2$;

$R^5$ is selected from the group consisting of H and $C_{1-3}$ alkyl optionally substituted with 1, 2 or 3 of substituents independently selected from the group consisting of halogen, OH, $NH_2$, NHMe, and $NMe_2$;

$R^6$ is selected from the group consisting of H and $C_{1-3}$ alkyl optionally substituted with 1, 2 or 3 of substituents independently selected from the group consisting of halogen, OH, $NH_2$, NHMe, and $NMe_2$;

X is selected from the group consisting of $NR^7$, O, $S(O)_r$;

r is 0, 1, or 2;

$R^7$ is selected from the group consisting of H and $C_{1-3}$ alkyl optionally substituted with 1, 2 or 3 of substituents independently selected from the group consisting of halogen, OH, $NH_2$, NHMe, and $NMe_2$;

$L^2$ is a di-peptide unit selected from

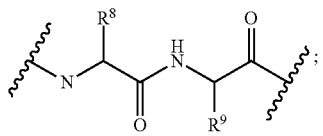

$R^8$ is selected from the group consisting of methyl, propyl, isopropyl, sec-butyl, benzyl, and

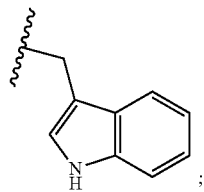 [SMILES: *Cc1c[nH]c2ccccc12]

$R^9$ is selected from the group consisting of $(CH_2)_4NH_2$, $(CH_2)_3NHCONH_2$, $(CH_2)_3NHC(=NH)NH_2$,

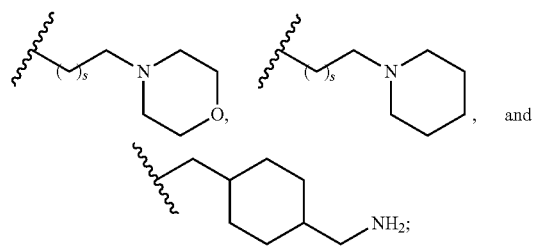

s is 0, 1, 2, 3, or 4;
$L^3$ is a self-immolative unit selected from the group consisting of

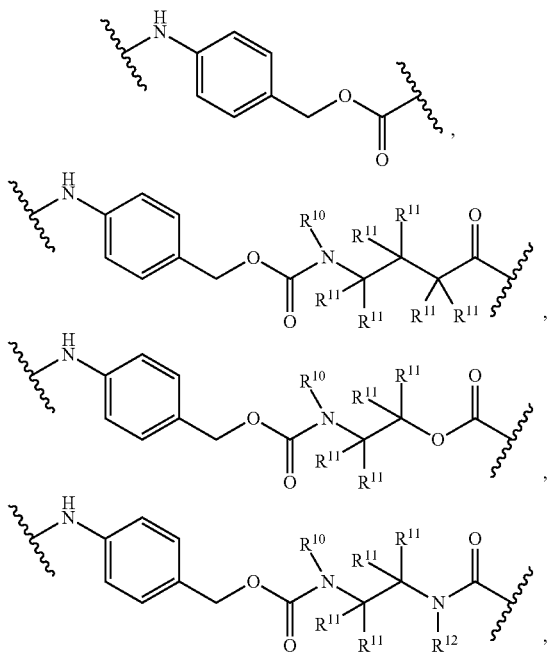

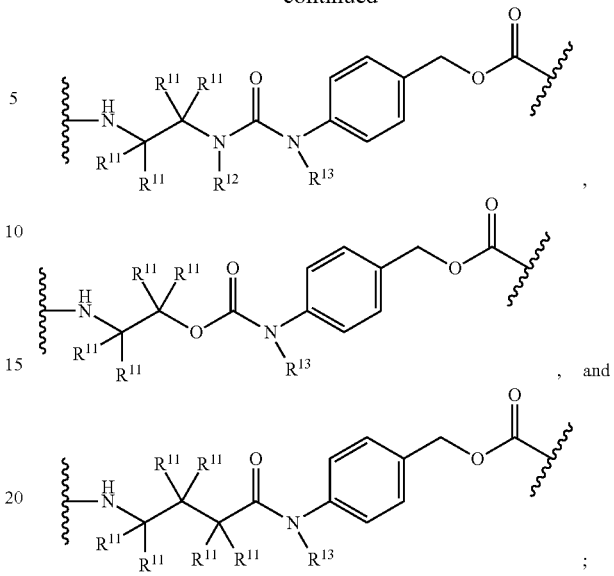

$R^{10}$ is selected from the group consisting of H and $C_{1-3}$ alkyl optionally substituted with 1, 2 or 3 of substituents independently selected from the group consisting of halogen, OH, $NH_2$, NHMe, and $NMe_2$;

each $R^{11}$ is independently selected from the group consisting of H and $C_{1-3}$ alkyl optionally substituted with 1, 2 or 3 of substituents independently selected from the group consisting of halogen, OH, $NH_2$, NHMe, and $NMe_2$;

two geminal $R^{11}$ may be optionally joined together to form a 3-6 membered ring with a carbon atom to which they are attached;

two adjacent $R^{11}$ may be optionally joined together to form a 5-7 membered ring with a carbon atom to which they are attached;

$R^{12}$ is selected from the group consisting of H and $C_{1-3}$ alkyl optionally substituted with 1, 2 or 3 of substituents independently selected from the group consisting of halogen, OH, $NH_2$, NHMe, and $NMe_2$; and $R^{13}$ is selected from the group consisting of H and $C_{1-3}$ alkyl optionally substituted with 1, 2 or 3 of substituents independently selected from the group consisting of halogen, OH, $NH_2$, NHMe, and $NMe_2$.

2. A drug-linker conjugate of formula (II),

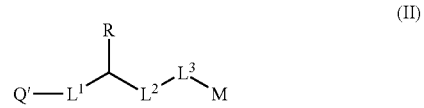

wherein,
Q' is selected from the group consisting of

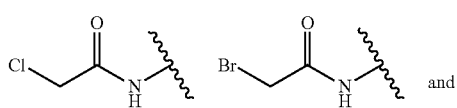

-continued

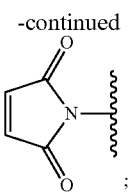

M is a drug; and
other variables are as defined in claim 1.

3. An anti-drug conjugate (ADC) of formula (III) containing the linker of claim 1,

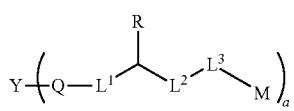

(III)

wherein,
Y is an antibody;
a is an integer or decimal selected from 1-8;
M is a drug; and
other variables are as defined in claim 1.

4. The linker of claim 1, wherein the antibody is selected from the group consisting of a resurfaced monoclonal antibody, a resurfaced single chain monoclonal antibody, or a resurfaced monoclonal antibody fragment;
or the antibody is selected from the group consisting of a humanized monoclonal antibody, a humanized single chain monoclonal antibody, or a humanized monoclonal antibody fragment;
or the antibody is selected from the group consisting of a chimeric antibody, a chimeric antibody fragment, a domain antibody, or a domain antibody fragment thereof;
or the antibody is selected from the group consisting of MY9, anti-B4, EpCAM, CD2, CD3, CD4, CD5, CD6, CD11, CD19, CD20, CD22, CD26, CD30, CD33, CD37, CD38, CD40, CD44, CD56, CD79, CD105, CD138, EphA receptors, EphB receptors, EGFR, EGFRvIII, HER2, HER3, mesothelin, cripto, alpha$_v$-beta$_3$, alpha$_v$beta$_5$, alpha$_v$beta$_6$ integrin or C242;
or the antibody is selected from the group consisting of My9-6, B4, C242, N901, DS6, EphA2 receptor, CD38, IGF-IR, CNTO 95, B-B4, Trastuzumab, Tertuzumab, Bevatuzumab, Sibrotuzumab, Rituximab, and Adalimumab;
or the antibody is selected from the group consisting of Herceptin and Erbitux.

5. The linker of claim 1, wherein the antibody binds to target cells selected from tumor cells; virus infected cells, microorganism infected cells, parasite infected cells, autoimmune cells, activated cells, myeloid cells, activated T-cells, B cells, or melanocytes; cells expressing one or more of IGF-IR, CanAg, EGFR, MUCI, MUCI 6, VEGF, TF, MY9, anti-B4, EpCAM, CD2, CD3, CD4, CD5, CD6, CD11, CD11a, CD18, CD19, CD20, CD22, CD26, CD30, CD33, CD37, CD38, CD40, CD44, CD56, CD70, CD79, CD105, CD138, EphA receptors, EphB receptors, EGFRvIII, HER2/neu, HER3, mesothelin, cripto, alpha$_v$-beta$_3$ integrin, alpha$_v$beta$_5$ integrin, alpha$_v$beta$_6$integrin, Apo2, and C242 antigens; or cells expressing insulin growth factor receptor, epidermal growth factor receptor, and folate receptor.

6. The linker of claim 1, wherein the drug is a cytotoxic drug, or the drug is a diagnostic or detection reagent.

7. The linker of claim 1, wherein $L^1$ is selected from the group consisting of:

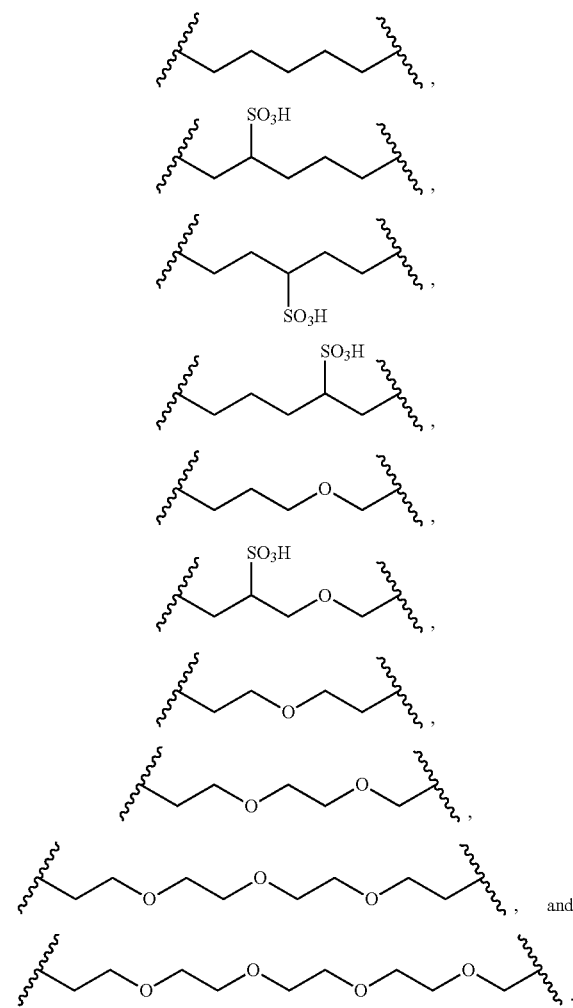

and

8. The linker of claim 1, wherein $L^2$ is selected from the group consisting of

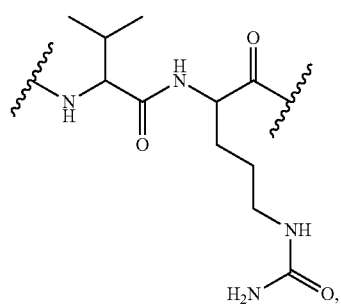

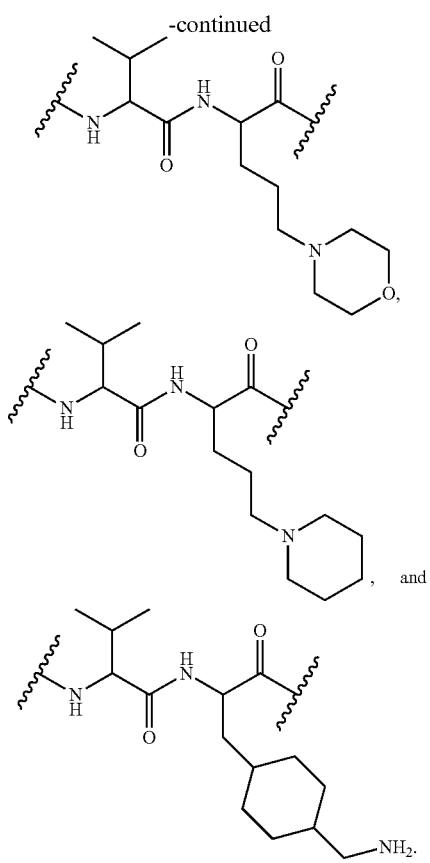
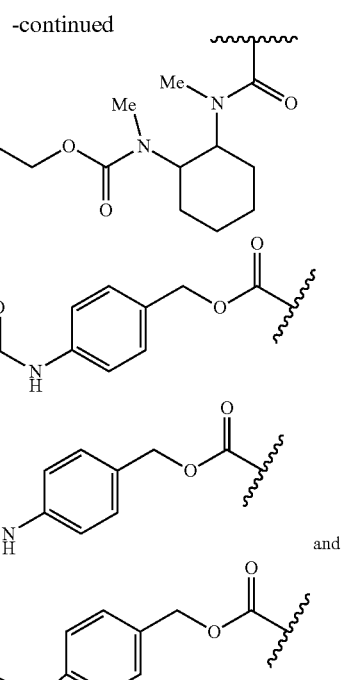
ABA-PAB
9. The linker of claim 1, wherein the ring formed by two geminal R$^{11}$ or two adjacent R$^{11}$ is cyclohexyl.
10. The linker of claim 1, wherein L$^3$ is selected from the group consisting of
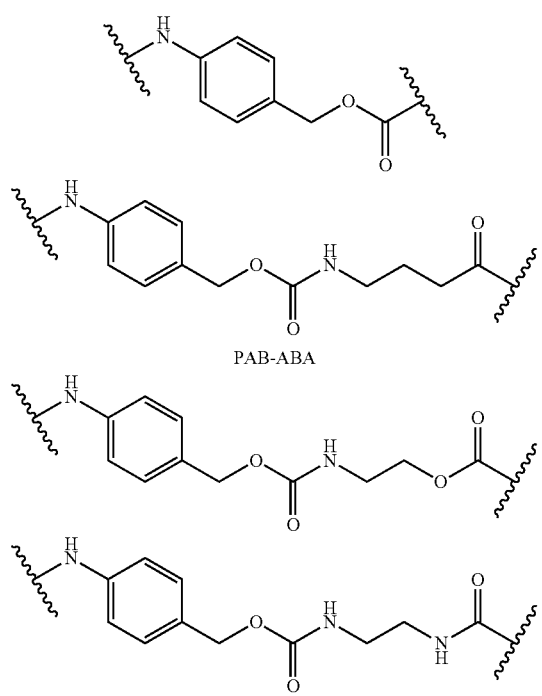
PAB-ABA
11. The linker of claim 1, wherein the moiety of
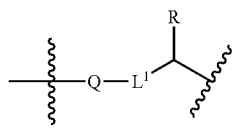
is selected from the group consisting of
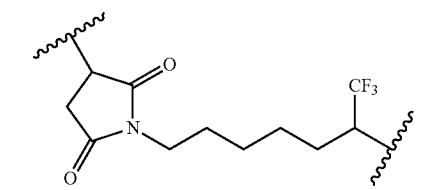
12. The linker of claim 1, wherein the linker is selected from the group consisting of

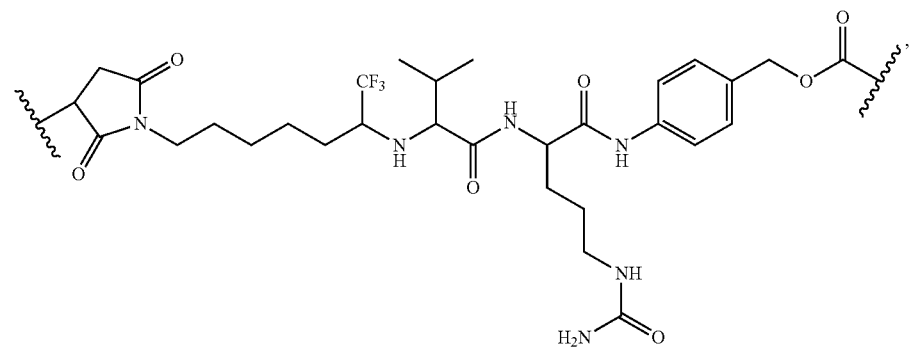
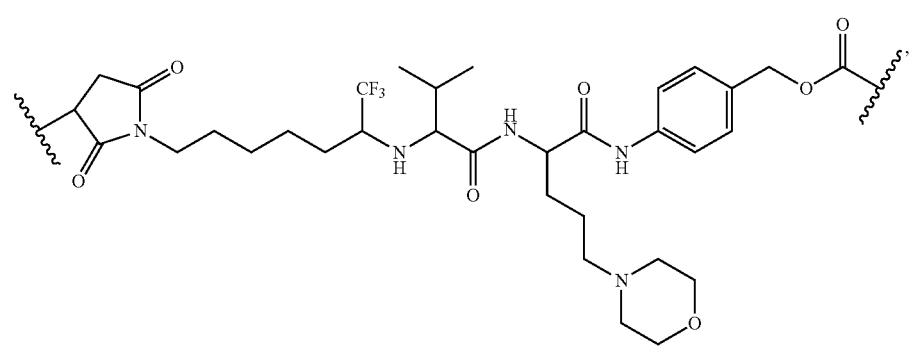
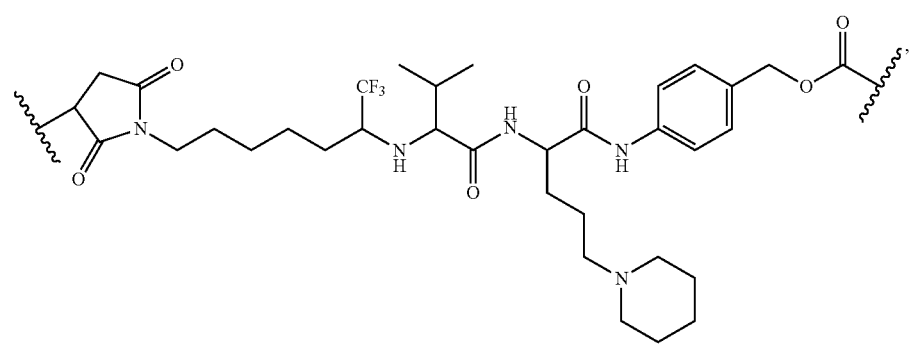
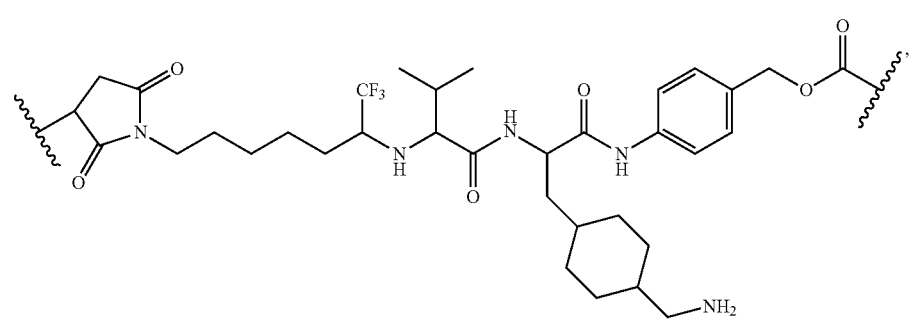
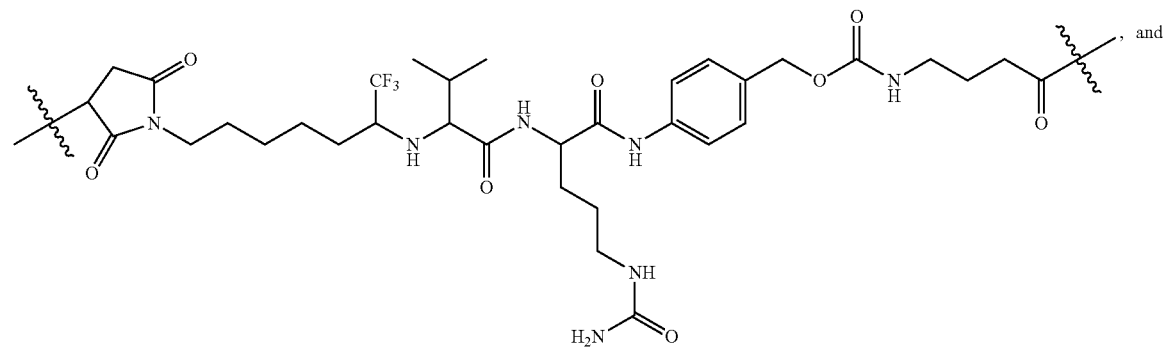

-continued
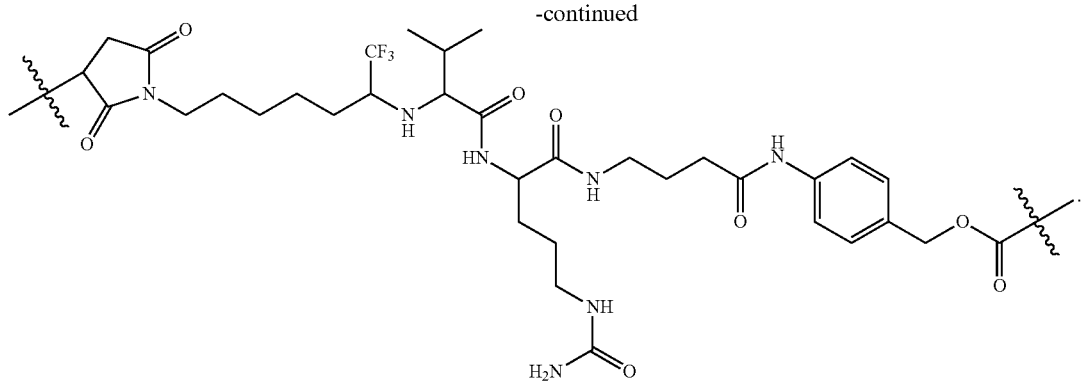
13. The drug-linker conjugate of claim 2, it is selected from the group consisting of
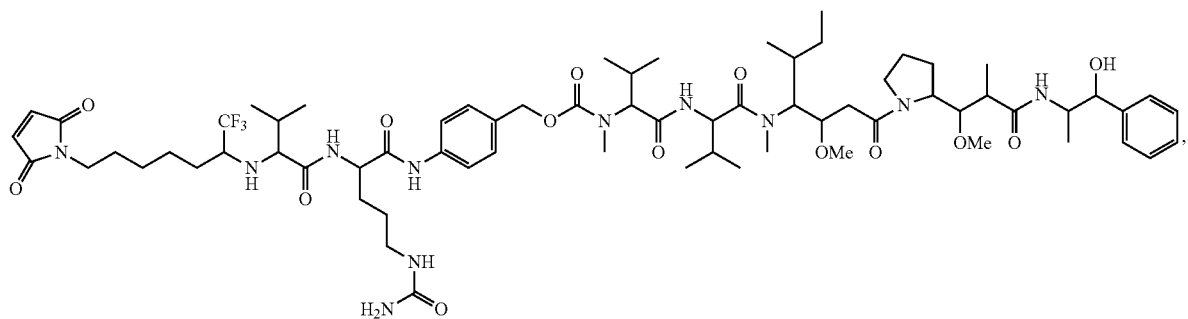,
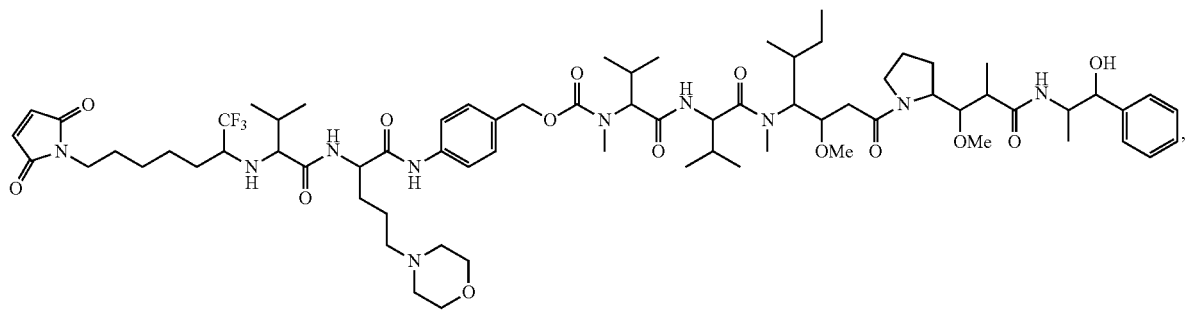,
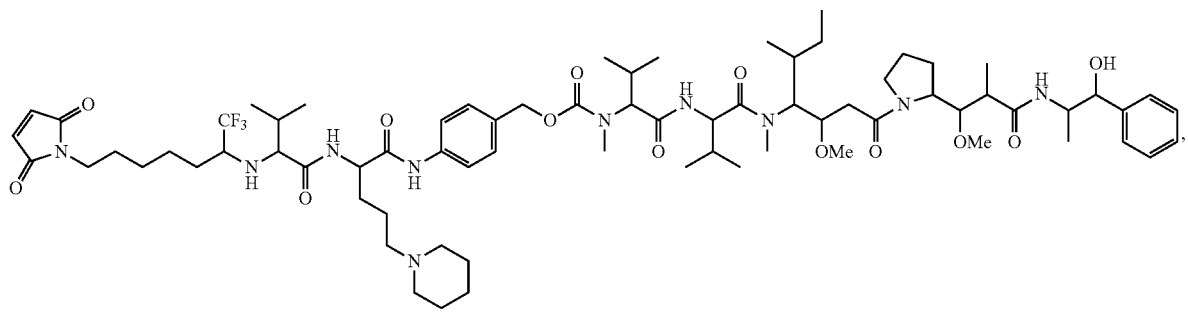,

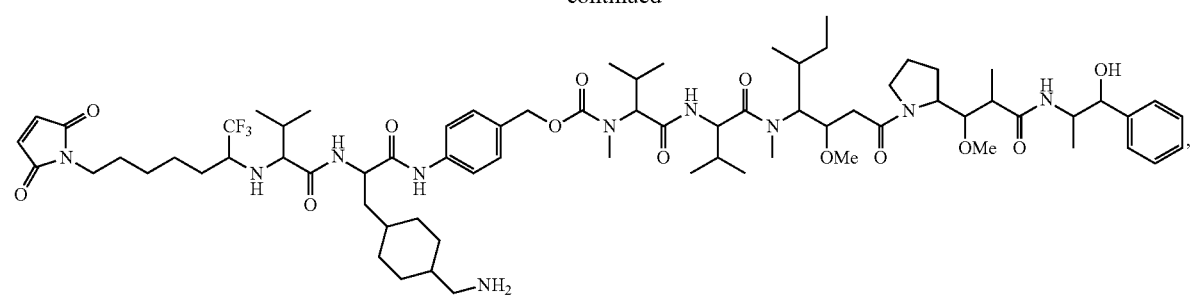
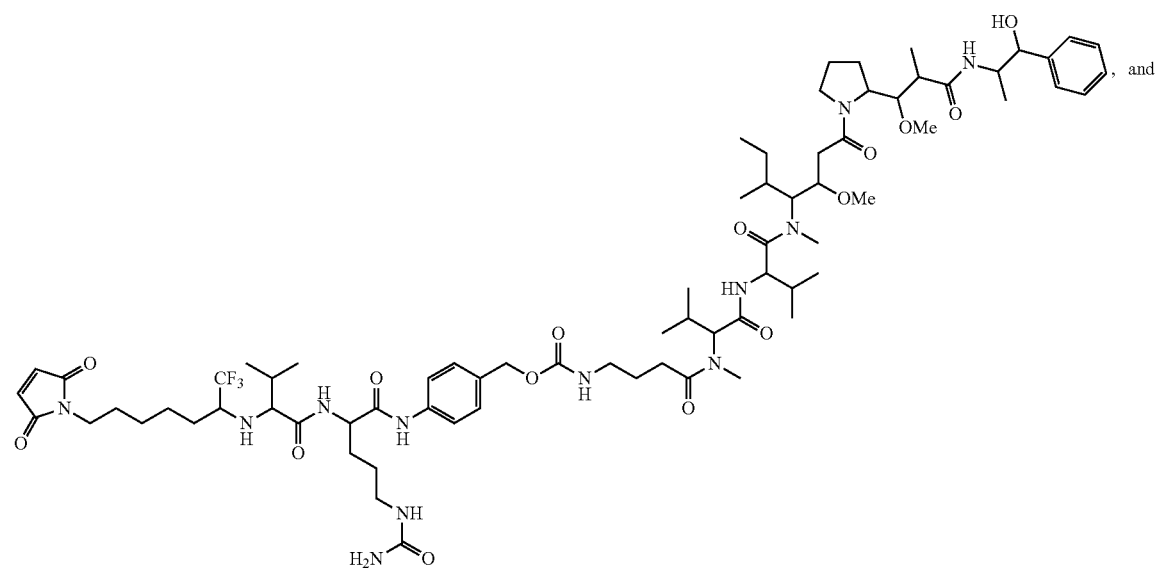
, and
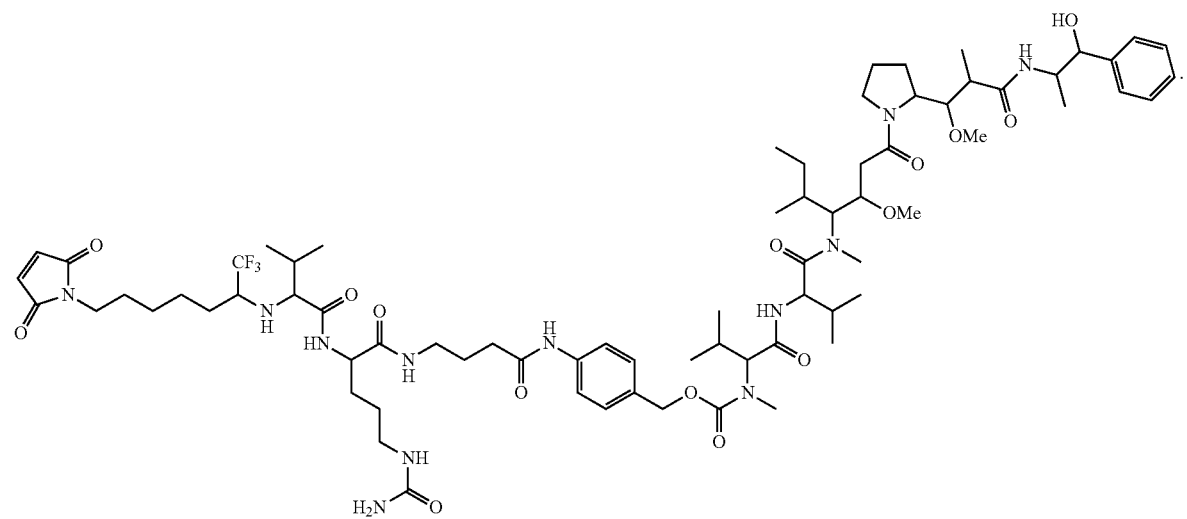

14. The ADC of claim 3, it is selected from the group consisting of
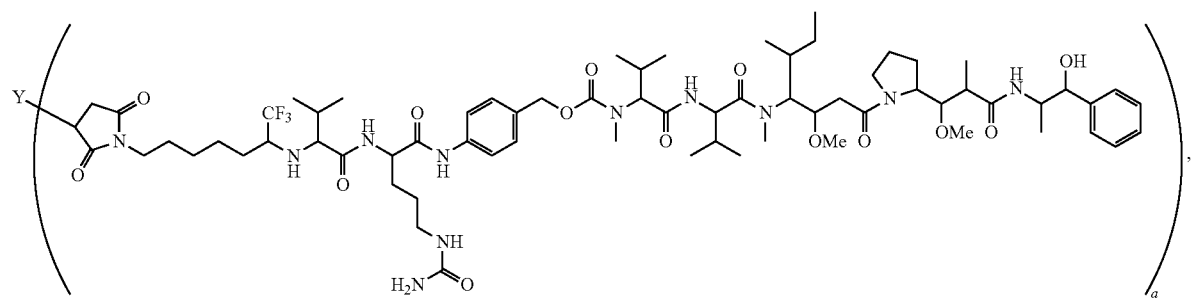
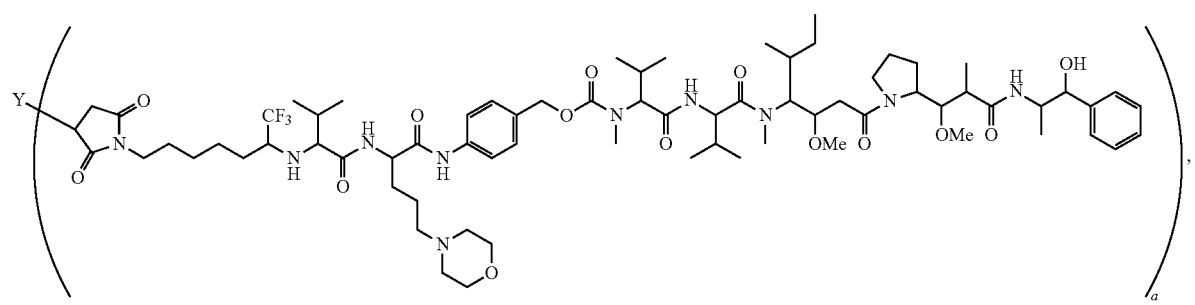
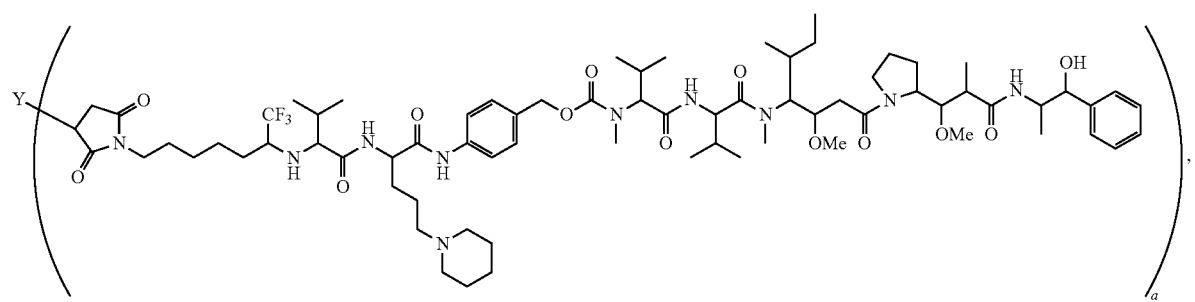
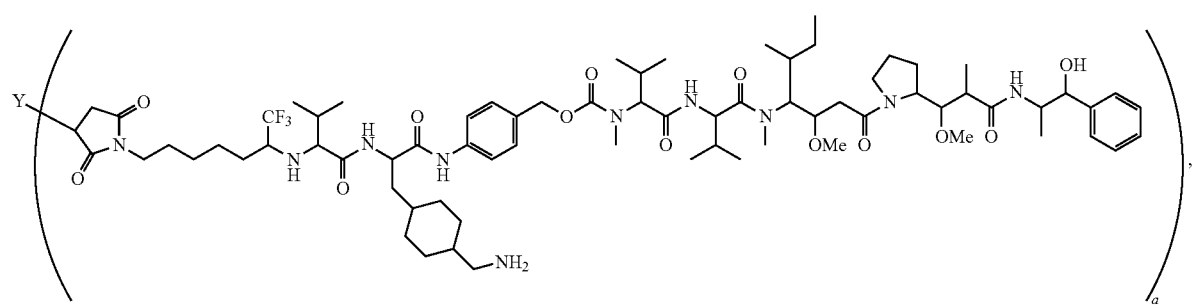

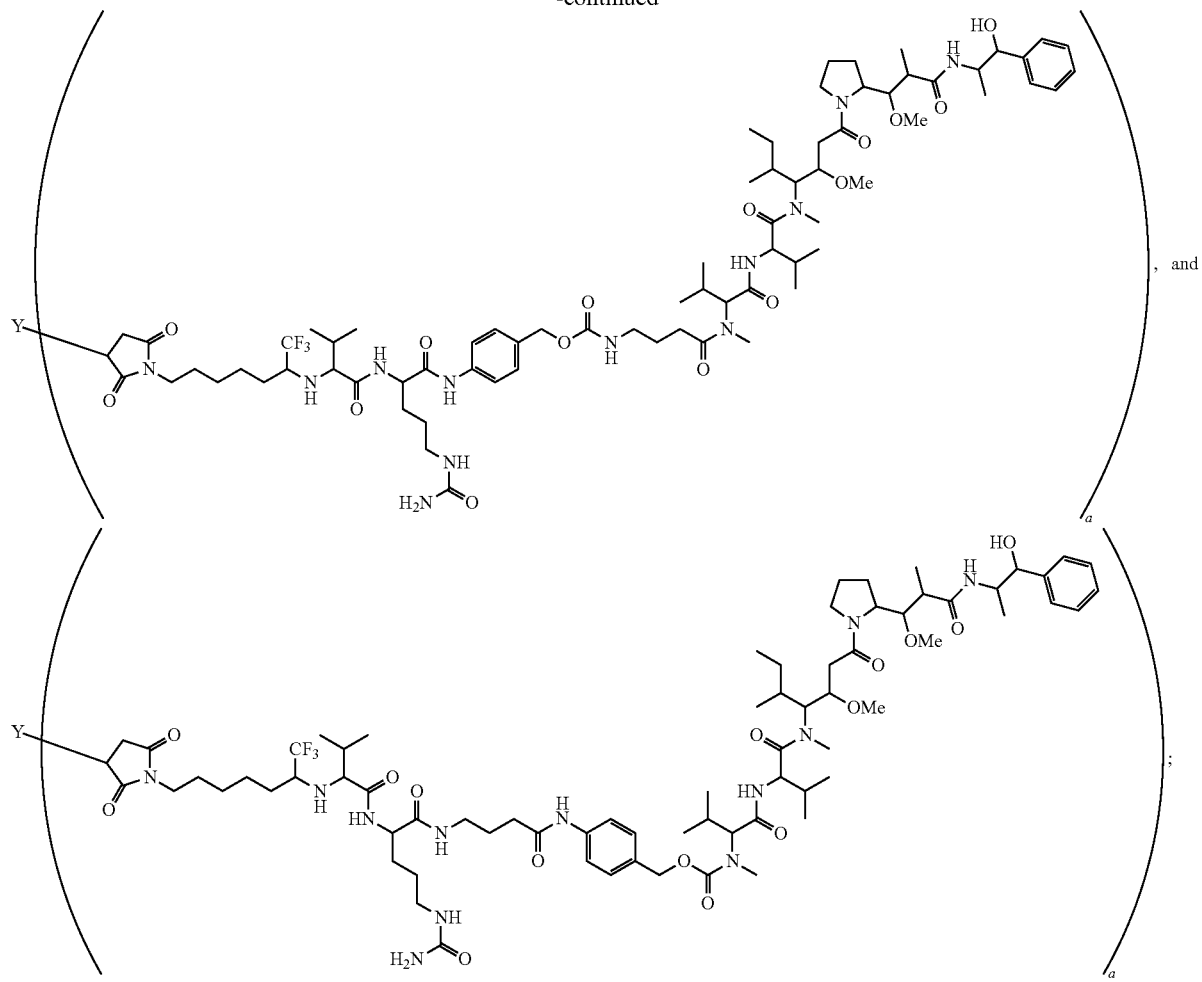

Y is an antibody, a is an integer or decimal selected from 1-8.

15. A pharmaceutical composition comprising an effective amount of the ADC of claim 3 and a pharmaceutically acceptable carrier, diluent or excipient.

16. A process for treating a patient in need of a medicament for cancers, comprising administering to the patient a medicament comprising an effective amount of the linker in claim 1.

17. A process for treating or diagnosising a patient in need of a medicament for cancers, comprising administrating to the patient a medicament comprising an effective amount of the ADC of claim 3.

18. An intermediate compound for the synthesis of the drug-linker conjugate of formula (II) in claim 2, comprising:

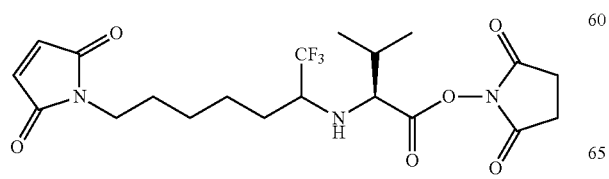

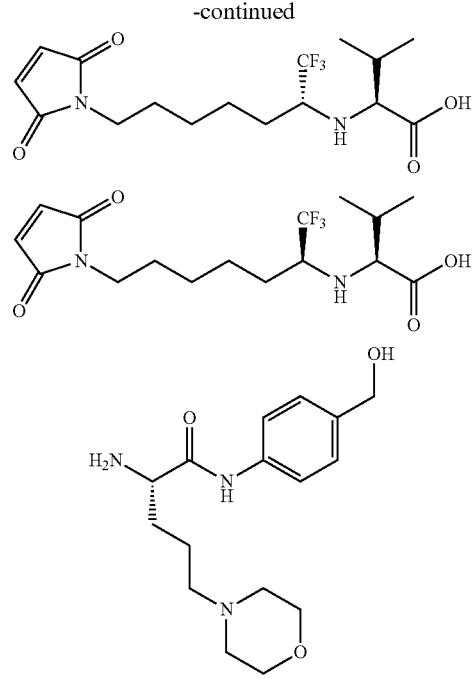

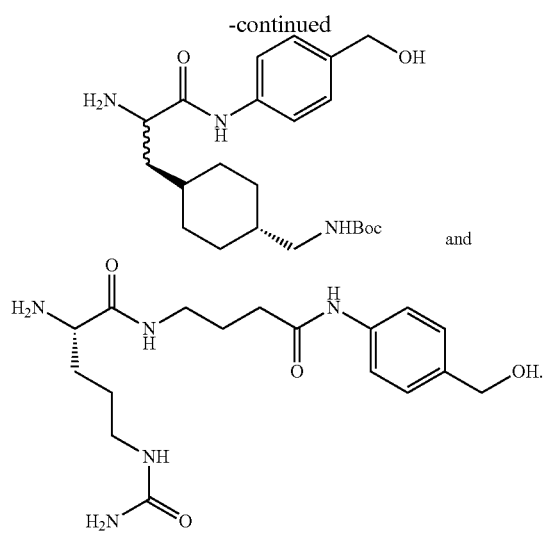 and

19. The linker of claim 5, wherein the tumor cells are selected from breast cancer cells, prostate cancer cells, ovarian cancer cells, colorectal cancer cells, gastric cancer cells, squamous cancer cells, small-cell lung cancer cells, and testicular cancer cells.

20. The linker of claim 6, wherein the drug is selected from the group consisting of maytansinoid, DNA-binding drug and its analog, calicheamicin, doxorubicin and its analog, vinca alkaloid, cryptophycin, dolastatin, auristatin and analog thereof, tubulysin, epothilone, taxoid and siRNA; or the drug is a radio-labeled compound.

21. The linker of claim 20, wherein the DNA-binding drug is CC-1065; or the drug is labeled with $^3$H, $^{18}$F, $^{11}$C, $^{13}$N, $^{15}$O, $^{201}$Tl, $^{32}$P, $^{51}$Cr, $^{67}$Ga, $^{123}$I, $^{125}$I, $^{131}$I, $^{132}$I, $^{131}$Cs, $^{113}$Xe, $^{133}$Xe, $^{169}$Yb, $^{198}$Au, $^{203}$Hg, $^{99m}$Tc, $^{113m}$In, $^{133m}$In, $^{75}$Se, $^{186}$Re, $^{153}$Sm, and $^{89}$Sr.

22. The drug-linker conjugate of claim 6, wherein M is selected from the group consisting of

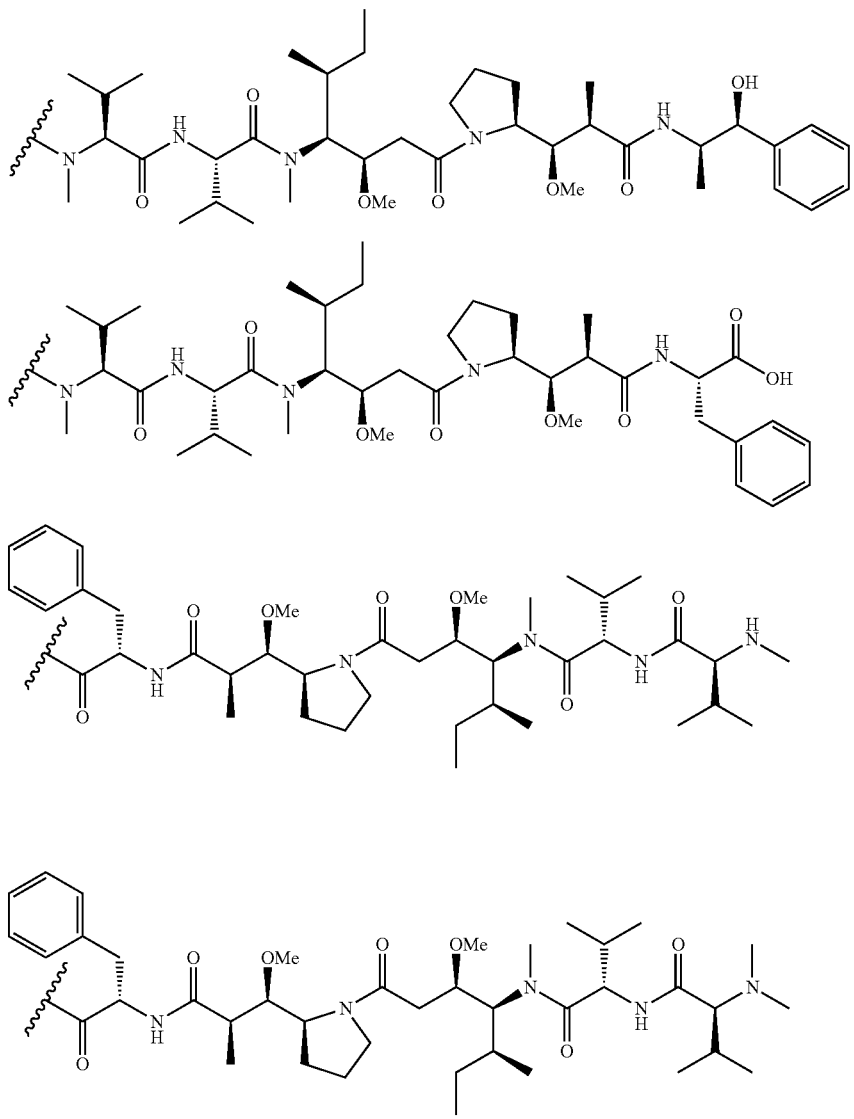

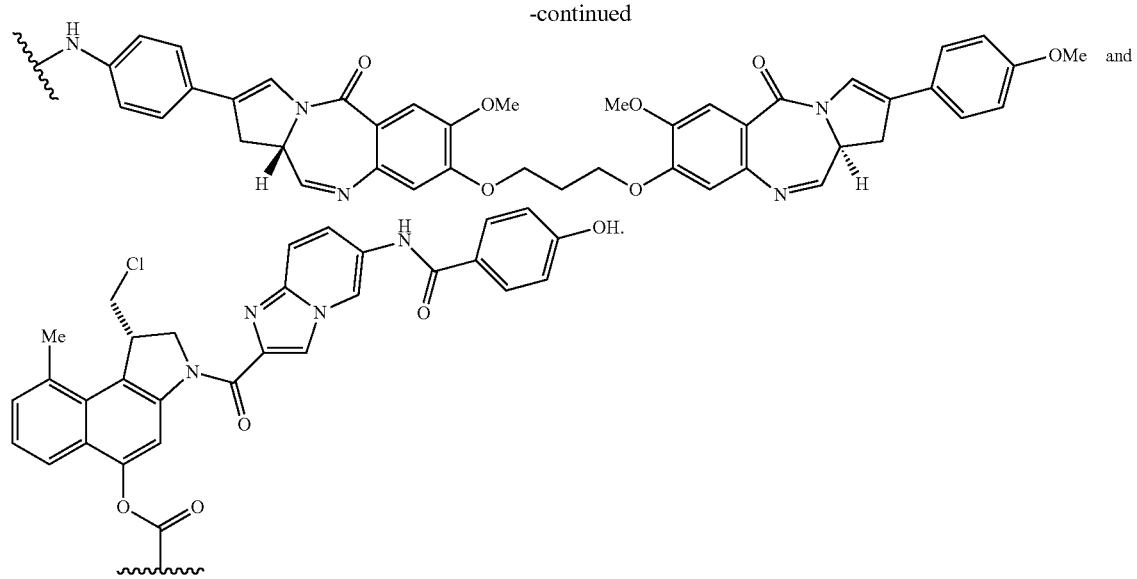
23. The linker of claim 8, wherein $L^2$ is selected from the group consisting of
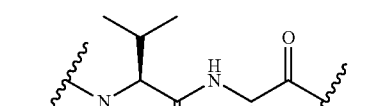
Val-Cit
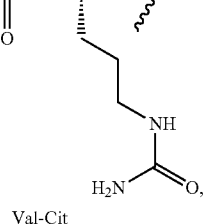
DP1
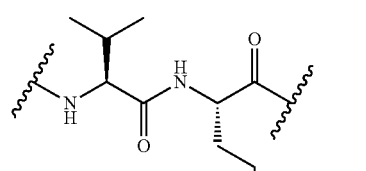
DP2
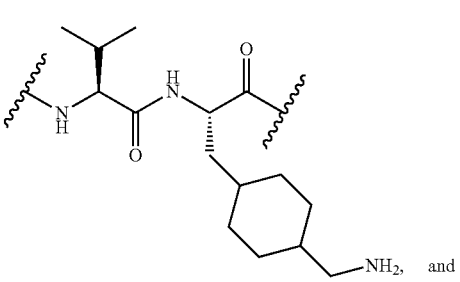
DP3
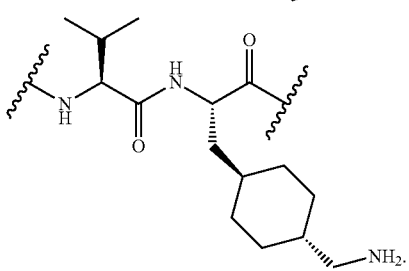
24. The drug-linker conjugate of claim 2, the moiety of
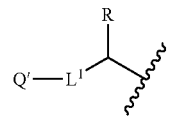
is selected from the group consisting of
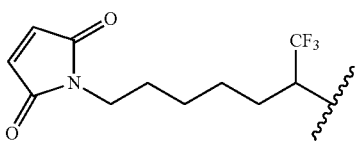

137
-continued
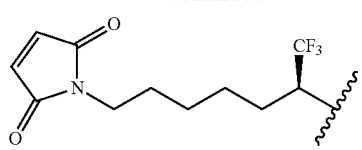
and
138
-continued
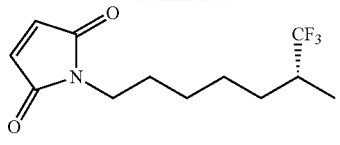
.
25. The linker of claim 12, wherein the linker is selected from the group consisting of
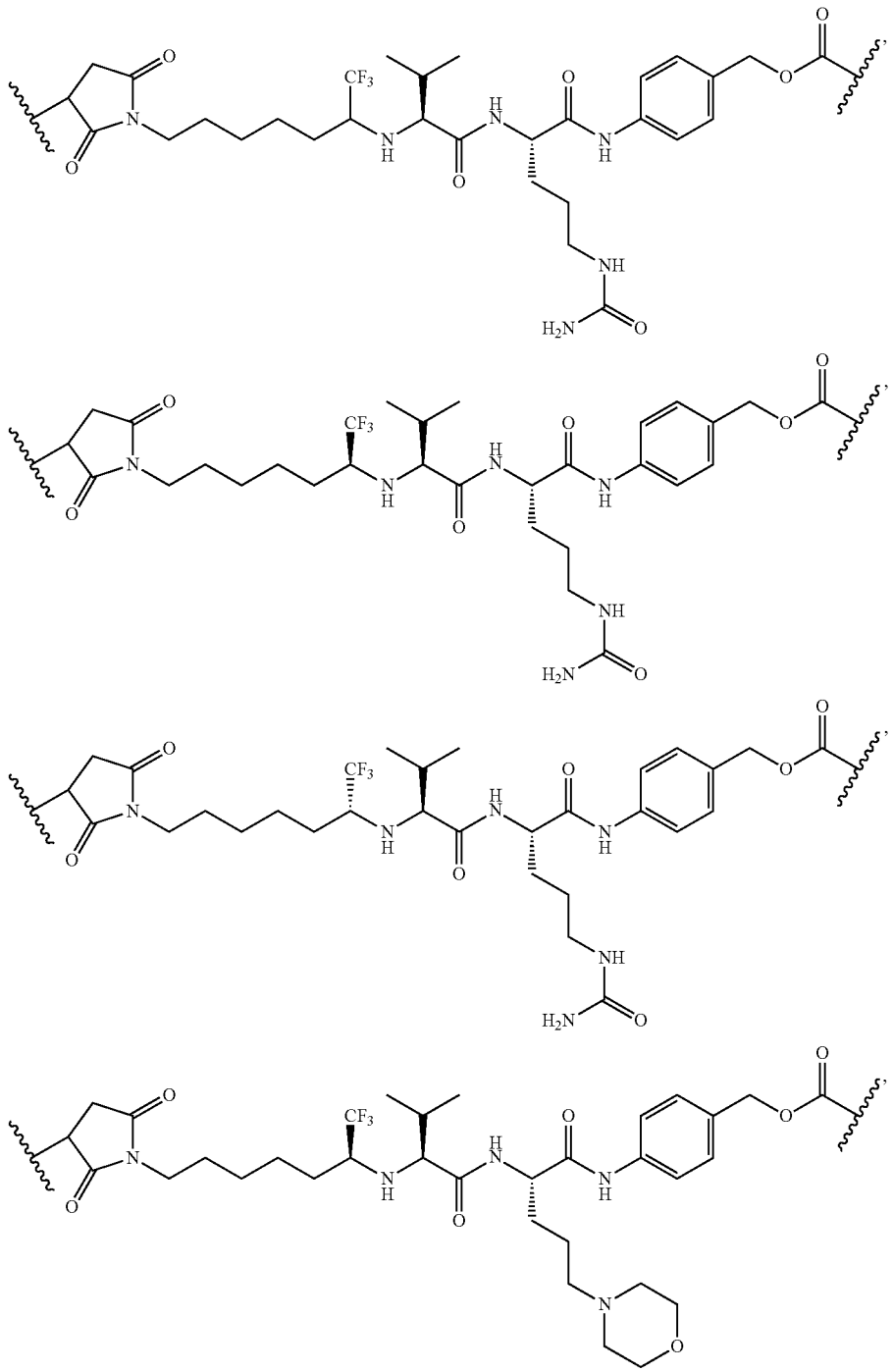

-continued
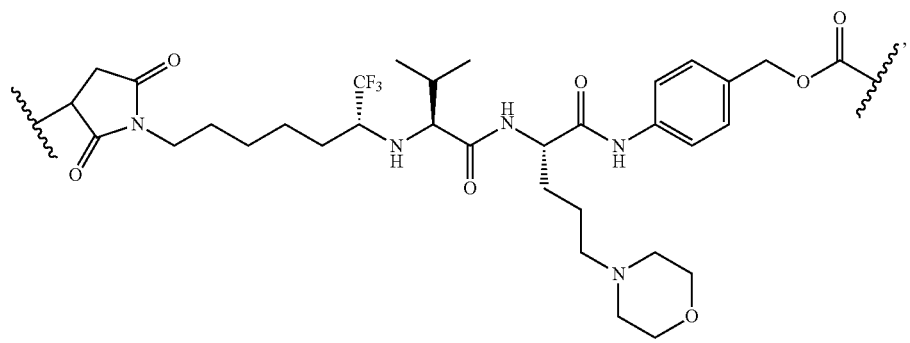
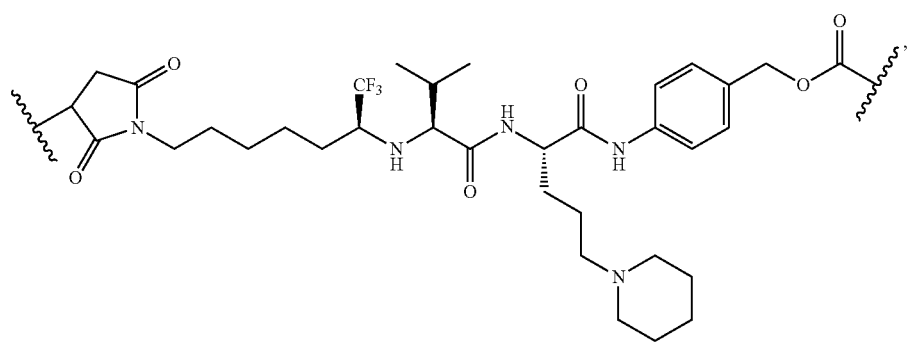
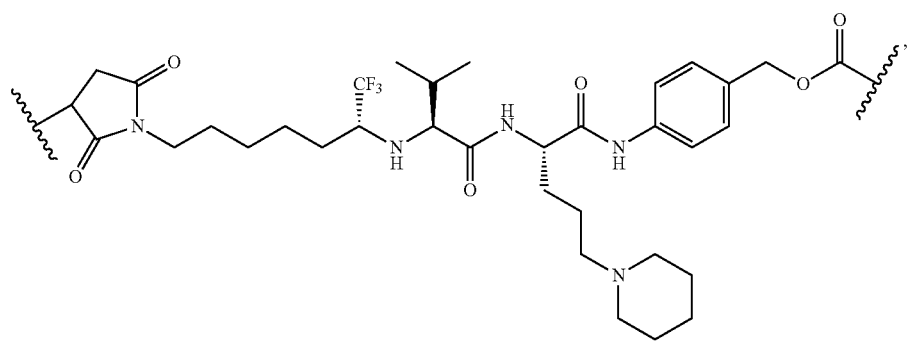
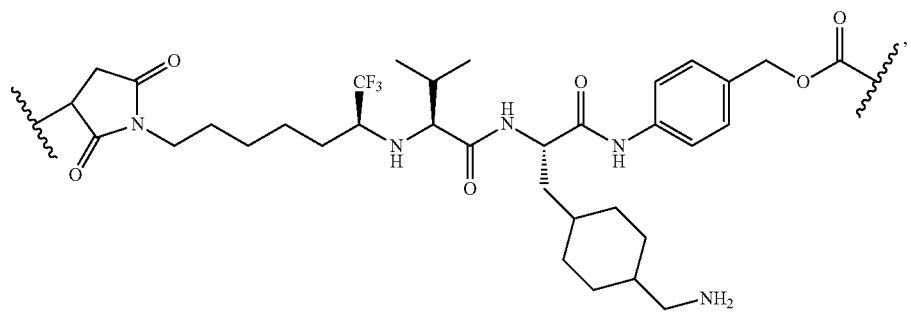
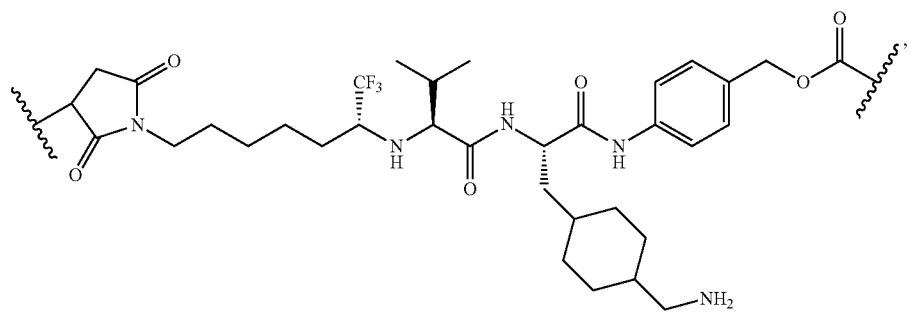

-continued
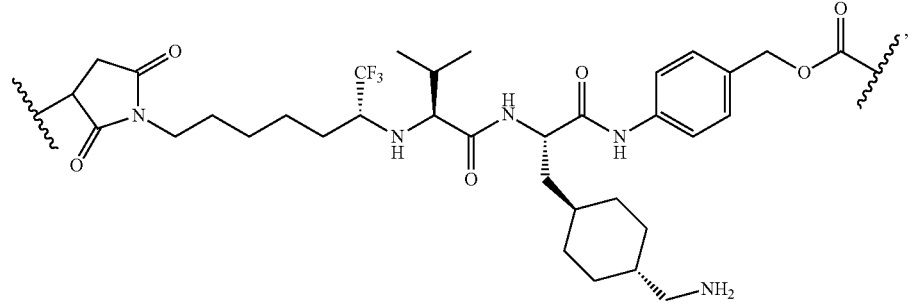
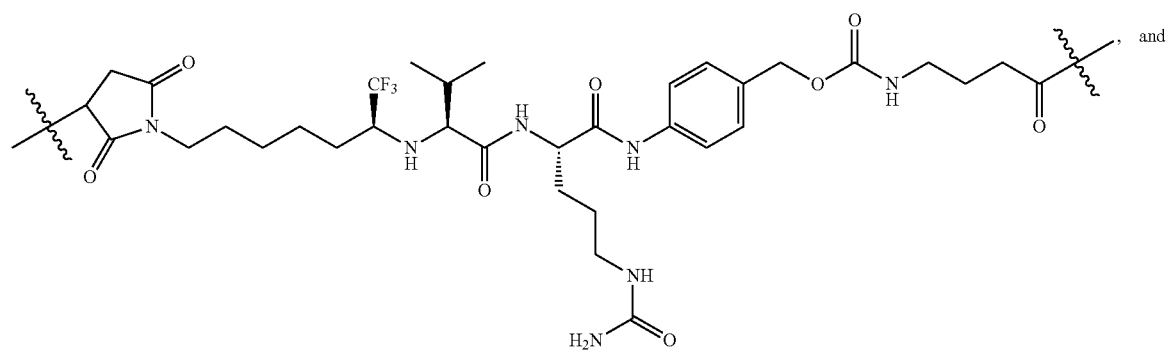
, and
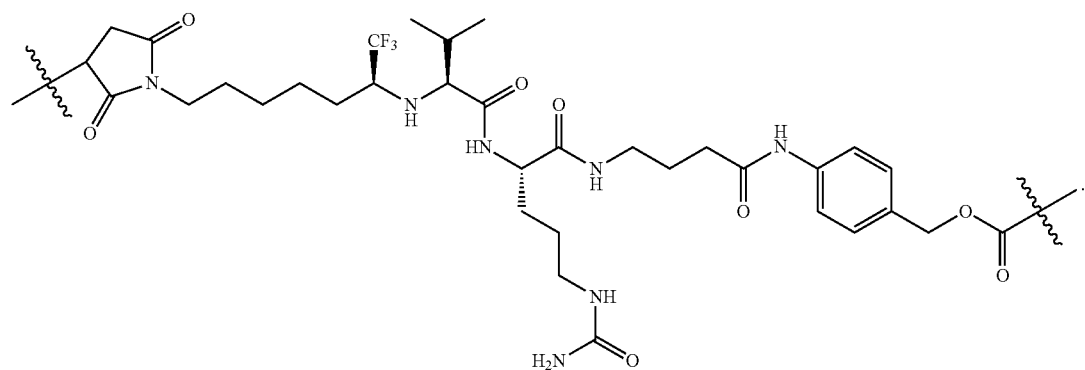
26. The drug-linker conjugate of claim 13, it is selected from the group consisting of
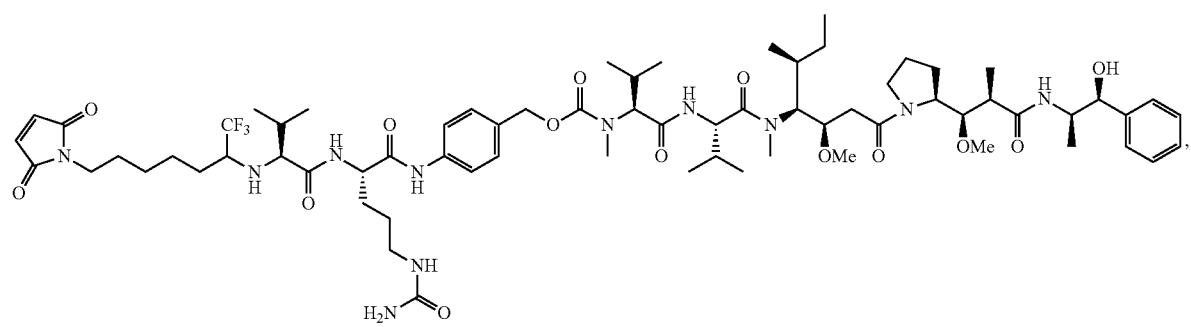

-continued
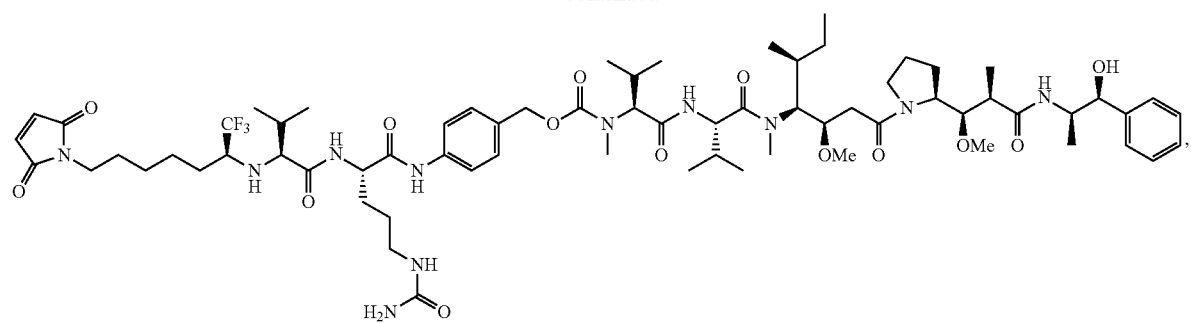
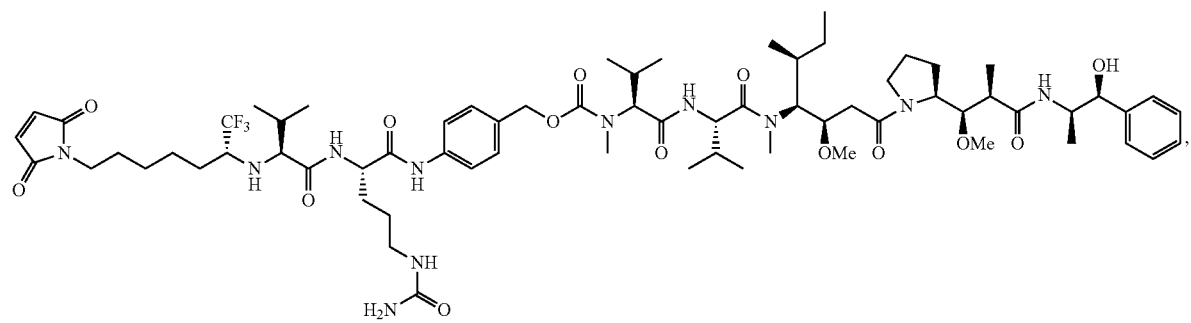
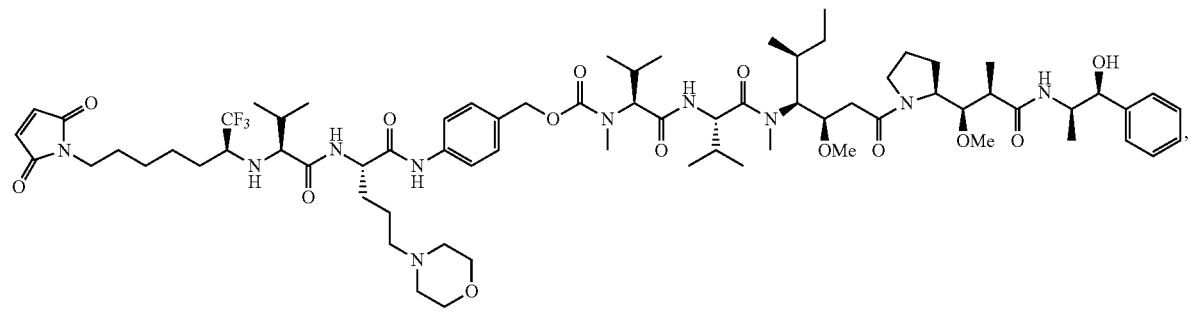
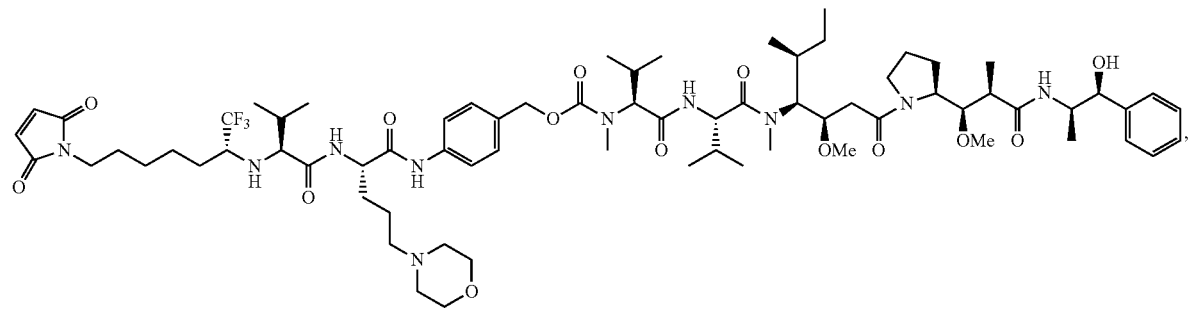
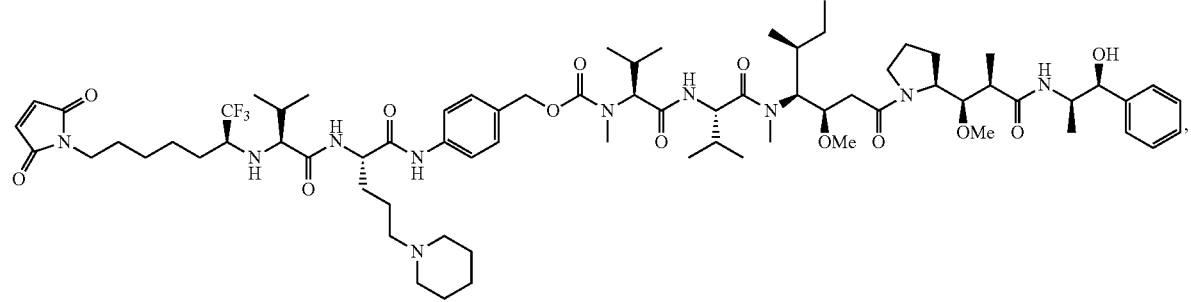

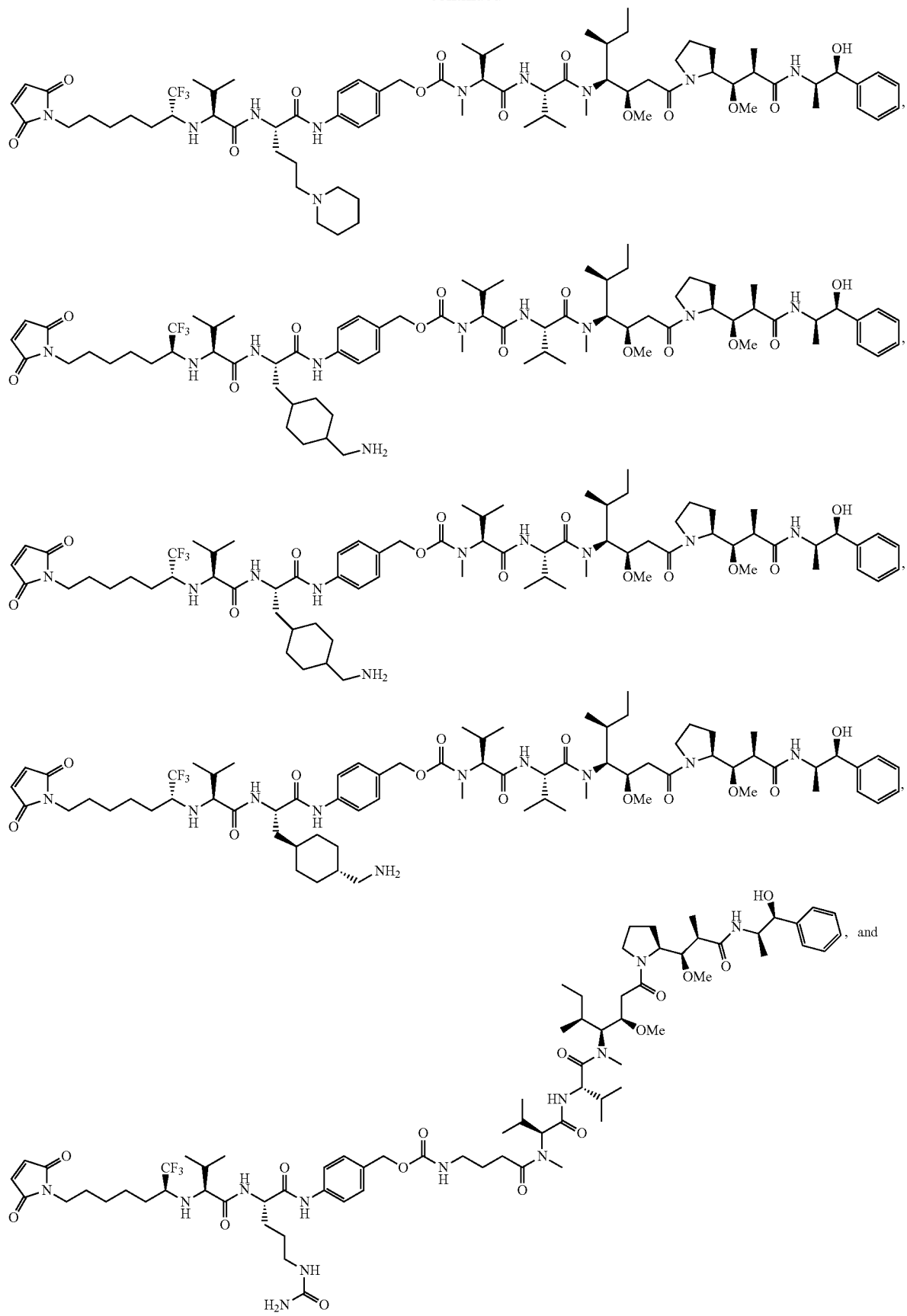

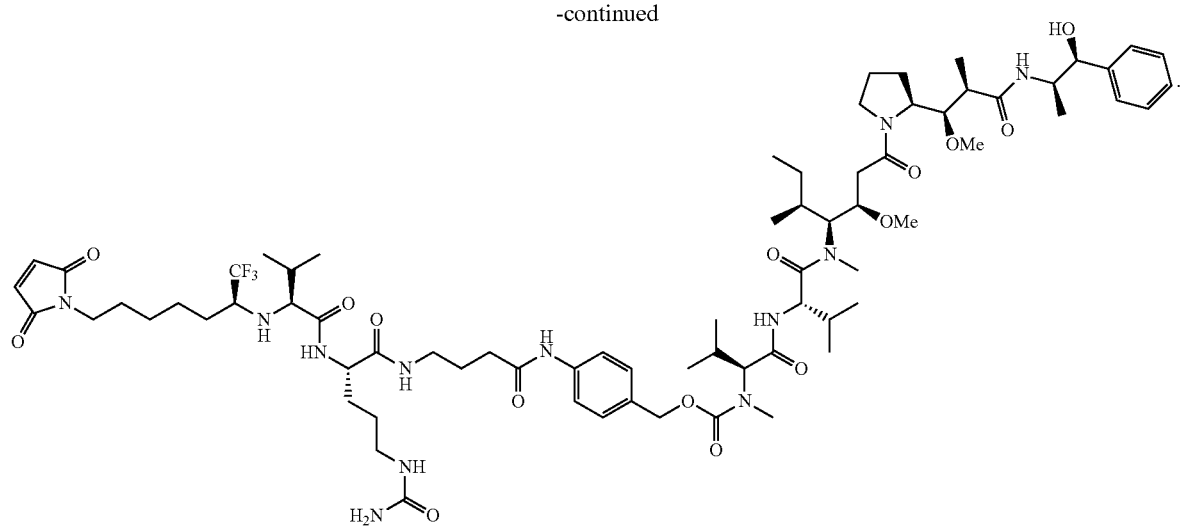
27. The ADC of claim 14, it is selected from the group consisting of
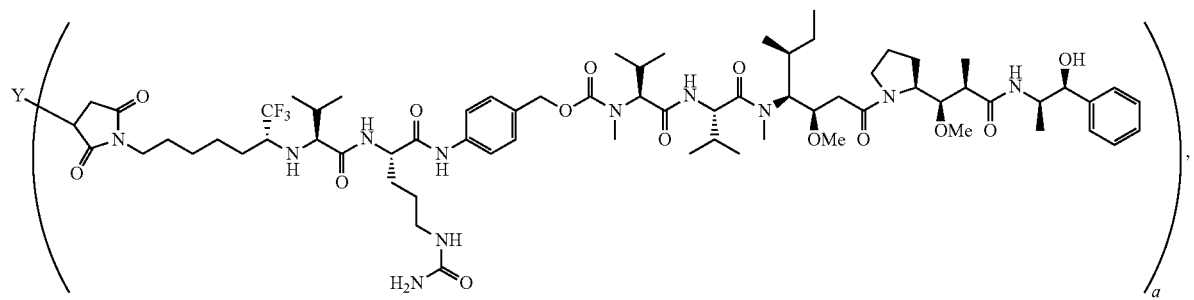
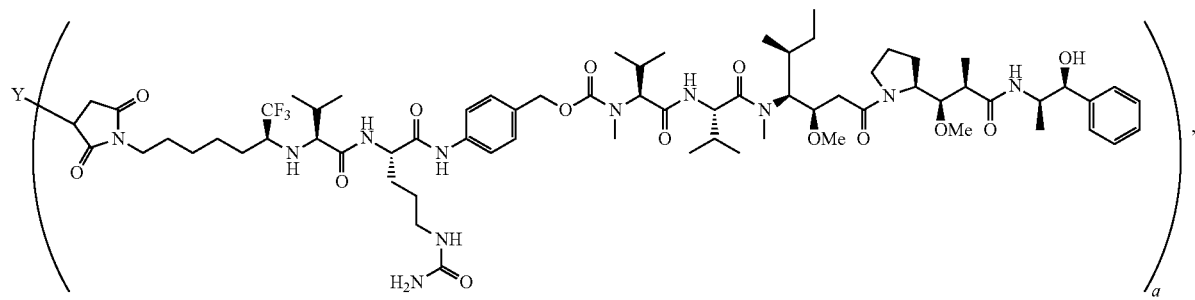
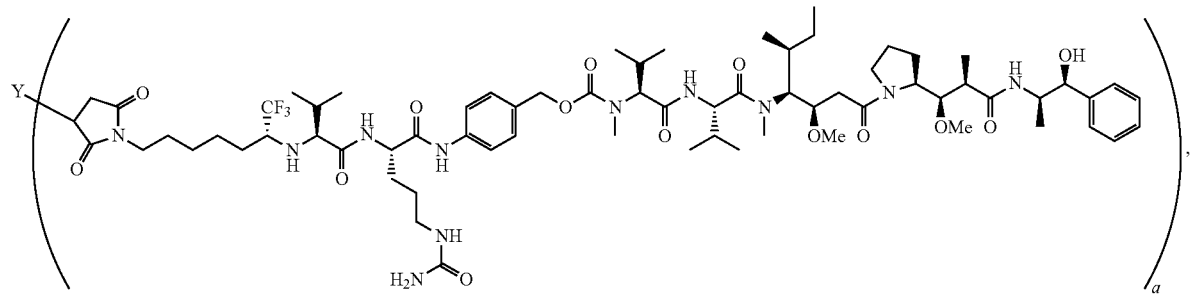

-continued
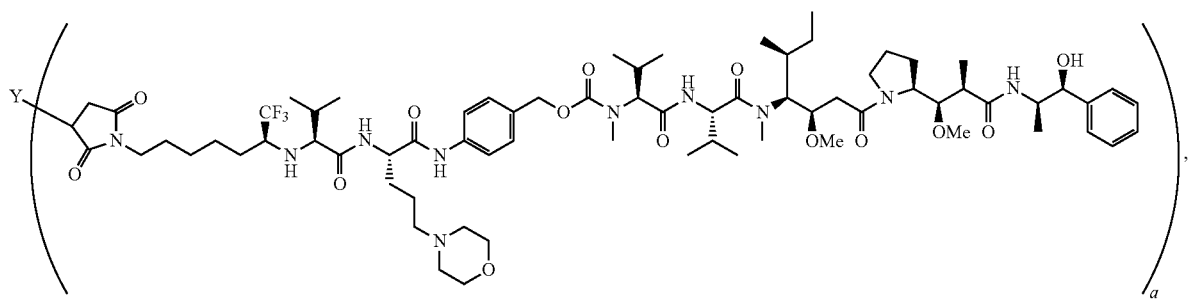
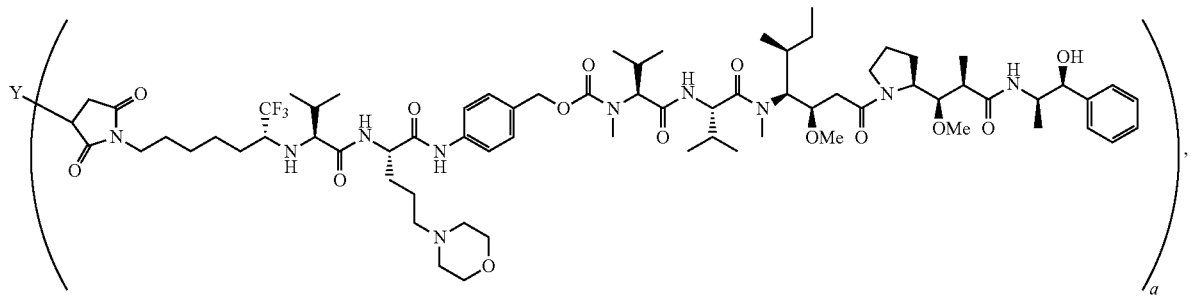
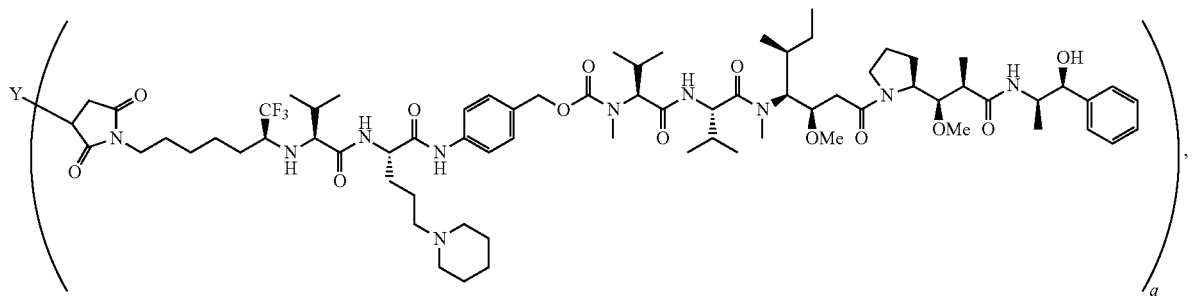
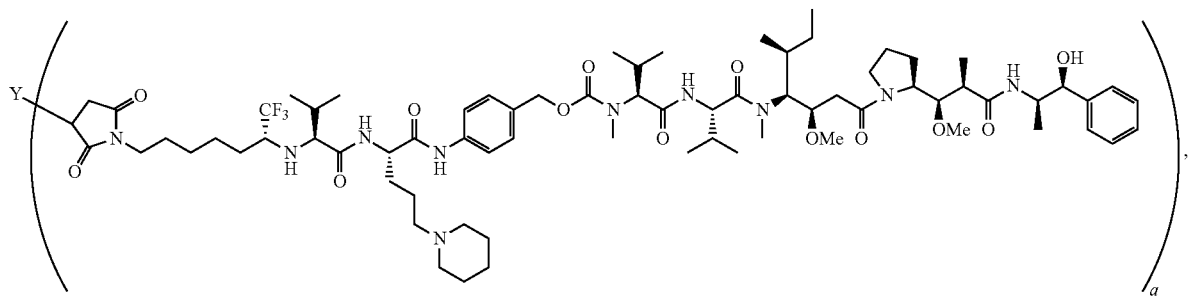
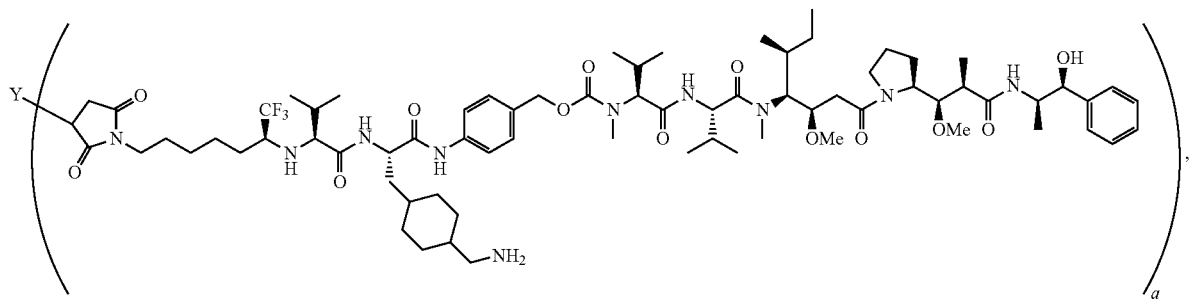

-continued
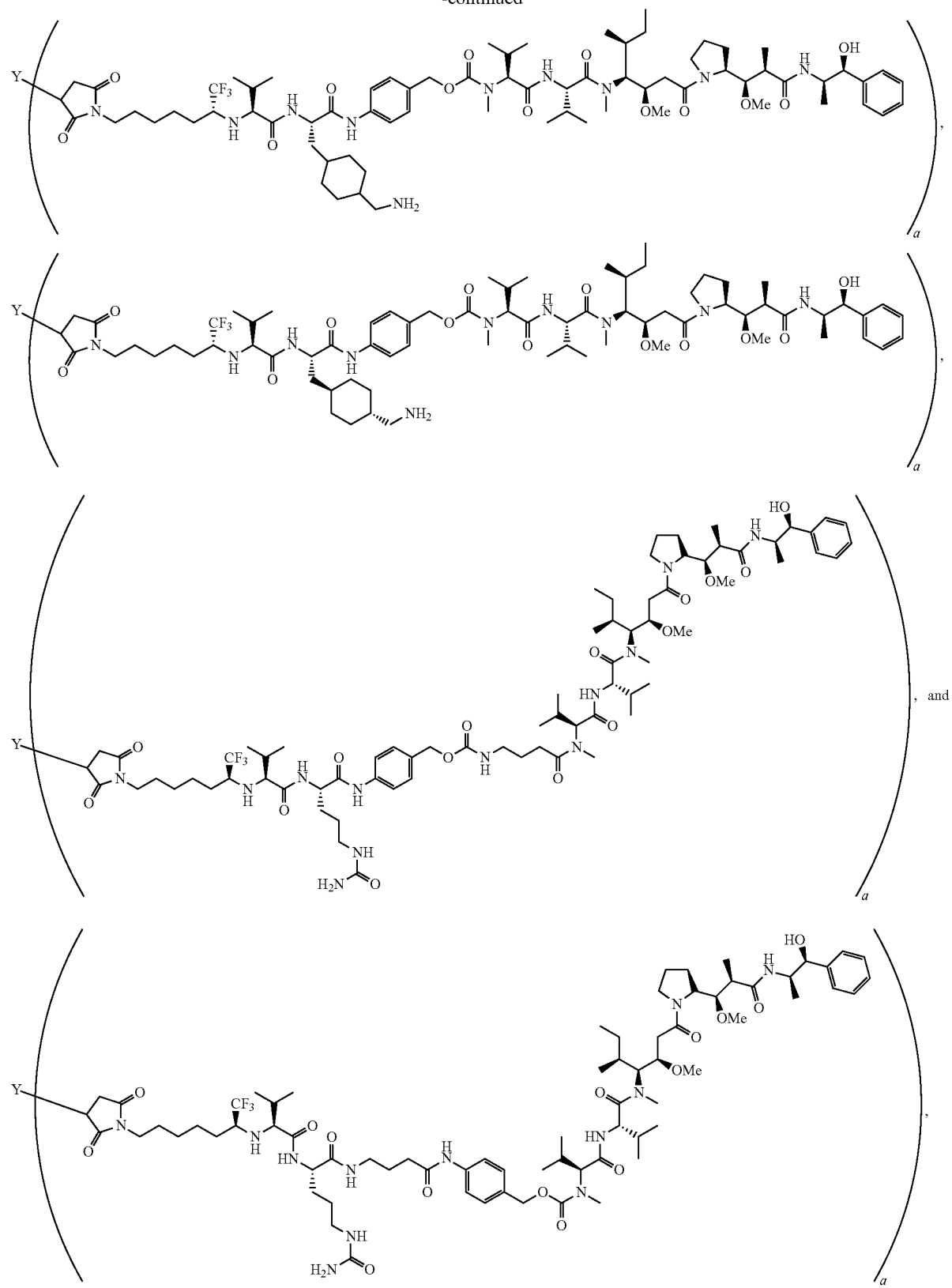
wherein Y is an antibody, a is an integer or decimal selected from 1-8.
28. The ADC of claim 27, it is selected from the group consisting of

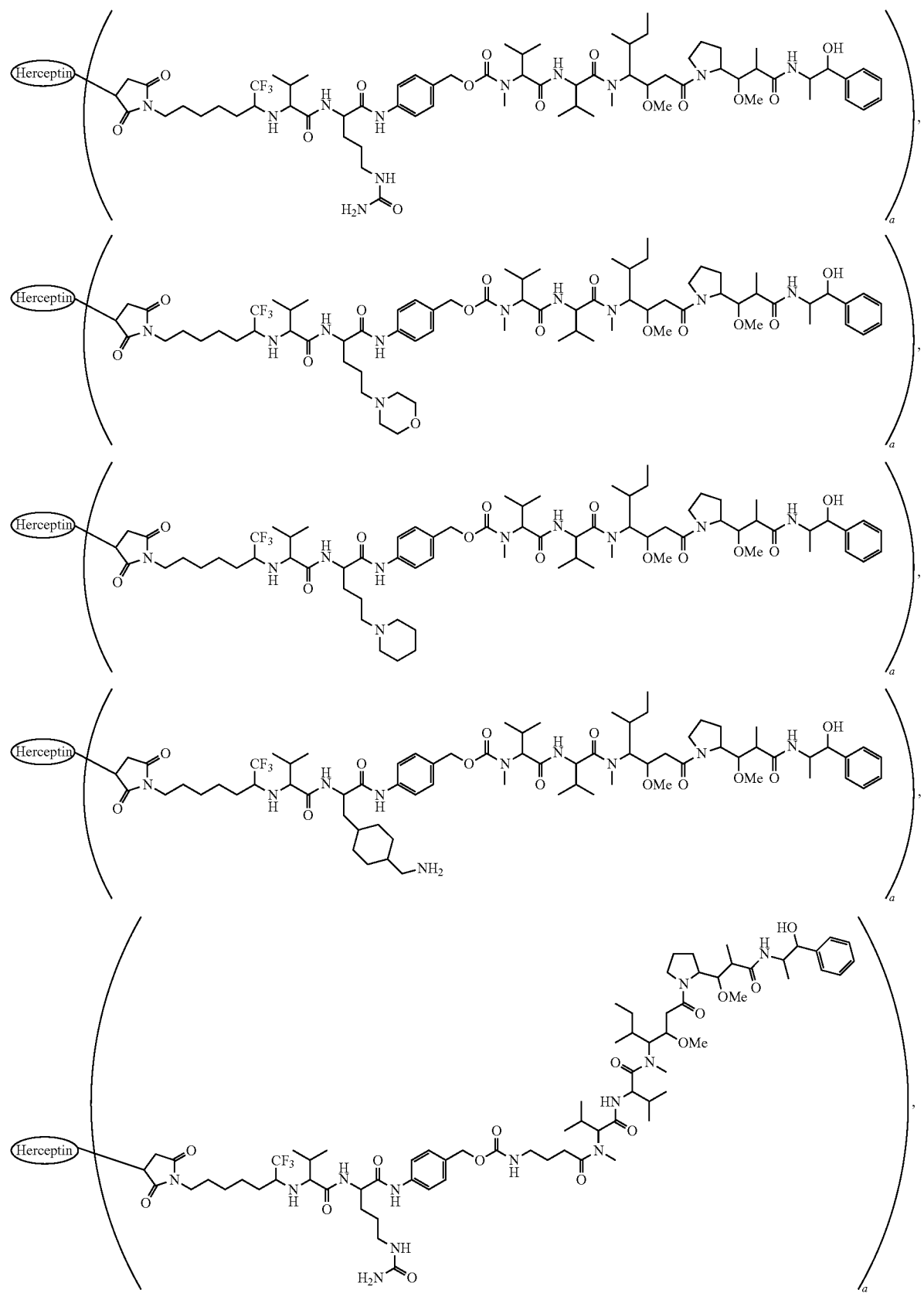

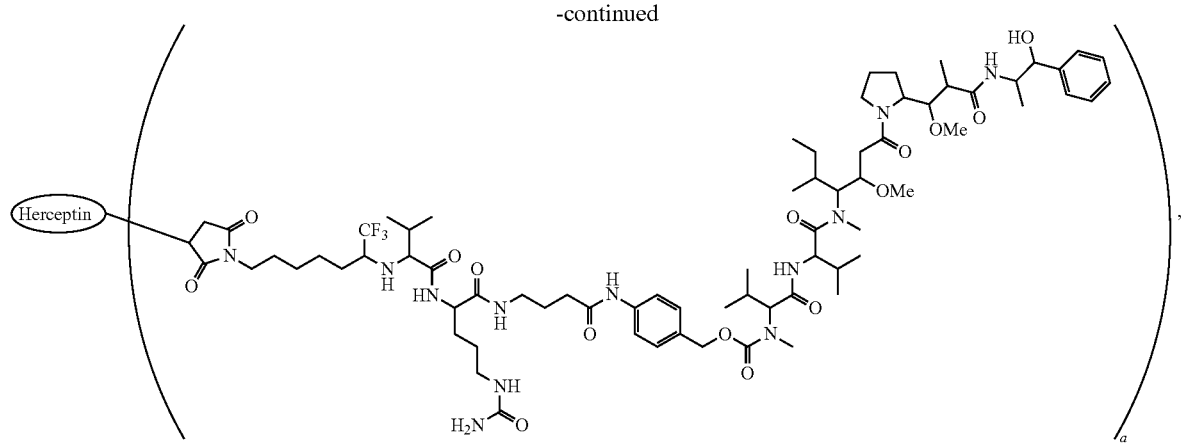
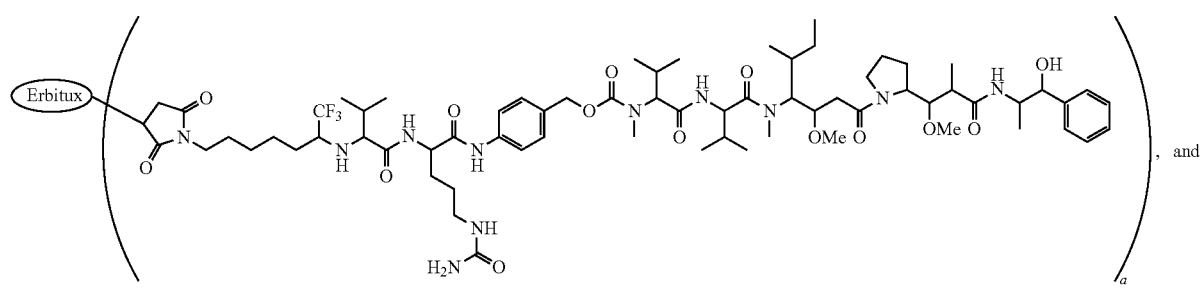
, and
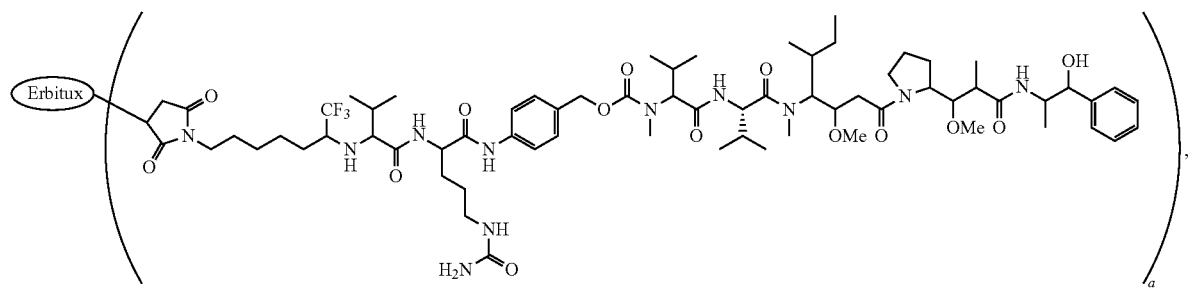
,
wherein a is an integer or decimal selected from 2-6.
29. The ADC of claim 28, it is selected from the group consisting of
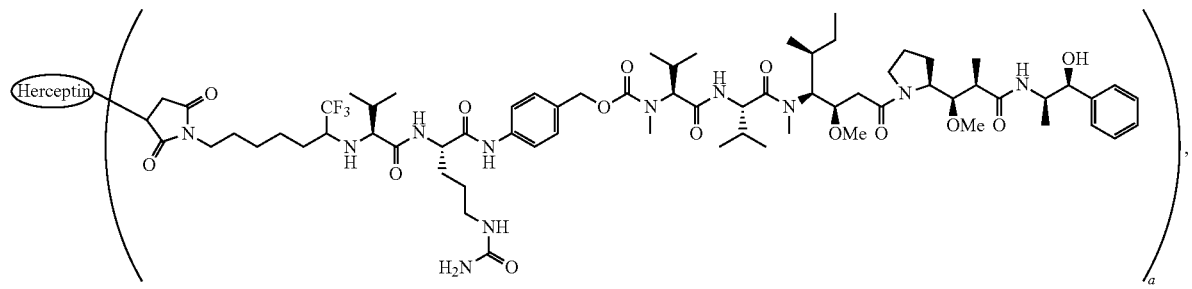
,

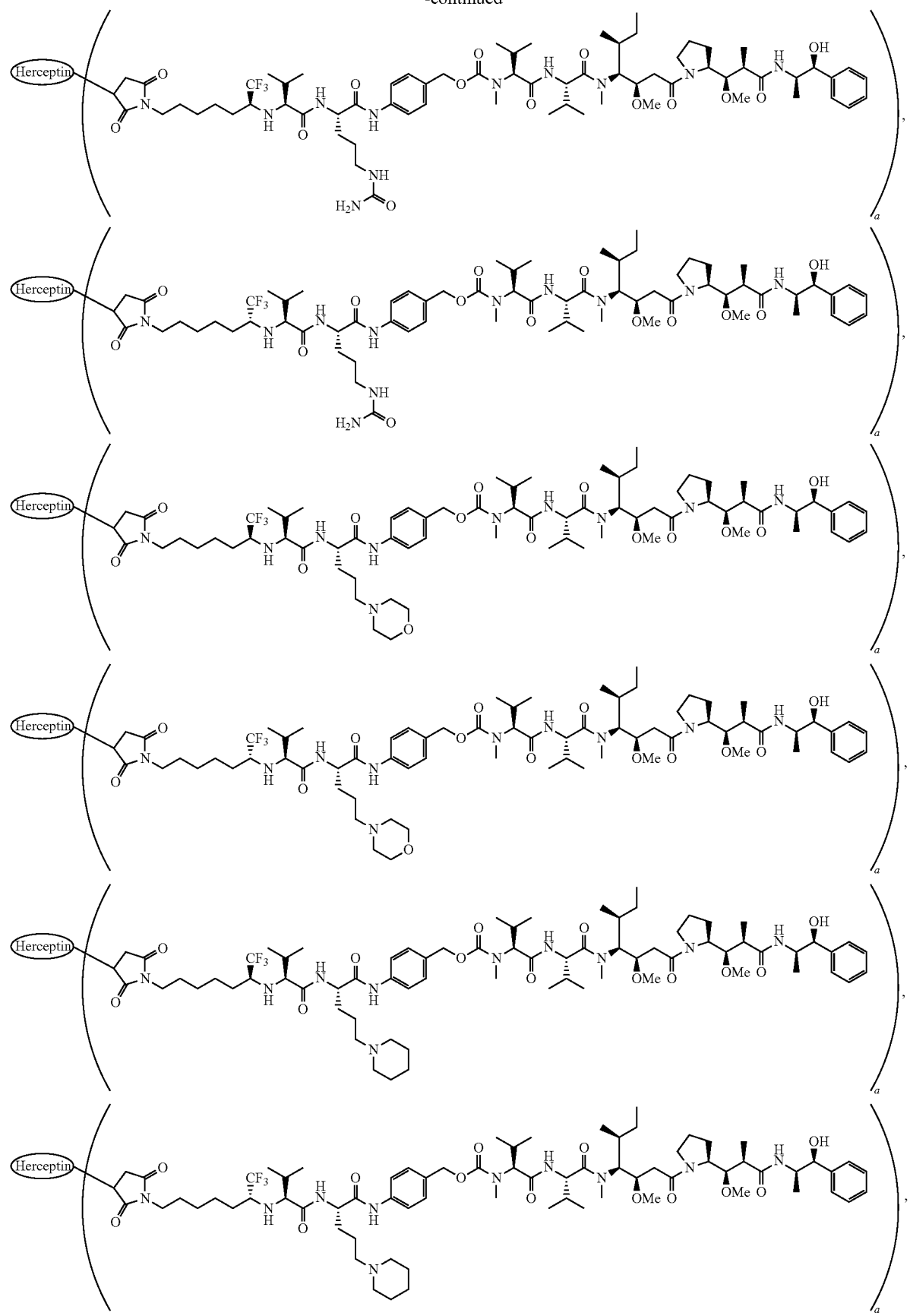

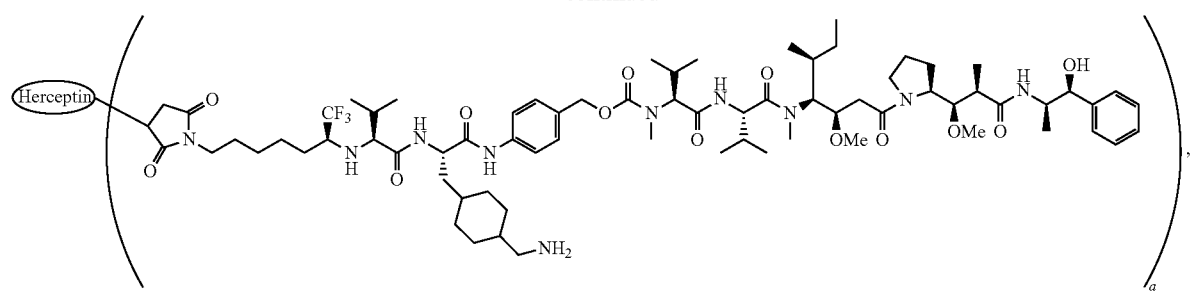
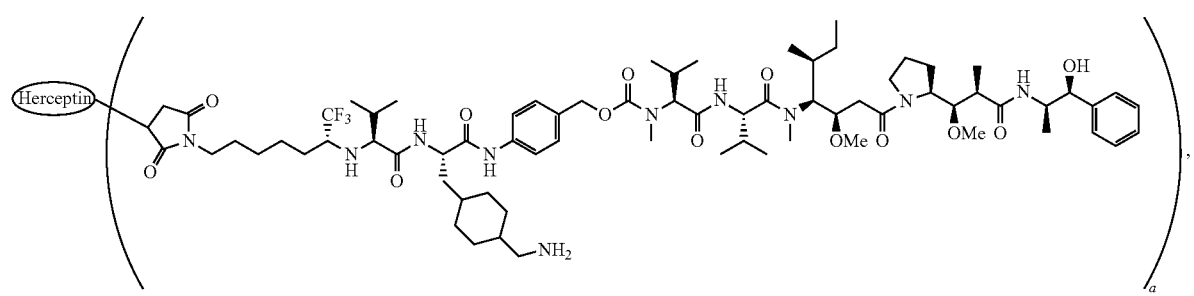
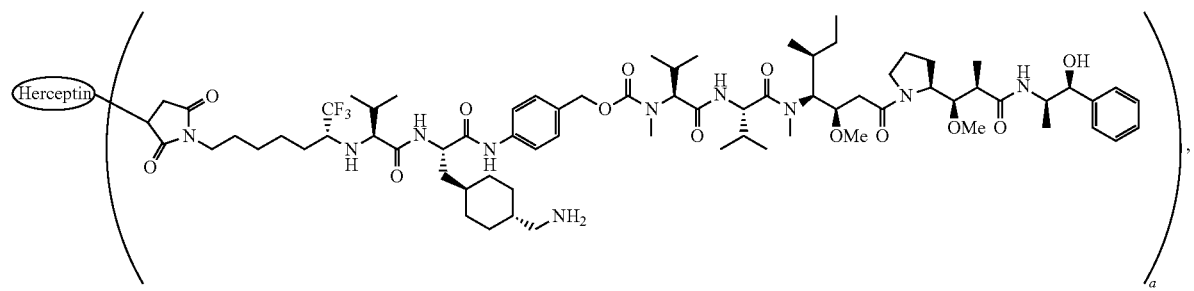
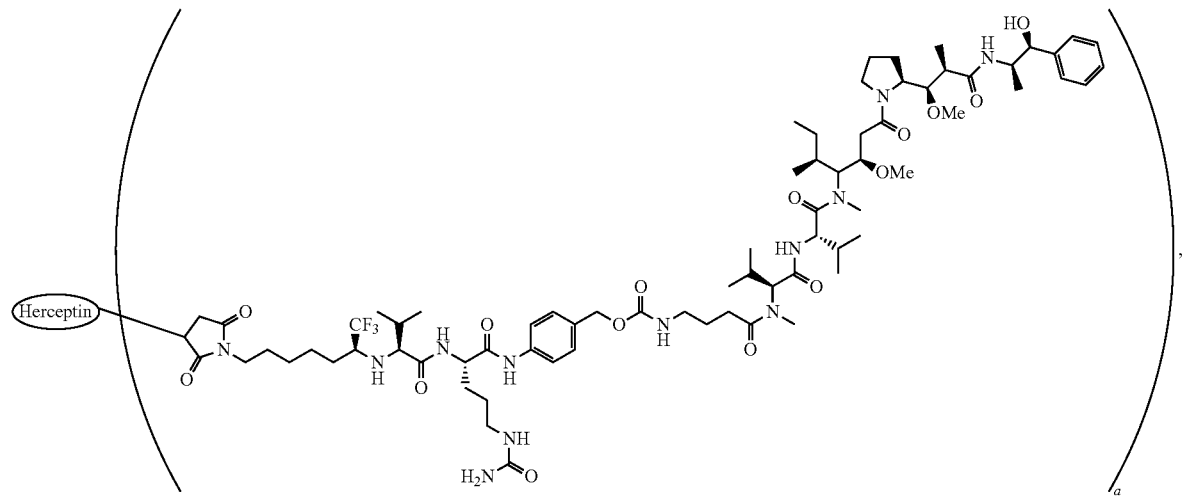

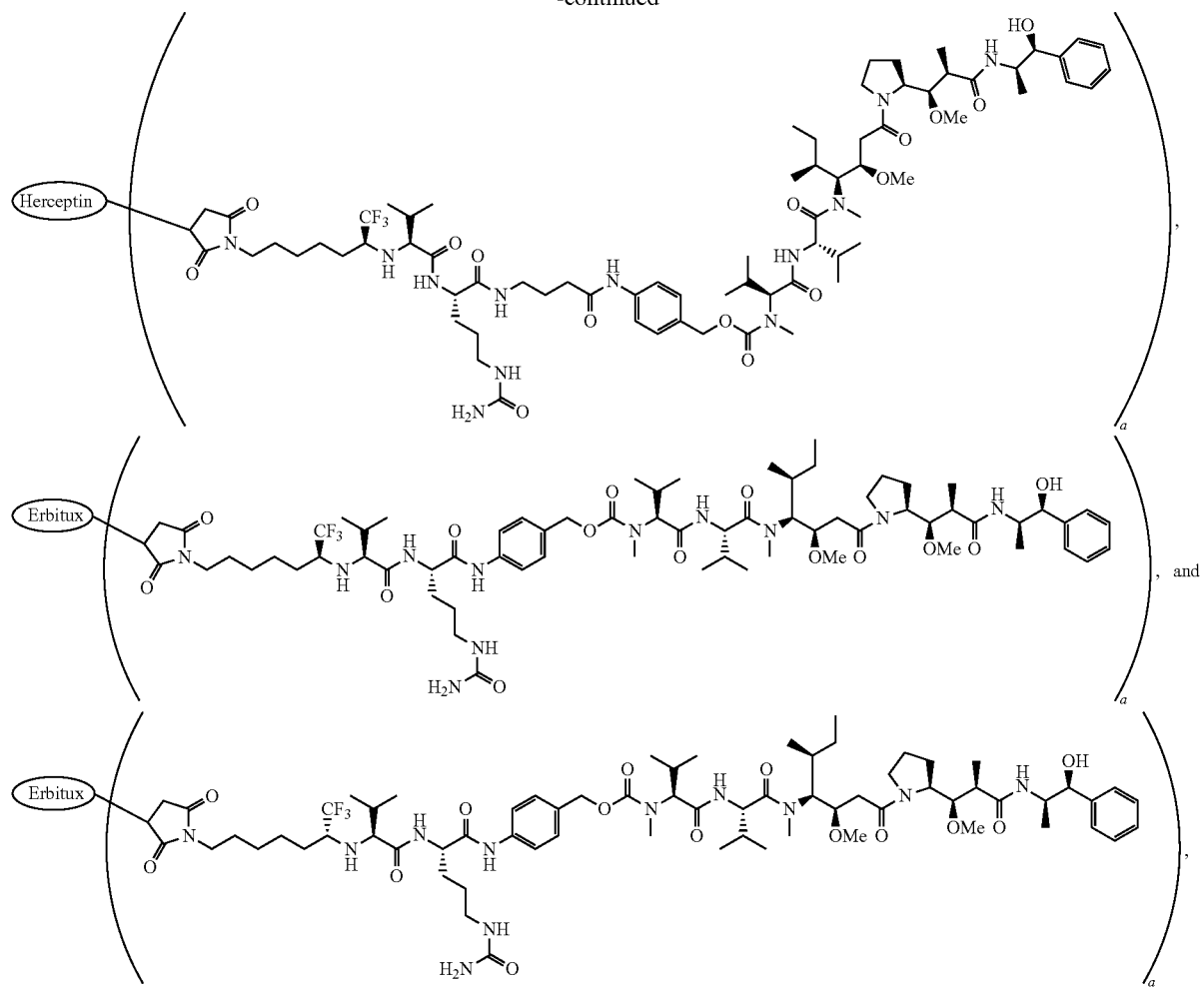
wherein a is an integer or decimal selected from 2-6.
* * * * *